(12) United States Patent
Leimbach et al.

(10) Patent No.: US 12,082,814 B2
(45) Date of Patent: *Sep. 10, 2024

(54) SURGICAL STAPLING DEVICE WITH LOCKOUT SYSTEM FOR PREVENTING ACTUATION IN THE ABSENCE OF AN INSTALLED STAPLE CARTRIDGE

(71) Applicant: Cilag GmbH International, Zug (CH)

(72) Inventors: Richard L. Leimbach, Cincinnati, OH (US); Michael E. Setser, Burlington, KY (US)

(73) Assignee: Cilag GmbH International, Zug (CH)

( * ) Notice: Subject to any disclaimer, the term of this patent is extended or adjusted under 35 U.S.C. 154(b) by 185 days.

This patent is subject to a terminal disclaimer.

(21) Appl. No.: 16/230,343

(22) Filed: Dec. 21, 2018

(65) Prior Publication Data

US 2019/0192161 A1 Jun. 27, 2019

Related U.S. Application Data

(63) Continuation of application No. 14/746,305, filed on Jun. 22, 2015, now Pat. No. 10,166,025, which is a (Continued)

(51) Int. Cl.
*A61B 17/072* (2006.01)
*A61B 17/068* (2006.01)
(Continued)

(52) U.S. Cl.
CPC .......... *A61B 17/105* (2013.01); *A61B 17/068* (2013.01); *A61B 17/072* (2013.01);
(Continued)

(58) Field of Classification Search
CPC ................ A61B 17/068; A61B 17/072; A61B 17/07207; A61B 2017/07271
(Continued)

(56) References Cited

U.S. PATENT DOCUMENTS 3,490,675 A 1/1970 Green et al.
3,494,533 A 2/1970 Green et al.
(Continued)

FOREIGN PATENT DOCUMENTS

AU 2012200178 B2 7/2013
CN 2488482 Y 5/2002
(Continued)

OTHER PUBLICATIONS

Disclosed Anonymously, "Motor-Driven Surgical Stapler Improvements," Research Disclosure Database No. 526041, Published: Feb. 2008.
(Continued)

*Primary Examiner* — Michelle Lopez
(74) *Attorney, Agent, or Firm* — Frost Brown Todd LLP

(57) ABSTRACT

Surgical stapling instruments having surgical stapling cartridges are disclosed. At least one embodiment includes an end effector that has an elongate channel that is configured to operably support a surgical staple cartridge therein and an anvil that is movably supported on the elongate channel between an open position and closed positions in response to an application of opening and closing motions applied thereto. An anvil lock member cooperates with the anvil to retain the anvil in an open position when a staple cartridge has not been installed in the elongate channel and prevent the anvil from moving to a closed position until the staple cartridge has been seated within the elongate channel. Surgical staple cartridges are configured to move the anvil from an open position to an actuatable position when the cartridge has been installed in the end effector.

16 Claims, 25 Drawing Sheets

Related U.S. Application Data continuation of application No. 13/429,647, filed on Mar. 26, 2012, now Pat. No. 9,078,653.

(51) Int. Cl.
*A61B 17/10* (2006.01)
*A61B 17/00* (2006.01)
*A61B 17/29* (2006.01)
*A61B 90/00* (2016.01)

(52) U.S. Cl.
CPC ............ *A61B 17/07207* (2013.01); *A61B 2017/00305* (2013.01); *A61B 2017/00327* (2013.01); *A61B 2017/07214* (2013.01); *A61B 2017/07257* (2013.01); *A61B 2017/07271* (2013.01); *A61B 2017/2923* (2013.01); *A61B 2017/2927* (2013.01); *A61B 2017/2936* (2013.01); *A61B 2090/035* (2016.02)

(58) Field of Classification Search
USPC .......................................... 227/175.1, 176.1
See application file for complete search history.

(56) References Cited

U.S. PATENT DOCUMENTS

| | | |
|---|---|---|
| 3,643,851 A | 2/1972 | Green et al. |
| 3,662,939 A | 5/1972 | Bryan |
| 3,717,294 A | 2/1973 | Green |
| 3,819,100 A | 6/1974 | Noiles et al. |
| RE28,932 E | 8/1976 | Noiles et al. |
| 4,111,206 A | 9/1978 | Vishnevsky et al. |
| 4,272,002 A | 6/1981 | Moshofsky |
| 4,305,539 A | 12/1981 | Korolkov et al. |
| 4,331,277 A | 5/1982 | Green |
| 4,379,457 A | 4/1983 | Gravener et al. |
| 4,383,634 A | 5/1983 | Green |
| 4,396,139 A | 8/1983 | Hall et al. |
| 4,397,311 A | 8/1983 | Kanshin et al. |
| 4,402,445 A | 9/1983 | Green |
| 4,415,112 A | 11/1983 | Green |
| 4,429,695 A | 2/1984 | Green |
| 4,434,796 A | 3/1984 | Karapetian et al. |
| 4,438,659 A | 3/1984 | Desplats |
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,520,817 A | 6/1985 | Green |
| 4,522,327 A | 6/1985 | Korthoff et al. |
| 4,530,453 A | 7/1985 | Green |
| 4,566,620 A | 1/1986 | Green et al. |
| 4,573,622 A | 3/1986 | Green et al. |
| 4,580,712 A | 4/1986 | Green |
| 4,585,153 A | 4/1986 | Failla et al. |
| 4,605,001 A | 8/1986 | Rothfuss et al. |
| 4,605,004 A | 8/1986 | Di Giovanni et al. |
| 4,608,981 A | 9/1986 | Rothfuss et al. |
| 4,610,383 A | 9/1986 | Rothfuss et al. |
| 4,612,933 A | 9/1986 | Brinkerhoff et al. |
| 4,619,391 A | 10/1986 | Sharkany et al. |
| 4,629,107 A | 12/1986 | Fedotov et al. |
| 4,632,290 A | 12/1986 | Green et al. |
| 4,633,874 A | 1/1987 | Chow et al. |
| 4,634,419 A | 1/1987 | Kreizman et al. |
| 4,655,222 A | 4/1987 | Florez et al. |
| 4,662,555 A | 5/1987 | Thornton |
| 4,664,305 A | 5/1987 | Blake, III et al. |
| 4,669,647 A | 6/1987 | Storace |
| 4,671,445 A | 6/1987 | Barker et al. |
| 4,684,051 A | 8/1987 | Akopov et al. |
| 4,700,703 A | 10/1987 | Resnick et al. |
| 4,715,520 A | 12/1987 | Roehr, Jr. et al. |
| 4,719,917 A | 1/1988 | Barrows et al. |
| 4,727,308 A | 2/1988 | Huljak et al. |
| 4,728,020 A | 3/1988 | Green et al. |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,844,068 A | 7/1989 | Arata et al. |
| 4,848,637 A | 7/1989 | Pruitt |
| 4,865,030 A | 9/1989 | Polyak |
| 4,869,414 A | 9/1989 | Green et al. |
| 4,869,415 A | 9/1989 | Fox |
| 4,896,678 A | 1/1990 | Ogawa |
| 4,931,047 A | 6/1990 | Broadwin et al. |
| 4,938,408 A | 7/1990 | Bedi et al. |
| 4,941,623 A | 7/1990 | Pruitt |
| 4,944,443 A | 7/1990 | Oddsen et al. |
| 4,978,333 A | 12/1990 | Broadwin et al. |
| 4,986,808 A | 1/1991 | Broadwin et al. |
| 5,002,553 A | 3/1991 | Shiber |
| 5,015,227 A | 5/1991 | Broadwin et al. |
| 5,038,109 A | 8/1991 | Goble et al. |
| 5,065,929 A | 11/1991 | Schulze et al. |
| 5,071,430 A | 12/1991 | de Salis et al. |
| 5,088,997 A | 2/1992 | Delahuerga et al. |
| 5,104,397 A | 4/1992 | Vasconcelos et al. |
| 5,122,156 A | 6/1992 | Granger et al. |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,156,315 A | 10/1992 | Green et al. |
| 5,158,567 A | 10/1992 | Green |
| 5,190,517 A | 3/1993 | Zieve et al. |
| 5,221,036 A | 6/1993 | Takase |
| 5,221,281 A | 6/1993 | Klicek |
| 5,222,975 A | 6/1993 | Crainich |
| 5,236,440 A | 8/1993 | Hlavacek |
| 5,240,163 A | 8/1993 | Stein et al. |
| 5,258,009 A | 11/1993 | Conners |
| 5,258,012 A | 11/1993 | Luscombe et al. |
| 5,281,216 A | 1/1994 | Klicek |
| 5,282,829 A | 2/1994 | Hermes |
| 5,284,128 A | 2/1994 | Hart |
| 5,304,204 A | 4/1994 | Bregen |
| 5,312,023 A | 5/1994 | Green et al. |
| 5,312,329 A | 5/1994 | Beaty et al. |
| 5,333,772 A | 8/1994 | Rothfuss et al. |
| 5,342,395 A | 8/1994 | Jarrett et al. |
| 5,342,396 A | 8/1994 | Cook |
| 5,346,504 A | 9/1994 | Ortiz et al. |
| 5,350,400 A | 9/1994 | Esposito et al. |
| 5,358,506 A | 10/1994 | Green et al. |
| 5,364,001 A | 11/1994 | Bryan |
| 5,366,479 A | 11/1994 | McGarry et al. |
| 5,370,645 A | 12/1994 | Klicek et al. |
| 5,372,596 A | 12/1994 | Klicek et al. |
| 5,374,277 A | 12/1994 | Hassler |
| 5,381,943 A | 1/1995 | Allen et al. |
| 5,382,247 A | 1/1995 | Cimino et al. |
| 5,383,880 A | 1/1995 | Hooven |
| 5,389,104 A | 2/1995 | Hahnen et al. |
| 5,395,033 A | 3/1995 | Byrne et al. |
| 5,395,384 A | 3/1995 | Duthoit et al. |
| 5,397,046 A | 3/1995 | Savage et al. |
| 5,403,312 A | 4/1995 | Yates et al. |
| 5,405,072 A | 4/1995 | Zlock et al. |
| 5,405,344 A | 4/1995 | Williamson et al. |
| 5,413,267 A * | 5/1995 | Solyntjes ............ A61B 17/072 227/175.4 |
| 5,413,272 A | 5/1995 | Green et al. |
| 5,413,573 A | 5/1995 | Koivukangas |
| 5,417,361 A | 5/1995 | Williamson, IV |

(56) References Cited

U.S. PATENT DOCUMENTS

| | | |
|---|---|---|
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,425,745 A | 6/1995 | Green et al. |
| 5,433,721 A | 7/1995 | Hooven et al. |
| 5,438,302 A | 8/1995 | Goble |
| 5,441,483 A | 8/1995 | Avitall |
| 5,447,265 A | 9/1995 | Vidal et al. |
| 5,447,417 A | 9/1995 | Kuhl et al. |
| 5,449,355 A | 9/1995 | Rhum et al. |
| 5,452,837 A | 9/1995 | Williamson, IV et al. |
| 5,462,215 A | 10/1995 | Viola et al. |
| 5,465,896 A | 11/1995 | Allen et al. |
| 5,466,020 A | 11/1995 | Page et al. |
| 5,472,442 A | 12/1995 | Klicek |
| 5,474,057 A | 12/1995 | Makower et al. |
| 5,474,566 A | 12/1995 | Alesi et al. |
| 5,478,354 A | 12/1995 | Tovey et al. |
| 5,480,089 A | 1/1996 | Blewett |
| 5,484,398 A | 1/1996 | Stoddard |
| 5,485,947 A | 1/1996 | Olson et al. |
| 5,485,952 A | 1/1996 | Fontayne |
| 5,487,499 A | 1/1996 | Sorrentino et al. |
| 5,489,058 A | 2/1996 | Plyley et al. |
| 5,496,312 A | 3/1996 | Klicek |
| 5,496,317 A | 3/1996 | Goble et al. |
| 5,497,933 A | 3/1996 | DeFonzo et al. |
| 5,503,320 A | 4/1996 | Webster et al. |
| 5,503,638 A | 4/1996 | Cooper et al. |
| 5,505,363 A | 4/1996 | Green et al. |
| 5,509,596 A | 4/1996 | Green et al. |
| 5,509,916 A | 4/1996 | Taylor |
| 5,520,678 A | 5/1996 | Heckele et al. |
| 5,529,235 A | 6/1996 | Boiarski et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,541,376 A | 7/1996 | Ladtkow et al. |
| 5,547,117 A | 8/1996 | Hamblin et al. |
| 5,553,765 A | 9/1996 | Knodel et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,564,615 A | 10/1996 | Bishop et al. |
| 5,571,285 A | 11/1996 | Chow et al. |
| 5,577,654 A | 11/1996 | Bishop |
| 5,579,978 A | 12/1996 | Green et al. |
| 5,580,067 A | 12/1996 | Hamblin et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,597,107 A | 1/1997 | Knodel et al. |
| 5,599,344 A | 2/1997 | Paterson |
| 5,601,224 A | 2/1997 | Bishop et al. |
| 5,605,272 A | 2/1997 | Witt et al. |
| 5,605,273 A | 2/1997 | Hamblin et al. |
| 5,607,094 A | 3/1997 | Clark et al. |
| 5,609,601 A | 3/1997 | Kolesa et al. |
| 5,611,709 A | 3/1997 | McAnulty |
| 5,613,966 A | 3/1997 | Makower et al. |
| 5,615,820 A | 4/1997 | Viola |
| 5,618,303 A | 4/1997 | Marlow et al. |
| 5,619,992 A | 4/1997 | Guthrie et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,632,432 A | 5/1997 | Schulze et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,645,209 A | 7/1997 | Green et al. |
| 5,647,526 A | 7/1997 | Green et al. |
| 5,647,869 A | 7/1997 | Goble et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,662,667 A | 9/1997 | Knodel |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,693,020 A | 12/1997 | Rauh |
| 5,693,051 A | 12/1997 | Schulze et al. |
| 5,695,494 A | 12/1997 | Becker |
| 5,695,524 A | 12/1997 | Kelley et al. |
| 5,697,543 A | 12/1997 | Burdorff |
| 5,702,387 A | 12/1997 | Arts et al. |
| 5,704,534 A | 1/1998 | Huitema et al. |
| 5,706,997 A | 1/1998 | Green et al. |
| 5,706,998 A | 1/1998 | Plyley et al. |
| 5,709,334 A | 1/1998 | Sorrentino et al. |
| 5,709,680 A | 1/1998 | Yates et al. |
| 5,711,472 A | 1/1998 | Bryan |
| 5,713,895 A | 2/1998 | Lontine et al. |
| 5,715,604 A | 2/1998 | Lanzoni |
| 5,715,987 A | 2/1998 | Kelley et al. |
| 5,715,988 A | 2/1998 | Palmer |
| 5,718,359 A | 2/1998 | Palmer et al. |
| 5,720,744 A | 2/1998 | Eggleston et al. |
| 5,725,554 A | 3/1998 | Simon et al. |
| 5,730,758 A | 3/1998 | Allgeyer |
| 5,732,871 A | 3/1998 | Clark et al. |
| 5,732,872 A | 3/1998 | Bolduc et al. |
| 5,735,445 A | 4/1998 | Vidal et al. |
| 5,735,874 A | 4/1998 | Measamer et al. |
| 5,743,456 A | 4/1998 | Jones et al. |
| 5,749,893 A | 5/1998 | Vidal et al. |
| 5,752,644 A | 5/1998 | Bolanos et al. |
| 5,752,965 A | 5/1998 | Francis et al. |
| 5,762,255 A | 6/1998 | Chrisman et al. |
| 5,762,256 A | 6/1998 | Mastri et al. |
| 5,772,659 A | 6/1998 | Becker et al. |
| 5,776,130 A | 7/1998 | Buysse et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,748 A | 7/1998 | Palmer et al. |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,800,379 A | 9/1998 | Edwards |
| 5,807,393 A | 9/1998 | Williamson, IV et al. |
| 5,814,055 A | 9/1998 | Knodel et al. |
| 5,820,009 A | 10/1998 | Melling et al. |
| 5,826,776 A | 10/1998 | Schulze et al. |
| 5,827,271 A | 10/1998 | Buysse et al. |
| 5,830,598 A | 11/1998 | Patterson |
| 5,833,695 A | 11/1998 | Yoon |

(56) References Cited

U.S. PATENT DOCUMENTS

| | | | |
|---|---|---|---|
| 5,836,503 A | 11/1998 | Ehrenfels et al. |
| 5,839,639 A | 11/1998 | Sauer et al. |
| 5,843,021 A | 12/1998 | Edwards et al. |
| 5,855,311 A | 1/1999 | Hamblin et al. |
| 5,860,975 A | 1/1999 | Goble et al. |
| 5,865,361 A | 2/1999 | Milliman et al. |
| 5,868,760 A | 2/1999 | McGuckin, Jr. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,897,552 A | 4/1999 | Edwards et al. |
| 5,901,895 A | 5/1999 | Heaton et al. |
| 5,902,312 A | 5/1999 | Frater et al. |
| 5,908,402 A | 6/1999 | Blythe |
| 5,918,791 A | 7/1999 | Sorrentino et al. |
| 5,937,951 A | 8/1999 | Izuchukwu et al. |
| 5,941,442 A | 8/1999 | Geiste et al. |
| 5,944,715 A | 8/1999 | Goble et al. |
| 5,947,984 A | 9/1999 | Whipple |
| 5,951,552 A | 9/1999 | Long et al. |
| 5,954,259 A | 9/1999 | Viola et al. |
| 5,988,479 A | 11/1999 | Palmer |
| 6,004,319 A | 12/1999 | Goble et al. |
| 6,010,054 A | 1/2000 | Johnson et al. |
| 6,012,494 A | 1/2000 | Balazs |
| 6,013,076 A | 1/2000 | Goble et al. |
| 6,015,406 A | 1/2000 | Goble et al. |
| 6,027,501 A | 2/2000 | Goble et al. |
| 6,032,849 A | 3/2000 | Mastri et al. |
| 6,033,399 A | 3/2000 | Gines |
| 6,039,734 A | 3/2000 | Goble |
| 6,050,172 A | 4/2000 | Corves et al. |
| 6,050,472 A | 4/2000 | Shibata |
| 6,050,996 A | 4/2000 | Schmaltz et al. |
| 6,068,627 A | 5/2000 | Orszulak et al. |
| 6,074,401 A | 6/2000 | Gardiner et al. |
| 6,079,606 A | 6/2000 | Milliman et al. |
| 6,083,191 A | 7/2000 | Rose |
| 6,083,242 A | 7/2000 | Cook |
| 6,093,186 A | 7/2000 | Goble |
| 6,099,551 A | 8/2000 | Gabbay |
| 6,109,500 A | 8/2000 | Alli et al. |
| 6,117,158 A | 9/2000 | Measamer et al. |
| 6,119,913 A | 9/2000 | Adams et al. |
| 6,131,789 A | 10/2000 | Schulze et al. |
| 6,131,790 A | 10/2000 | Piraka |
| 6,149,660 A | 11/2000 | Laufer et al. |
| 6,155,473 A | 12/2000 | Tompkins et al. |
| 6,156,056 A | 12/2000 | Kearns et al. |
| 6,162,208 A | 12/2000 | Hipps |
| 6,171,330 B1 | 1/2001 | Benchetrit |
| 6,187,003 B1 | 2/2001 | Buysse et al. |
| 6,202,914 B1 | 3/2001 | Geiste et al. |
| 6,210,403 B1 | 4/2001 | Klicek |
| 6,213,999 B1 | 4/2001 | Platt, Jr. et al. |
| 6,228,081 B1 | 5/2001 | Goble |
| 6,228,083 B1 | 5/2001 | Lands et al. |
| 6,241,139 B1 | 6/2001 | Milliman et al. |
| 6,250,532 B1 | 6/2001 | Green et al. |
| 6,261,286 B1 | 7/2001 | Goble et al. |
| 6,273,897 B1 | 8/2001 | Dalessandro et al. |
| 6,277,114 B1 | 8/2001 | Bullivant et al. |
| 6,302,311 B1 | 10/2001 | Adams et al. |
| 6,322,494 B1 | 11/2001 | Bullivant et al. |
| 6,325,799 B1 | 12/2001 | Goble |
| 6,325,805 B1 | 12/2001 | Ogilvie et al. |
| 6,325,810 B1 | 12/2001 | Hamilton et al. |
| 6,330,965 B1 | 12/2001 | Milliman et al. |
| 6,334,861 B1 | 1/2002 | Chandler et al. |
| 6,336,926 B1 | 1/2002 | Goble |
| 6,338,737 B1 | 1/2002 | Toledano |
| 6,358,224 B1 | 3/2002 | Tims et al. |
| 6,387,113 B1 | 5/2002 | Hawkins et al. |
| H2037 H | 7/2002 | Yates et al. |
| RE37,814 E | 8/2002 | Allgeyer |
| 6,439,446 B1 | 8/2002 | Perry et al. |
| 6,443,973 B1 | 9/2002 | Whitman |
| 6,450,391 B1 | 9/2002 | Kayan et al. |
| 6,488,196 B1 | 12/2002 | Fenton, Jr. |
| 6,488,197 B1 | 12/2002 | Whitman |
| 6,488,659 B1 | 12/2002 | Rosenman |
| 6,491,201 B1 | 12/2002 | Whitman |
| 6,491,690 B1 | 12/2002 | Goble et al. |
| 6,505,768 B2 | 1/2003 | Whitman |
| 6,517,528 B1 | 2/2003 | Pantages et al. |
| 6,517,565 B1 | 2/2003 | Whitman et al. |
| 6,517,566 B1 | 2/2003 | Hovland et al. |
| 6,533,157 B1 | 3/2003 | Whitman |
| 6,558,379 B1 | 5/2003 | Batchelor et al. |
| 6,569,085 B2 | 5/2003 | Kortenbach et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,597 B2 | 7/2003 | Grant et al. |
| 6,607,475 B2 | 8/2003 | Doyle et al. |
| 6,616,686 B2 | 9/2003 | Coleman et al. |
| 6,619,529 B2 | 9/2003 | Green et al. |
| 6,629,988 B2 | 10/2003 | Weadock |
| 6,638,297 B1 | 10/2003 | Huitema |
| 6,644,532 B2 | 11/2003 | Green et al. |
| 6,656,193 B2 | 12/2003 | Grant et al. |
| 6,669,073 B2 | 12/2003 | Milliman et al. |
| 6,676,660 B2 | 1/2004 | Wampler et al. |
| 6,681,978 B2 | 1/2004 | Geiste et al. |
| 6,695,198 B2 | 2/2004 | Adams et al. |
| 6,698,643 B2 | 3/2004 | Whitman |
| 6,716,233 B1 | 4/2004 | Whitman |
| 6,722,552 B2 | 4/2004 | Fenton, Jr. |
| 6,723,109 B2 | 4/2004 | Solingen |
| 6,749,560 B1 | 6/2004 | Konstorum et al. |
| 6,755,338 B2 | 6/2004 | Hahnen et al. |
| 6,761,685 B2 | 7/2004 | Adams et al. |
| 6,769,590 B2 | 8/2004 | Vresh et al. |
| 6,769,594 B2 | 8/2004 | Orban, III |
| 6,786,382 B1 | 9/2004 | Hoffman |
| 6,793,652 B1 | 9/2004 | Whitman et al. |
| 6,793,661 B2 | 9/2004 | Hamilton et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,830,174 B2 | 12/2004 | Hillstead et al. |
| 6,835,336 B2 | 12/2004 | Watt |
| 6,840,423 B2 | 1/2005 | Adams et al. |
| 6,843,403 B2 | 1/2005 | Whitman |
| 6,858,005 B2 | 2/2005 | Ohline et al. |
| 6,866,178 B2 | 3/2005 | Adams et al. |
| 6,874,669 B2 | 4/2005 | Adams et al. |
| 6,877,647 B2 | 4/2005 | Green et al. |
| 6,878,106 B1 | 4/2005 | Herrmann |
| 6,905,057 B2 | 6/2005 | Swayze et al. |
| 6,908,472 B2 | 6/2005 | Wiener et al. |
| 6,932,810 B2 | 8/2005 | Ryan |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,981,628 B2 | 1/2006 | Wales |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,995,729 B2 | 2/2006 | Govari et al. |
| 7,000,818 B2 | 2/2006 | Shelton, IV et al. |
| 7,000,819 B2 | 2/2006 | Swayze et al. |
| 7,001,408 B2 | 2/2006 | Knodel et al. |
| 7,008,435 B2 | 3/2006 | Cummins |
| 7,018,357 B2 | 3/2006 | Emmons |
| 7,032,798 B2 | 4/2006 | Whitman et al. |
| 7,032,799 B2 | 4/2006 | Viola et al. |

(56) References Cited

U.S. PATENT DOCUMENTS

| | | | |
|---|---|---|---|
| 7,044,352 B2* | 5/2006 | Shelton, IV | A61B 17/07207 227/175.4 |
| 7,044,353 B2* | 5/2006 | Mastri | A61B 17/0684 227/176.1 |
| 7,052,494 B2 | 5/2006 | Goble et al. | |
| 7,055,730 B2 | 6/2006 | Ehrenfels et al. | |
| 7,055,731 B2 | 6/2006 | Shelton, IV et al. | |
| 7,056,330 B2 | 6/2006 | Gayton | |
| 7,059,508 B2 | 6/2006 | Shelton, IV et al. | |
| 7,070,083 B2 | 7/2006 | Jankowski | |
| 7,077,856 B2 | 7/2006 | Whitman | |
| 7,080,769 B2 | 7/2006 | Vresh et al. | |
| 7,083,075 B2 | 8/2006 | Swayze et al. | |
| 7,097,089 B2 | 8/2006 | Marczyk | |
| 7,097,644 B2 | 8/2006 | Long | |
| 7,108,709 B2 | 9/2006 | Cummins | |
| 7,111,769 B2 | 9/2006 | Wales et al. | |
| 7,121,446 B2 | 10/2006 | Arad et al. | |
| 7,128,253 B2 | 10/2006 | Mastri et al. | |
| 7,128,254 B2 | 10/2006 | Shelton, IV et al. | |
| 7,128,748 B2 | 10/2006 | Mooradian et al. | |
| 7,133,601 B2 | 11/2006 | Phillips et al. | |
| 7,137,981 B2 | 11/2006 | Long | |
| 7,140,527 B2 | 11/2006 | Ehrenfels et al. | |
| 7,140,528 B2 | 11/2006 | Shelton, IV | |
| 7,143,923 B2 | 12/2006 | Shelton, IV et al. | |
| 7,143,924 B2 | 12/2006 | Scirica et al. | |
| 7,143,925 B2 | 12/2006 | Shelton, IV et al. | |
| 7,143,926 B2 | 12/2006 | Shelton, IV et al. | |
| 7,147,138 B2 | 12/2006 | Shelton, IV | |
| 7,147,139 B2 | 12/2006 | Schwemberger et al. | |
| 7,147,637 B2 | 12/2006 | Goble | |
| 7,147,650 B2 | 12/2006 | Lee | |
| 7,150,748 B2 | 12/2006 | Ebbutt et al. | |
| 7,156,863 B2 | 1/2007 | Sonnenschein et al. | |
| 7,159,750 B2 | 1/2007 | Racenet et al. | |
| 7,168,604 B2 | 1/2007 | Milliman et al. | |
| 7,172,104 B2 | 2/2007 | Scirica et al. | |
| 7,182,239 B1 | 2/2007 | Myers | |
| 7,199,537 B2 | 4/2007 | Okamura et al. | |
| 7,204,404 B2 | 4/2007 | Nguyen et al. | |
| 7,204,835 B2 | 4/2007 | Latterell et al. | |
| 7,207,471 B2 | 4/2007 | Heinrich et al. | |
| 7,211,081 B2 | 5/2007 | Goble | |
| 7,213,736 B2 | 5/2007 | Wales et al. | |
| 7,220,272 B2 | 5/2007 | Weadock | |
| 7,225,963 B2 | 6/2007 | Scirica | |
| 7,225,964 B2 | 6/2007 | Mastri et al. | |
| 7,237,708 B1 | 7/2007 | Guy et al. | |
| 7,238,195 B2 | 7/2007 | Viola | |
| 7,246,734 B2 | 7/2007 | Shelton, IV | |
| 7,247,161 B2 | 7/2007 | Johnston et al. | |
| 7,258,262 B2 | 8/2007 | Mastri et al. | |
| 7,258,546 B2 | 8/2007 | Beier et al. | |
| 7,278,562 B2 | 10/2007 | Mastri et al. | |
| 7,282,048 B2 | 10/2007 | Goble et al. | |
| 7,293,685 B2 | 11/2007 | Ehrenfels et al. | |
| 7,296,722 B2 | 11/2007 | Ivanko | |
| 7,296,724 B2 | 11/2007 | Green et al. | |
| 7,300,450 B2 | 11/2007 | Vleugels et al. | |
| 7,303,106 B2 | 12/2007 | Milliman et al. | |
| 7,303,107 B2 | 12/2007 | Milliman et al. | |
| 7,303,108 B2 | 12/2007 | Shelton, IV | |
| 7,308,998 B2 | 12/2007 | Mastri et al. | |
| 7,326,203 B2 | 2/2008 | Papineau et al. | |
| 7,328,828 B2 | 2/2008 | Ortiz et al. | |
| 7,328,829 B2 | 2/2008 | Arad et al. | |
| 7,331,340 B2 | 2/2008 | Barney | |
| 7,334,717 B2 | 2/2008 | Rethy et al. | |
| 7,334,718 B2 | 2/2008 | McAlister et al. | |
| 7,336,048 B2 | 2/2008 | Lohr | |
| 7,354,447 B2 | 4/2008 | Shelton, IV et al. | |
| 7,357,287 B2 | 4/2008 | Shelton, IV et al. | |
| 7,357,806 B2 | 4/2008 | Rivera et al. | |
| 7,364,060 B2 | 4/2008 | Milliman | |
| 7,364,061 B2 | 4/2008 | Swayze et al. | |
| 7,380,695 B2 | 6/2008 | Doll et al. | |
| 7,380,696 B2 | 6/2008 | Shelton, IV et al. | |
| 7,396,356 B2 | 7/2008 | Mollenauer | |
| 7,398,907 B2 | 7/2008 | Racenet et al. | |
| 7,398,908 B2 | 7/2008 | Holsten et al. | |
| 7,401,721 B2 | 7/2008 | Holsten et al. | |
| 7,404,508 B2 | 7/2008 | Smith et al. | |
| 7,404,509 B2 | 7/2008 | Ortiz et al. | |
| 7,404,822 B2 | 7/2008 | Viart et al. | |
| 7,407,074 B2 | 8/2008 | Ortiz et al. | |
| 7,407,075 B2 | 8/2008 | Holsten et al. | |
| 7,407,076 B2 | 8/2008 | Racenet et al. | |
| 7,407,077 B2 | 8/2008 | Ortiz et al. | |
| 7,407,078 B2 | 8/2008 | Shelton, IV et al. | |
| 7,410,086 B2 | 8/2008 | Ortiz et al. | |
| 7,416,101 B2 | 8/2008 | Shelton, IV et al. | |
| RE40,514 E | 9/2008 | Mastri et al. | |
| 7,419,080 B2 | 9/2008 | Smith et al. | |
| 7,419,321 B2 | 9/2008 | Tereschouk | |
| 7,422,136 B1 | 9/2008 | Marczyk | |
| 7,422,139 B2 | 9/2008 | Shelton, IV et al. | |
| 7,427,607 B2 | 9/2008 | Suzuki | |
| 7,431,188 B1 | 10/2008 | Marczyk | |
| 7,431,189 B2 | 10/2008 | Shelton, IV et al. | |
| 7,431,694 B2 | 10/2008 | Stefanchik et al. | |
| 7,431,730 B2 | 10/2008 | Viola | |
| 7,434,715 B2 | 10/2008 | Shelton, IV et al. | |
| 7,434,717 B2 | 10/2008 | Shelton, IV et al. | |
| 7,438,209 B1 | 10/2008 | Hess et al. | |
| 7,438,718 B2 | 10/2008 | Milliman et al. | |
| 7,441,684 B2 | 10/2008 | Shelton, IV et al. | |
| 7,441,685 B1 | 10/2008 | Boudreaux | |
| 7,448,525 B2 | 11/2008 | Shelton, IV et al. | |
| 7,451,904 B2 | 11/2008 | Shelton, IV | |
| 7,455,682 B2 | 11/2008 | Viola | |
| 7,461,767 B2 | 12/2008 | Viola et al. | |
| 7,464,846 B2 | 12/2008 | Shelton, IV et al. | |
| 7,464,847 B2 | 12/2008 | Viola et al. | |
| 7,464,849 B2 | 12/2008 | Shelton, IV et al. | |
| 7,467,740 B2 | 12/2008 | Shelton, IV et al. | |
| 7,472,814 B2 | 1/2009 | Mastri et al. | |
| 7,472,815 B2 | 1/2009 | Shelton, IV et al. | |
| 7,472,816 B2 | 1/2009 | Holsten et al. | |
| 7,473,253 B2 | 1/2009 | Dycus et al. | |
| 7,481,347 B2 | 1/2009 | Roy | |
| 7,481,348 B2 | 1/2009 | Marczyk | |
| 7,481,349 B2 | 1/2009 | Holsten et al. | |
| 7,487,899 B2 | 2/2009 | Shelton, IV et al. | |
| 7,490,749 B2 | 2/2009 | Schall et al. | |
| 7,494,039 B2 | 2/2009 | Racenet et al. | |
| 7,500,979 B2 | 3/2009 | Hueil et al. | |
| 7,503,474 B2 | 3/2009 | Hillstead et al. | |
| 7,506,790 B2 | 3/2009 | Shelton, IV | |
| 7,506,791 B2 | 3/2009 | Omaits et al. | |
| 7,510,107 B2 | 3/2009 | Timm et al. | |
| 7,513,408 B2 | 4/2009 | Shelton, IV et al. | |
| 7,517,356 B2 | 4/2009 | Heinrich | |
| 7,547,312 B2 | 6/2009 | Bauman et al. | |
| 7,549,563 B2 | 6/2009 | Mather et al. | |
| 7,549,564 B2 | 6/2009 | Boudreaux | |
| 7,549,998 B2 | 6/2009 | Braun | |
| 7,552,854 B2 | 6/2009 | Wixey et al. | |
| 7,556,185 B2 | 7/2009 | Viola | |
| 7,559,449 B2 | 7/2009 | Viola | |
| 7,559,450 B2 | 7/2009 | Wales et al. | |
| 7,559,452 B2 | 7/2009 | Wales et al. | |
| 7,565,993 B2 | 7/2009 | Milliman et al. | |
| 7,568,603 B2 | 8/2009 | Shelton, IV et al. | |
| 7,575,144 B2 | 8/2009 | Ortiz et al. | |
| 7,588,174 B2 | 9/2009 | Holsten et al. | |
| 7,588,175 B2 | 9/2009 | Timm et al. | |
| 7,588,176 B2 | 9/2009 | Timm et al. | |
| 7,588,177 B2 | 9/2009 | Racenet | |
| 7,597,229 B2 | 10/2009 | Boudreaux et al. | |
| 7,597,230 B2 | 10/2009 | Racenet et al. | |
| 7,600,663 B2 | 10/2009 | Green | |
| 7,604,150 B2 | 10/2009 | Boudreaux | |
| 7,604,151 B2 | 10/2009 | Hess et al. | |

(56) References Cited

U.S. PATENT DOCUMENTS

| | | |
|---|---|---|
| 7,607,557 B2 | 10/2009 | Shelton, IV et al. |
| 7,611,038 B2 | 11/2009 | Racenet et al. |
| 7,615,067 B2 | 11/2009 | Lee et al. |
| 7,624,902 B2 | 12/2009 | Marczyk et al. |
| 7,624,903 B2 | 12/2009 | Green et al. |
| 7,625,370 B2 | 12/2009 | Hart et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,409 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,644,848 B2 | 1/2010 | Swayze et al. |
| 7,645,230 B2 | 1/2010 | Mikkaichi et al. |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,694,865 B2 | 4/2010 | Scirica |
| 7,695,485 B2 | 4/2010 | Whitman et al. |
| 7,699,204 B2 | 4/2010 | Viola |
| 7,699,846 B2 | 4/2010 | Ryan |
| 7,699,856 B2 | 4/2010 | Van Wyk et al. |
| 7,703,653 B2 | 4/2010 | Shah et al. |
| 7,708,180 B2 | 5/2010 | Murray et al. |
| 7,708,181 B2 | 5/2010 | Cole et al. |
| 7,708,182 B2 | 5/2010 | Viola |
| 7,708,758 B2 | 5/2010 | Lee et al. |
| 7,717,312 B2 | 5/2010 | Beetel |
| 7,717,313 B2 | 5/2010 | Criscuolo et al. |
| 7,717,846 B2 | 5/2010 | Zirps et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,731,073 B2 | 6/2010 | Wixey et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,627 B2 | 6/2010 | Orban, III et al. |
| 7,744,628 B2 | 6/2010 | Viola |
| 7,751,870 B2 | 7/2010 | Whitman |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,209 B2 | 8/2010 | Baxter, III et al. |
| 7,766,210 B2 | 8/2010 | Shelton, IV et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,780,054 B2 | 8/2010 | Wales |
| 7,780,055 B2 | 8/2010 | Scirica et al. |
| 7,784,662 B2 | 8/2010 | Wales et al. |
| 7,784,663 B2 | 8/2010 | Shelton, IV |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,823,592 B2 | 11/2010 | Bettuchi et al. |
| 7,824,426 B2 | 11/2010 | Racenet et al. |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,694 B2 | 11/2010 | Tethrake et al. |
| 7,842,028 B2 | 11/2010 | Lee |
| 7,845,533 B2 | 12/2010 | Marczyk et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,854,736 B2 | 12/2010 | Ryan |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,525 B2 | 1/2011 | Scirica |
| 7,866,527 B2 | 1/2011 | Hall et al. |
| 7,870,989 B2 | 1/2011 | Viola et al. |
| 7,886,951 B2 | 2/2011 | Hessler |
| 7,886,952 B2 | 2/2011 | Scirica et al. |
| 7,891,531 B1 | 2/2011 | Ward |
| 7,891,532 B2 | 2/2011 | Mastri et al. |
| 7,893,586 B2 | 2/2011 | West et al. |
| 7,896,877 B2 | 3/2011 | Hall et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,902 B2 | 3/2011 | Huitema et al. |
| 7,909,039 B2 | 3/2011 | Hur |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,918,376 B1 | 4/2011 | Knodel et al. |
| 7,918,377 B2 | 4/2011 | Measamer et al. |
| 7,918,845 B2 | 4/2011 | Saadat et al. |
| 7,922,061 B2 | 4/2011 | Shelton, IV et al. |
| 7,922,063 B2 | 4/2011 | Zemlok et al. |
| 7,922,743 B2 | 4/2011 | Heinrich et al. |
| 7,926,691 B2 | 4/2011 | Viola et al. |
| 7,931,660 B2 | 4/2011 | Aranyi et al. |
| 7,934,630 B2 | 5/2011 | Shelton, IV et al. |
| 7,934,631 B2 | 5/2011 | Balbierz et al. |
| 7,935,773 B2 | 5/2011 | Hadba et al. |
| 7,938,307 B2 | 5/2011 | Bettuchi |
| 7,942,303 B2 | 5/2011 | Shah |
| 7,942,890 B2 | 5/2011 | D'Agostino et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |
| 7,959,050 B2 | 6/2011 | Smith et al. |
| 7,959,051 B2 | 6/2011 | Smith et al. |
| 7,963,432 B2 | 6/2011 | Knodel et al. |
| 7,966,799 B2 | 6/2011 | Morgan et al. |
| 7,967,180 B2 | 6/2011 | Scirica |
| 7,967,181 B2 | 6/2011 | Viola et al. |
| 7,967,839 B2 | 6/2011 | Flock et al. |
| 7,976,563 B2 | 7/2011 | Summerer |
| 7,980,443 B2 | 7/2011 | Scheib et al. |
| 7,988,026 B2 | 8/2011 | Knodel et al. |
| 7,988,027 B2 | 8/2011 | Olson et al. |

(56) References Cited

U.S. PATENT DOCUMENTS

| | | |
|---|---|---|
| 7,988,779 B2 | 8/2011 | Disalvo et al. |
| 7,992,757 B2 | 8/2011 | Wheeler et al. |
| 7,997,469 B2 | 8/2011 | Olson et al. |
| 8,002,795 B2 | 8/2011 | Beetel |
| 8,006,885 B2 | 8/2011 | Marczyk |
| 8,006,889 B2 | 8/2011 | Adams et al. |
| 8,011,550 B2 | 9/2011 | Aranyi et al. |
| 8,011,551 B2 | 9/2011 | Marczyk et al. |
| 8,011,553 B2 | 9/2011 | Mastri et al. |
| 8,016,176 B2 | 9/2011 | Kasvikis et al. |
| 8,016,177 B2 | 9/2011 | Bettuchi et al. |
| 8,016,178 B2 | 9/2011 | Olson et al. |
| 8,016,849 B2 | 9/2011 | Wenchell |
| 8,016,855 B2 | 9/2011 | Whitman et al. |
| 8,016,858 B2 | 9/2011 | Whitman |
| 8,020,742 B2 | 9/2011 | Marczyk |
| 8,020,743 B2 | 9/2011 | Shelton, IV |
| 8,025,199 B2 | 9/2011 | Whitman et al. |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,034,077 B2 | 10/2011 | Smith et al. |
| 8,035,487 B2 | 10/2011 | Malackowski |
| 8,038,045 B2 | 10/2011 | Bettuchi et al. |
| 8,047,236 B2 | 11/2011 | Perry |
| 8,056,787 B2 | 11/2011 | Boudreaux et al. |
| 8,056,788 B2 | 11/2011 | Mastri et al. |
| 8,061,576 B2 | 11/2011 | Cappola |
| 8,062,330 B2 | 11/2011 | Prommersberger et al. |
| 8,066,167 B2 | 11/2011 | Measamer et al. |
| 8,066,168 B2 | 11/2011 | Vidal et al. |
| D650,074 S | 12/2011 | Hunt et al. |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,091,756 B2 | 1/2012 | Viola |
| 8,092,932 B2 | 1/2012 | Phillips et al. |
| 8,096,458 B2 | 1/2012 | Hessler |
| 8,097,017 B2 | 1/2012 | Viola |
| 8,100,310 B2 | 1/2012 | Zemlok |
| 8,105,350 B2 | 1/2012 | Lee et al. |
| 8,109,426 B2 | 2/2012 | Milliman et al. |
| 8,113,405 B2 | 2/2012 | Milliman |
| 8,113,410 B2 | 2/2012 | Hall et al. |
| 8,114,100 B2 | 2/2012 | Smith et al. |
| 8,123,103 B2 | 2/2012 | Milliman |
| 8,127,975 B2 | 3/2012 | Olson et al. |
| 8,132,703 B2 | 3/2012 | Milliman et al. |
| 8,132,706 B2 | 3/2012 | Marczyk et al. |
| 8,136,712 B2 | 3/2012 | Zingman |
| 8,140,417 B2 | 3/2012 | Shibata |
| 8,141,762 B2 | 3/2012 | Bedi et al. |
| 8,146,790 B2 | 4/2012 | Milliman |
| 8,152,041 B2 | 4/2012 | Kostrzewski |
| 8,157,145 B2 | 4/2012 | Shelton, IV et al. |
| 8,157,148 B2 | 4/2012 | Scirica |
| 8,157,152 B2 | 4/2012 | Holsten et al. |
| 8,157,153 B2 | 4/2012 | Shelton, IV et al. |
| 8,161,977 B2 | 4/2012 | Shelton, IV et al. |
| 8,162,197 B2 | 4/2012 | Mastri et al. |
| 8,162,933 B2 | 4/2012 | Francischelli et al. |
| 8,167,185 B2 | 5/2012 | Shelton, IV et al. |
| 8,172,120 B2 | 5/2012 | Boyden et al. |
| 8,172,122 B2 | 5/2012 | Kasvikis et al. |
| 8,172,124 B2 | 5/2012 | Shelton, IV et al. |
| 8,177,797 B2 | 5/2012 | Shimoji et al. |
| 8,186,555 B2 | 5/2012 | Shelton, IV et al. |
| 8,186,560 B2 | 5/2012 | Hess et al. |
| 8,191,752 B2 | 6/2012 | Scirica |
| 8,196,795 B2 | 6/2012 | Moore et al. |
| 8,196,796 B2 | 6/2012 | Shelton, IV et al. |
| 8,201,720 B2 | 6/2012 | Hessler |
| 8,201,721 B2 | 6/2012 | Zemlok et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,414 B2 | 7/2012 | Bettuchi et al. |
| 8,214,019 B2 | 7/2012 | Govari et al. |
| 8,215,531 B2 | 7/2012 | Shelton, IV et al. |
| 8,220,688 B2 | 7/2012 | Laurent et al. |
| 8,220,690 B2 | 7/2012 | Hess et al. |
| 8,231,040 B2 | 7/2012 | Zemlok et al. |
| 8,236,010 B2 | 8/2012 | Ortiz et al. |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,245,901 B2 | 8/2012 | Stopek |
| 8,246,637 B2 | 8/2012 | Viola et al. |
| 8,256,654 B2 | 9/2012 | Bettuchi et al. |
| 8,256,655 B2 | 9/2012 | Sniffin et al. |
| 8,267,300 B2 | 9/2012 | Boudreaux |
| 8,272,553 B2 | 9/2012 | Mastri et al. |
| 8,276,801 B2 | 10/2012 | Zemlok et al. |
| 8,286,845 B2 | 10/2012 | Perry et al. |
| 8,286,846 B2 | 10/2012 | Smith et al. |
| 8,292,151 B2 | 10/2012 | Viola |
| 8,292,155 B2 | 10/2012 | Shelton, IV et al. |
| 8,292,888 B2 | 10/2012 | Whitman |
| 8,308,040 B2 | 11/2012 | Huang et al. |
| 8,308,042 B2 | 11/2012 | Aranyi |
| 8,313,496 B2 | 11/2012 | Sauer et al. |
| 8,317,070 B2 | 11/2012 | Hueil et al. |
| 8,317,071 B1 | 11/2012 | Knodel |
| 8,317,074 B2 | 11/2012 | Ortiz et al. |
| 8,322,455 B2 | 12/2012 | Shelton, IV et al. |
| 8,322,589 B2 | 12/2012 | Boudreaux |
| 8,333,313 B2 | 12/2012 | Boudreaux et al. |
| 8,333,764 B2 | 12/2012 | Francischelli et al. |
| 8,336,753 B2 | 12/2012 | Olson et al. |
| 8,348,123 B2 | 1/2013 | Scirica et al. |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,377,029 B2 | 2/2013 | Nagao et al. |
| 8,393,513 B2 | 3/2013 | Jankowski |
| 8,393,514 B2 | 3/2013 | Shelton, IV et al. |
| 8,397,971 B2 | 3/2013 | Yates et al. |
| 8,403,945 B2 | 3/2013 | Whitfield et al. |
| 8,408,439 B2 | 4/2013 | Huang et al. |
| 8,413,870 B2 | 4/2013 | Pastorelli et al. |
| 8,414,577 B2 | 4/2013 | Boudreaux et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | McGuckin, Jr. et al. |
| 8,439,246 B1 | 5/2013 | Knodel |
| 8,444,036 B2 | 5/2013 | Shelton, IV |
| 8,453,904 B2 | 6/2013 | Eskaros et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,973 B2 | 6/2013 | Meade et al. |
| 8,470,355 B2 | 6/2013 | Skalla et al. |
| 8,474,677 B2 | 7/2013 | Woodard, Jr. et al. |

(56) References Cited

U.S. PATENT DOCUMENTS

| | | |
|---|---|---|
| 8,475,454 B1 | 7/2013 | Alshemari |
| 8,479,969 B2 | 7/2013 | Shelton, IV |
| 8,485,412 B2 | 7/2013 | Shelton, IV et al. |
| 8,485,413 B2 | 7/2013 | Scheib et al. |
| 8,496,156 B2 | 7/2013 | Sniffin et al. |
| 8,499,993 B2 | 8/2013 | Shelton, IV et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,043 B2 | 9/2013 | Ullrich et al. |
| 8,529,600 B2 | 9/2013 | Woodard, Jr. et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,550,984 B2 | 10/2013 | Takemoto |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,567,656 B2 | 10/2013 | Shelton, IV et al. |
| 8,573,459 B2 | 11/2013 | Smith et al. |
| 8,573,461 B2 | 11/2013 | Shelton, IV et al. |
| 8,573,465 B2 | 11/2013 | Shelton, IV |
| 8,579,176 B2 | 11/2013 | Smith et al. |
| 8,579,937 B2 | 11/2013 | Gresham |
| 8,584,919 B2 | 11/2013 | Hueil et al. |
| 8,590,760 B2 | 11/2013 | Cummins et al. |
| 8,590,762 B2 | 11/2013 | Hess et al. |
| 8,602,287 B2 | 12/2013 | Yates et al. |
| 8,602,288 B2 | 12/2013 | Shelton, IV et al. |
| 8,608,043 B2 | 12/2013 | Scirica |
| 8,608,044 B2 | 12/2013 | Hueil et al. |
| 8,608,045 B2 | 12/2013 | Smith et al. |
| 8,608,046 B2 | 12/2013 | Laurent et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,627,993 B2 | 1/2014 | Smith et al. |
| 8,631,987 B2 | 1/2014 | Shelton, IV et al. |
| 8,631,993 B2 | 1/2014 | Kostrzewski |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,191 B2 | 1/2014 | Meagher |
| 8,636,736 B2 | 1/2014 | Yates et al. |
| 8,652,120 B2 | 2/2014 | Giordano et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,672,209 B2 | 3/2014 | Crainich |
| 8,672,951 B2 | 3/2014 | Smith et al. |
| 8,678,263 B2 | 3/2014 | Viola |
| 8,679,154 B2 | 3/2014 | Smith et al. |
| 8,679,156 B2 | 3/2014 | Smith et al. |
| 8,684,253 B2 | 4/2014 | Giordano et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,708,210 B2 | 4/2014 | Zemlok et al. |
| 8,708,213 B2 | 4/2014 | Shelton, IV et al. |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,199 B2 | 5/2014 | Wenchell |
| 8,733,612 B2 | 5/2014 | Ma |
| 8,733,613 B2 | 5/2014 | Huitema et al. |
| 8,734,478 B2 | 5/2014 | Widenhouse et al. |
| 8,740,034 B2 | 6/2014 | Morgan et al. |
| 8,740,037 B2 | 6/2014 | Shelton, IV et al. |
| 8,740,038 B2 | 6/2014 | Shelton, IV et al. |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,747,238 B2 | 6/2014 | Shelton, IV et al. |
| 8,752,699 B2 | 6/2014 | Morgan et al. |
| 8,752,747 B2 | 6/2014 | Shelton, IV et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,875 B2 | 7/2014 | Morgan et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,770,459 B2 | 7/2014 | Racenet et al. |
| 8,777,004 B2 | 7/2014 | Shelton, IV et al. |
| 8,783,541 B2 | 7/2014 | Shelton, IV et al. |
| 8,783,542 B2 | 7/2014 | Riestenberg et al. |
| 8,783,543 B2 | 7/2014 | Shelton, IV et al. |
| 8,789,737 B2 | 7/2014 | Hodgkinson et al. |
| 8,789,739 B2 | 7/2014 | Swensgard |
| 8,789,740 B2 | 7/2014 | Baxter, III et al. |
| 8,789,741 B2 | 7/2014 | Baxter, III et al. |
| 8,794,497 B2 | 8/2014 | Zingman |
| 8,795,308 B2 | 8/2014 | Valin |
| 8,800,837 B2 | 8/2014 | Zemlok |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,801,752 B2 | 8/2014 | Fortier et al. |
| 8,806,973 B2 | 8/2014 | Ross et al. |
| 8,808,311 B2 | 8/2014 | Heinrich et al. |
| 8,808,325 B2 | 8/2014 | Hess et al. |
| 8,814,024 B2 | 8/2014 | Woodard, Jr. et al. |
| 8,820,603 B2 | 9/2014 | Shelton, IV et al. |
| 8,820,605 B2 | 9/2014 | Shelton, IV |
| 8,827,133 B2 | 9/2014 | Shelton, IV et al. |
| 8,827,134 B2 | 9/2014 | Viola et al. |
| 8,827,903 B2 | 9/2014 | Shelton, IV et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,857,693 B2 | 10/2014 | Schuckmann et al. |
| 8,857,694 B2 | 10/2014 | Shelton, IV et al. |
| 8,858,538 B2 | 10/2014 | Belson et al. |
| 8,858,571 B2 | 10/2014 | Shelton, IV et al. |
| 8,858,590 B2 | 10/2014 | Shelton, IV et al. |
| 8,864,007 B2 | 10/2014 | Widenhouse et al. |
| 8,864,009 B2 | 10/2014 | Shelton, IV et al. |
| 8,875,971 B2 | 11/2014 | Hall et al. |
| 8,875,972 B2 | 11/2014 | Weisenburgh, II et al. |
| 8,876,857 B2 | 11/2014 | Burbank |
| 8,893,946 B2 | 11/2014 | Boudreaux et al. |
| 8,893,949 B2 | 11/2014 | Shelton, IV et al. |
| 8,899,463 B2 | 12/2014 | Schall et al. |
| 8,899,465 B2 | 12/2014 | Shelton, IV et al. |
| 8,899,466 B2 | 12/2014 | Baxter, III et al. |
| 8,905,977 B2 | 12/2014 | Shelton et al. |
| 8,911,471 B2 | 12/2014 | Spivey et al. |
| 8,920,435 B2 | 12/2014 | Smith et al. |
| 8,920,443 B2 | 12/2014 | Hiles et al. |
| 8,925,782 B2 | 1/2015 | Shelton, IV |
| 8,925,788 B2 | 1/2015 | Hess et al. |
| 8,926,598 B2 | 1/2015 | Mollere et al. |
| 8,931,682 B2 | 1/2015 | Timm et al. |
| 8,945,163 B2 | 2/2015 | Voegele et al. |
| 8,956,390 B2 | 2/2015 | Shah et al. |
| 8,967,448 B2 | 3/2015 | Carter et al. |
| 8,968,310 B2 | 3/2015 | Twomey et al. |
| 8,973,803 B2 | 3/2015 | Hall et al. |
| 8,973,804 B2 | 3/2015 | Hess et al. |

(56) References Cited

U.S. PATENT DOCUMENTS

| | | |
|---|---|---|
| 8,974,440 B2 | 3/2015 | Farritor et al. |
| 8,978,954 B2 | 3/2015 | Shelton, IV et al. |
| 8,978,955 B2 | 3/2015 | Aronhalt et al. |
| 8,978,956 B2 | 3/2015 | Schall et al. |
| 8,991,676 B2 | 3/2015 | Hess et al. |
| 8,991,677 B2 | 3/2015 | Moore et al. |
| 8,992,422 B2 | 3/2015 | Spivey et al. |
| 8,998,058 B2 | 4/2015 | Moore et al. |
| 9,005,230 B2 | 4/2015 | Yates et al. |
| 9,005,238 B2 | 4/2015 | DeSantis et al. |
| 9,005,243 B2 | 4/2015 | Stopek et al. |
| 9,010,608 B2 | 4/2015 | Casasanta, Jr. et al. |
| 9,016,542 B2 | 4/2015 | Shelton, IV et al. |
| 9,028,494 B2 | 5/2015 | Shelton, IV et al. |
| 9,028,495 B2 | 5/2015 | Mueller et al. |
| 9,028,519 B2 | 5/2015 | Yates et al. |
| 9,033,203 B2 | 5/2015 | Woodard, Jr. et al. |
| 9,033,204 B2 | 5/2015 | Shelton, IV et al. |
| 9,044,227 B2 | 6/2015 | Shelton, IV et al. |
| 9,044,228 B2 | 6/2015 | Woodard, Jr. et al. |
| 9,044,229 B2 | 6/2015 | Scheib et al. |
| 9,044,230 B2 | 6/2015 | Morgan et al. |
| 9,050,083 B2 | 6/2015 | Yates et al. |
| 9,050,084 B2 | 6/2015 | Schmid et al. |
| 9,055,941 B2 | 6/2015 | Schmid et al. |
| 9,055,944 B2 | 6/2015 | Hodgkinson et al. |
| 9,060,770 B2 | 6/2015 | Shelton, IV et al. |
| 9,060,894 B2 | 6/2015 | Wubbeling |
| 9,072,515 B2 | 7/2015 | Hall et al. |
| 9,072,535 B2 | 7/2015 | Shelton, IV et al. |
| 9,072,536 B2 | 7/2015 | Shelton, IV et al. |
| 9,078,653 B2 * | 7/2015 | Leimbach ........ A61B 17/07207 |
| 9,084,601 B2 | 7/2015 | Moore et al. |
| 9,084,602 B2 | 7/2015 | Gleiman |
| 9,089,326 B2 | 7/2015 | Krumanaker et al. |
| 9,089,330 B2 | 7/2015 | Widenhouse et al. |
| 9,089,352 B2 | 7/2015 | Jeong |
| 9,095,339 B2 | 8/2015 | Moore et al. |
| 9,095,362 B2 | 8/2015 | Dachs, II et al. |
| 9,101,358 B2 | 8/2015 | Kerr et al. |
| 9,101,385 B2 | 8/2015 | Shelton, IV et al. |
| 9,107,663 B2 | 8/2015 | Swensgard |
| 9,113,862 B2 | 8/2015 | Morgan et al. |
| 9,113,864 B2 | 8/2015 | Morgan et al. |
| 9,113,865 B2 | 8/2015 | Shelton, IV et al. |
| 9,113,874 B2 | 8/2015 | Shelton, IV et al. |
| 9,113,880 B2 | 8/2015 | Zemlok et al. |
| 9,113,883 B2 | 8/2015 | Aronhalt et al. |
| 9,113,884 B2 | 8/2015 | Shelton, IV et al. |
| 9,119,657 B2 | 9/2015 | Shelton, IV et al. |
| 9,125,654 B2 | 9/2015 | Aronhalt et al. |
| 9,125,662 B2 | 9/2015 | Shelton, IV |
| 9,131,940 B2 | 9/2015 | Huitema et al. |
| 9,138,225 B2 | 9/2015 | Huang et al. |
| 9,149,274 B2 | 10/2015 | Spivey et al. |
| 9,168,038 B2 | 10/2015 | Shelton, IV et al. |
| 9,179,911 B2 | 11/2015 | Morgan et al. |
| 9,179,912 B2 | 11/2015 | Yates et al. |
| 9,186,143 B2 | 11/2015 | Timm et al. |
| 9,198,661 B2 | 12/2015 | Swensgard |
| 9,198,662 B2 | 12/2015 | Barton et al. |
| 9,204,878 B2 | 12/2015 | Hall et al. |
| 9,204,879 B2 | 12/2015 | Shelton, IV |
| 9,204,880 B2 | 12/2015 | Baxter, III et al. |
| 9,211,120 B2 | 12/2015 | Scheib et al. |
| 9,211,122 B2 | 12/2015 | Hagerty et al. |
| 9,216,019 B2 | 12/2015 | Schmid et al. |
| 9,220,500 B2 | 12/2015 | Swayze et al. |
| 9,220,501 B2 | 12/2015 | Baxter, III et al. |
| 9,226,751 B2 | 1/2016 | Shelton, IV et al. |
| 9,232,941 B2 | 1/2016 | Mandakolathur Vasudevan et al. |
| 9,232,945 B2 | 1/2016 | Zingman |
| 9,237,891 B2 | 1/2016 | Shelton, IV |
| 9,241,714 B2 | 1/2016 | Timm et al. |
| 9,271,799 B2 | 3/2016 | Shelton, IV et al. |
| 9,272,406 B2 | 3/2016 | Aronhalt et al. |
| 9,277,919 B2 | 3/2016 | Timmer et al. |
| 9,282,962 B2 | 3/2016 | Schmid et al. |
| 9,282,966 B2 | 3/2016 | Shelton, IV et al. |
| 9,282,974 B2 | 3/2016 | Shelton, IV |
| 9,289,210 B2 | 3/2016 | Baxter, III et al. |
| 9,289,212 B2 | 3/2016 | Shelton, IV et al. |
| 9,289,225 B2 | 3/2016 | Shelton, IV et al. |
| 9,289,256 B2 | 3/2016 | Shelton, IV et al. |
| 9,295,464 B2 | 3/2016 | Shelton, IV et al. |
| 9,301,752 B2 | 4/2016 | Mandakolathur Vasudevan et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,307,965 B2 | 4/2016 | Ming et al. |
| 9,307,986 B2 | 4/2016 | Hall et al. |
| 9,307,988 B2 | 4/2016 | Shelton, IV |
| 9,307,989 B2 | 4/2016 | Shelton, IV et al. |
| 9,314,246 B2 | 4/2016 | Shelton, IV et al. |
| 9,314,247 B2 | 4/2016 | Shelton, IV et al. |
| 9,320,518 B2 | 4/2016 | Henderson et al. |
| 9,320,521 B2 | 4/2016 | Shelton, IV et al. |
| 9,320,523 B2 | 4/2016 | Shelton, IV et al. |
| 9,326,767 B2 | 5/2016 | Koch et al. |
| 9,326,768 B2 | 5/2016 | Shelton, IV |
| 9,326,769 B2 | 5/2016 | Shelton, IV et al. |
| 9,326,770 B2 | 5/2016 | Shelton, IV et al. |
| 9,326,771 B2 | 5/2016 | Baxter, III et al. |
| 9,332,974 B2 | 5/2016 | Henderson et al. |
| 9,332,984 B2 | 5/2016 | Weaner et al. |
| 9,332,987 B2 | 5/2016 | Leimbach et al. |
| 9,345,477 B2 | 5/2016 | Anim et al. |
| 9,345,481 B2 | 5/2016 | Hall et al. |
| 9,351,726 B2 | 5/2016 | Leimbach et al. |
| 9,351,727 B2 | 5/2016 | Leimbach et al. |
| 9,351,730 B2 | 5/2016 | Schmid et al. |
| 9,358,003 B2 | 6/2016 | Hall et al. |
| 9,364,219 B2 | 6/2016 | Olson et al. |
| 9,364,230 B2 | 6/2016 | Shelton, IV et al. |
| 9,364,233 B2 | 6/2016 | Alexander, III et al. |
| 9,370,358 B2 | 6/2016 | Shelton, IV et al. |
| 9,370,364 B2 | 6/2016 | Smith et al. |
| 9,386,983 B2 | 7/2016 | Swensgard et al. |
| 9,386,984 B2 | 7/2016 | Aronhalt et al. |
| 9,386,988 B2 | 7/2016 | Baxter, III et al. |
| 9,393,015 B2 | 7/2016 | Laurent et al. |
| 9,398,911 B2 | 7/2016 | Auld |
| 9,402,626 B2 | 8/2016 | Ortiz et al. |
| 9,408,604 B2 | 8/2016 | Shelton, IV et al. |
| 9,408,606 B2 | 8/2016 | Shelton, IV |
| 9,414,838 B2 | 8/2016 | Shelton, IV et al. |
| 9,427,223 B2 | 8/2016 | Park et al. |
| 9,433,419 B2 | 9/2016 | Gonzalez et al. |
| 9,439,649 B2 | 9/2016 | Shelton, IV et al. |
| 9,439,651 B2 | 9/2016 | Smith et al. |
| 9,451,958 B2 | 9/2016 | Shelton, IV et al. |
| 9,463,260 B2 | 10/2016 | Stopek |
| 9,468,438 B2 | 10/2016 | Baber et al. |
| 9,480,476 B2 | 11/2016 | Aldridge et al. |
| 9,486,213 B2 | 11/2016 | Altman et al. |
| 9,486,214 B2 | 11/2016 | Shelton, IV |
| 9,492,167 B2 | 11/2016 | Shelton, IV et al. |
| 9,492,170 B2 | 11/2016 | Bear et al. |
| 9,510,925 B2 | 12/2016 | Hotter et al. |
| 9,517,063 B2 | 12/2016 | Swayze et al. |
| 9,517,068 B2 | 12/2016 | Shelton, IV et al. |
| 9,522,029 B2 | 12/2016 | Yates et al. |
| 9,549,732 B2 | 1/2017 | Yates et al. |
| 9,554,794 B2 | 1/2017 | Baber et al. |
| 9,561,032 B2 | 2/2017 | Shelton, IV et al. |
| 9,561,038 B2 | 2/2017 | Shelton, IV et al. |
| 9,566,061 B2 | 2/2017 | Aronhalt et al. |
| 9,572,577 B2 | 2/2017 | Lloyd et al. |
| 9,574,644 B2 | 2/2017 | Parihar |
| 9,585,657 B2 | 3/2017 | Shelton, IV et al. |
| 9,585,660 B2 | 3/2017 | Laurent et al. |
| 9,592,050 B2 | 3/2017 | Schmid et al. |
| 9,592,052 B2 | 3/2017 | Shelton, IV |
| 9,592,053 B2 | 3/2017 | Shelton, IV et al. |

(56) References Cited

U.S. PATENT DOCUMENTS

| | | |
|---|---|---|
| 9,592,054 B2 | 3/2017 | Schmid et al. |
| 9,597,075 B2 | 3/2017 | Shelton, IV et al. |
| 9,597,080 B2 | 3/2017 | Milliman et al. |
| 9,603,595 B2 | 3/2017 | Shelton, IV et al. |
| 9,603,598 B2 | 3/2017 | Shelton, IV et al. |
| 9,603,991 B2 | 3/2017 | Shelton, IV et al. |
| 9,615,826 B2 | 4/2017 | Shelton, IV et al. |
| 9,629,623 B2 | 4/2017 | Lytle, IV et al. |
| 9,629,626 B2 | 4/2017 | Soltz et al. |
| 9,629,629 B2 | 4/2017 | Leimbach et al. |
| 9,629,814 B2 | 4/2017 | Widenhouse et al. |
| 9,642,620 B2 | 5/2017 | Baxter, III et al. |
| 9,649,110 B2 | 5/2017 | Parihar et al. |
| 9,649,111 B2 | 5/2017 | Shelton, IV et al. |
| 9,655,614 B2 | 5/2017 | Swensgard et al. |
| 9,655,624 B2 | 5/2017 | Shelton, IV et al. |
| 9,675,355 B2 | 6/2017 | Shelton, IV et al. |
| 9,675,372 B2 | 6/2017 | Laurent et al. |
| 9,675,375 B2 | 6/2017 | Houser et al. |
| 9,681,873 B2 | 6/2017 | Smith et al. |
| 9,687,230 B2 | 6/2017 | Leimbach et al. |
| 9,687,231 B2 | 6/2017 | Baxter, III et al. |
| 9,687,236 B2 | 6/2017 | Leimbach et al. |
| 9,700,309 B2 | 7/2017 | Jaworek et al. |
| 9,700,315 B2 | 7/2017 | Chen et al. |
| 9,700,317 B2 | 7/2017 | Aronhalt et al. |
| 9,700,321 B2 | 7/2017 | Shelton, IV et al. |
| 9,706,991 B2 | 7/2017 | Hess et al. |
| 9,724,091 B2 | 8/2017 | Shelton, IV et al. |
| 9,730,692 B2 | 8/2017 | Shelton, IV et al. |
| 9,743,928 B2 | 8/2017 | Shelton, IV et al. |
| 9,757,123 B2 | 9/2017 | Giordano et al. |
| 9,757,130 B2 | 9/2017 | Shelton, IV |
| 9,770,245 B2 | 9/2017 | Swayze et al. |
| 9,775,613 B2 | 10/2017 | Shelton, IV et al. |
| 9,782,169 B2 | 10/2017 | Kimsey et al. |
| 9,788,834 B2 | 10/2017 | Schmid et al. |
| 9,795,382 B2 | 10/2017 | Shelton, IV |
| 9,795,384 B2 | 10/2017 | Weaner et al. |
| 9,801,626 B2 | 10/2017 | Parihar et al. |
| 9,808,244 B2 | 11/2017 | Leimbach et al. |
| 9,814,460 B2 | 11/2017 | Kimsey et al. |
| 9,814,462 B2 | 11/2017 | Woodard, Jr. et al. |
| 9,826,976 B2 | 11/2017 | Parihar et al. |
| 9,833,236 B2 | 12/2017 | Shelton, IV et al. |
| 9,839,420 B2 | 12/2017 | Shelton, IV et al. |
| 9,839,427 B2 | 12/2017 | Swayze et al. |
| 9,844,368 B2 | 12/2017 | Boudreaux et al. |
| 9,844,373 B2 | 12/2017 | Swayze et al. |
| 9,848,873 B2 | 12/2017 | Shelton, IV |
| 9,848,875 B2 | 12/2017 | Aronhalt et al. |
| 9,848,877 B2 | 12/2017 | Shelton, IV et al. |
| 9,861,359 B2 | 1/2018 | Shelton, IV et al. |
| 9,861,361 B2 | 1/2018 | Aronhalt et al. |
| 9,867,612 B2 | 1/2018 | Parihar et al. |
| 9,883,860 B2 | 2/2018 | Leimbach |
| 9,888,919 B2 | 2/2018 | Leimbach et al. |
| 9,888,924 B2 | 2/2018 | Ebersole et al. |
| 9,980,630 B2 | 5/2018 | Larkin et al. |
| 9,999,408 B2 | 6/2018 | Boudreaux et al. |
| 10,004,498 B2 | 6/2018 | Morgan et al. |
| 10,010,322 B2 | 7/2018 | Shelton, IV et al. |
| 10,039,529 B2 | 8/2018 | Kerr et al. |
| 10,045,781 B2 | 8/2018 | Cropper et al. |
| 10,052,099 B2 | 8/2018 | Morgan et al. |
| 10,052,100 B2 | 8/2018 | Morgan et al. |
| 10,058,963 B2 | 8/2018 | Shelton, IV et al. |
| 10,071,452 B2 | 9/2018 | Shelton, IV et al. |
| 10,123,798 B2 | 11/2018 | Baxter, III et al. |
| 10,130,359 B2 | 11/2018 | Hess et al. |
| 10,136,887 B2 | 11/2018 | Shelton, IV et al. |
| 10,136,890 B2 | 11/2018 | Shelton, IV et al. |
| 10,149,680 B2 | 12/2018 | Parihar et al. |
| 10,159,482 B2 | 12/2018 | Swayze et al. |
| 10,166,025 B2 * | 1/2019 | Leimbach ............ A61B 17/072 |
| 10,188,393 B2 | 1/2019 | Smith et al. |
| 10,213,198 B2 | 2/2019 | Aronhalt et al. |
| 10,335,144 B2 | 7/2019 | Shelton, IV et al. |
| 10,342,533 B2 | 7/2019 | Shelton, IV et al. |
| 10,390,823 B2 | 8/2019 | Shelton, IV et al. |
| 10,405,854 B2 | 9/2019 | Schmid et al. |
| 10,405,857 B2 | 9/2019 | Shelton, IV et al. |
| 10,433,918 B2 | 10/2019 | Shelton, IV et al. |
| 10,441,369 B2 | 10/2019 | Shelton, IV et al. |
| 10,470,762 B2 | 11/2019 | Leimbach et al. |
| 10,492,787 B2 | 12/2019 | Smith et al. |
| 10,660,640 B2 | 5/2020 | Yates et al. |
| 10,729,441 B2 | 8/2020 | Cropper et al. |
| 10,736,629 B2 | 8/2020 | Shelton, IV et al. |
| 11,083,458 B2 | 8/2021 | Harris et al. |
| 2002/0117534 A1 | 8/2002 | Green et al. |
| 2003/0009193 A1 | 1/2003 | Corsaro |
| 2003/0039689 A1 | 2/2003 | Chen et al. |
| 2003/0096158 A1 | 5/2003 | Takano et al. |
| 2003/0181900 A1 | 9/2003 | Long |
| 2003/0236505 A1 | 12/2003 | Bonadio et al. |
| 2004/0068161 A1 | 4/2004 | Couvillon |
| 2004/0102783 A1 | 5/2004 | Sutterlin et al. |
| 2004/0108357 A1 | 6/2004 | Milliman et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0225186 A1 | 11/2004 | Horne et al. |
| 2004/0232201 A1 | 11/2004 | Wenchell et al. |
| 2004/0267310 A1 | 12/2004 | Racenet et al. |
| 2005/0059997 A1 | 3/2005 | Bauman et al. |
| 2005/0070929 A1 | 3/2005 | Dalessandro et al. |
| 2005/0080342 A1 | 4/2005 | Gilreath et al. |
| 2005/0125897 A1 | 6/2005 | Wyslucha et al. |
| 2005/0139636 A1 | 6/2005 | Schwemberger et al. |
| 2005/0143759 A1 | 6/2005 | Kelly |
| 2005/0216055 A1 | 9/2005 | Scirica et al. |
| 2005/0228224 A1 | 10/2005 | Okada et al. |
| 2005/0263563 A1 | 12/2005 | Racenet et al. |
| 2006/0049229 A1 | 3/2006 | Milliman et al. |
| 2006/0052825 A1 | 3/2006 | Ransick et al. |
| 2006/0089535 A1 | 4/2006 | Raz et al. |
| 2006/0173470 A1 | 8/2006 | Oray et al. |
| 2006/0180634 A1 | 8/2006 | Shelton et al. |
| 2006/0201989 A1 | 9/2006 | Ojeda |
| 2006/0235368 A1 | 10/2006 | Oz |
| 2006/0271102 A1 | 11/2006 | Bosshard et al. |
| 2006/0287576 A1 | 12/2006 | Tsuji et al. |
| 2006/0289602 A1 | 12/2006 | Wales et al. |
| 2006/0291981 A1 | 12/2006 | Viola et al. |
| 2007/0027468 A1 | 2/2007 | Wales et al. |
| 2007/0051375 A1 | 3/2007 | Milliman |
| 2007/0073341 A1 | 3/2007 | Smith et al. |
| 2007/0084896 A1 | 4/2007 | Doll et al. |
| 2007/0084897 A1 | 4/2007 | Shelton et al. |
| 2007/0093869 A1 | 4/2007 | Bloom et al. |
| 2007/0102472 A1 | 5/2007 | Shelton |
| 2007/0106317 A1 | 5/2007 | Shelton et al. |
| 2007/0134251 A1 | 6/2007 | Ashkenazi et al. |
| 2007/0170225 A1 | 7/2007 | Shelton et al. |
| 2007/0173687 A1 | 7/2007 | Shima et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0225562 A1 | 9/2007 | Spivey et al. |
| 2007/0246505 A1 | 10/2007 | Pace-Floridia et al. |
| 2007/0276409 A1 | 11/2007 | Ortiz et al. |
| 2007/0279011 A1 | 12/2007 | Jones et al. |
| 2008/0023522 A1 | 1/2008 | Olson et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0082125 A1 | 4/2008 | Murray et al. |
| 2008/0086078 A1 | 4/2008 | Powell et al. |

(56) References Cited

U.S. PATENT DOCUMENTS

| | | |
|---|---|---|
| 2008/0135600 A1 | 6/2008 | Hiranuma et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0190989 A1 | 8/2008 | Crews et al. |
| 2008/0197167 A1 | 8/2008 | Viola et al. |
| 2008/0200762 A1 | 8/2008 | Stokes et al. |
| 2008/0249536 A1 | 10/2008 | Stahler et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0005809 A1 | 1/2009 | Hess et al. |
| 2009/0078736 A1 | 3/2009 | Van Lue |
| 2009/0090763 A1 | 4/2009 | Zemlok et al. |
| 2009/0099876 A1 | 4/2009 | Whitman |
| 2009/0149871 A9 | 6/2009 | Kagan et al. |
| 2009/0188964 A1 | 7/2009 | Orlov |
| 2009/0204108 A1 | 8/2009 | Steffen |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0242610 A1 | 10/2009 | Shelton, IV et al. |
| 2009/0255974 A1 | 10/2009 | Viola |
| 2009/0261143 A1 | 10/2009 | Wixey et al. |
| 2009/0308907 A1 | 12/2009 | Nalagatla et al. |
| 2010/0069942 A1 | 3/2010 | Shelton, IV |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0193566 A1 | 8/2010 | Scheib et al. |
| 2010/0222901 A1 | 9/2010 | Swayze et al. |
| 2011/0006101 A1 | 1/2011 | Hall et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0060363 A1 | 3/2011 | Hess et al. |
| 2011/0087276 A1 | 4/2011 | Bedi et al. |
| 2011/0091515 A1 | 4/2011 | Zilberman et al. |
| 2011/0114697 A1 | 5/2011 | Baxter, III et al. |
| 2011/0125176 A1 | 5/2011 | Yates et al. |
| 2011/0147433 A1 | 6/2011 | Shelton, IV et al. |
| 2011/0163146 A1 | 7/2011 | Ortiz et al. |
| 2011/0174861 A1 | 7/2011 | Shelton, IV et al. |
| 2011/0192882 A1 | 8/2011 | Hess et al. |
| 2011/0204120 A1 | 8/2011 | Crainich |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0290856 A1 | 12/2011 | Shelton, IV et al. |
| 2011/0293690 A1 | 12/2011 | Griffin et al. |
| 2011/0295295 A1 | 12/2011 | Shelton, IV et al. |
| 2012/0029272 A1 | 2/2012 | Shelton, IV et al. |
| 2012/0074200 A1 | 3/2012 | Schmid et al. |
| 2012/0080336 A1 | 4/2012 | Shelton, IV et al. |
| 2012/0080344 A1 | 4/2012 | Shelton, IV |
| 2012/0080478 A1 | 4/2012 | Morgan et al. |
| 2012/0080498 A1 | 4/2012 | Shelton, IV et al. |
| 2012/0125792 A1 | 5/2012 | Cassivi |
| 2012/0175398 A1 | 7/2012 | Sandborn et al. |
| 2012/0234895 A1 | 9/2012 | O'Connor et al. |
| 2012/0234897 A1 | 9/2012 | Shelton, IV et al. |
| 2012/0248169 A1 | 10/2012 | Widenhouse et al. |
| 2012/0283707 A1 | 11/2012 | Giordano et al. |
| 2012/0292367 A1 | 11/2012 | Morgan et al. |
| 2012/0298722 A1 | 11/2012 | Hess et al. |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0087597 A1 | 4/2013 | Shelton, IV et al. |
| 2013/0116669 A1 | 5/2013 | Shelton, IV et al. |
| 2013/0153641 A1 | 6/2013 | Shelton, IV et al. |
| 2013/0175317 A1 | 7/2013 | Yates et al. |
| 2013/0233906 A1 | 9/2013 | Hess et al. |
| 2013/0256373 A1 | 10/2013 | Schmid et al. |
| 2013/0256380 A1 | 10/2013 | Schmid et al. |
| 2013/0270322 A1 | 10/2013 | Scheib et al. |
| 2013/0334283 A1 | 12/2013 | Swayze et al. |
| 2013/0334285 A1 | 12/2013 | Swayze et al. |
| 2013/0341374 A1 | 12/2013 | Shelton, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005678 A1 | 1/2014 | Shelton, IV et al. |
| 2014/0005718 A1 | 1/2014 | Shelton, IV et al. |
| 2014/0014705 A1 | 1/2014 | Baxter, III |
| 2014/0048580 A1 | 2/2014 | Merchant et al. |
| 2014/0151433 A1 | 6/2014 | Shelton, IV et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175152 A1 | 6/2014 | Hess et al. |
| 2014/0224857 A1 | 8/2014 | Schmid |
| 2014/0243865 A1 | 8/2014 | Swayze et al. |
| 2014/0246475 A1 | 9/2014 | Hall et al. |
| 2014/0249557 A1 | 9/2014 | Koch et al. |
| 2014/0263541 A1 | 9/2014 | Leimbach et al. |
| 2014/0263552 A1 | 9/2014 | Hall et al. |
| 2014/0284371 A1 | 9/2014 | Morgan et al. |
| 2014/0291379 A1 | 10/2014 | Schellin et al. |
| 2014/0291383 A1 | 10/2014 | Spivey et al. |
| 2014/0299648 A1 | 10/2014 | Shelton, IV et al. |
| 2014/0303645 A1 | 10/2014 | Morgan et al. |
| 2014/0330161 A1 | 11/2014 | Swayze et al. |
| 2015/0008248 A1 | 1/2015 | Giordano et al. |
| 2015/0173756 A1 | 6/2015 | Baxter, III et al. |
| 2016/0174969 A1 | 6/2016 | Kerr et al. |
| 2021/0007743 A1 | 1/2021 | Cropper et al. |
| 2022/0133299 A1 | 5/2022 | Baxter, III |
| 2022/0133300 A1 | 5/2022 | Leimbach et al. |

FOREIGN PATENT DOCUMENTS

| | | |
|---|---|---|
| CN | 1634601 A | 7/2005 |
| CN | 201949071 U | 8/2011 |
| DE | 273689 C | 5/1914 |
| DE | 1775926 A | 1/1972 |
| DE | 3036217 A1 | 4/1982 |
| DE | 3210466 A1 | 9/1983 |
| DE | 3709067 A1 | 9/1988 |
| DE | 19851291 A1 | 1/2000 |
| DE | 19924311 A1 | 11/2000 |
| DE | 20016423 U1 | 2/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0000756 A1 | 2/1979 |
| EP | 0122046 A1 | 10/1984 |
| EP | 0129442 B1 | 11/1987 |
| EP | 0169044 B1 | 6/1991 |
| EP | 0594148 A1 | 4/1994 |
| EP | 0646357 A1 | 4/1995 |
| EP | 0505036 B1 | 5/1995 |
| EP | 0669104 A1 | 8/1995 |
| EP | 0705571 A1 | 4/1996 |
| EP | 0528478 B1 | 5/1996 |
| EP | 0770355 A1 | 5/1997 |
| EP | 0625335 B1 | 11/1997 |
| EP | 0879742 A1 | 11/1998 |
| EP | 0650701 B1 | 3/1999 |
| EP | 0923907 A1 | 6/1999 |
| EP | 0484677 B2 | 7/2000 |
| EP | 1034747 A1 | 9/2000 |

(56) References Cited

FOREIGN PATENT DOCUMENTS

| | | | |
|---|---|---|---|
| EP | 1034748 A1 | 9/2000 |
| EP | 1053719 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 0806914 B1 | 9/2001 |
| EP | 1284120 A1 | 2/2003 |
| EP | 0869742 B1 | 5/2003 |
| EP | 1374788 A1 | 1/2004 |
| EP | 1407719 A2 | 4/2004 |
| EP | 0996378 B1 | 6/2004 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 1632191 A2 | 3/2006 |
| EP | 1082944 B1 | 5/2006 |
| EP | 1253866 B1 | 7/2006 |
| EP | 1285633 B1 | 12/2006 |
| EP | 1011494 B1 | 1/2007 |
| EP | 1767163 A1 | 3/2007 |
| EP | 1837041 A1 | 9/2007 |
| EP | 0922435 B1 | 10/2007 |
| EP | 1599146 B1 | 10/2007 |
| EP | 1330201 B1 | 6/2008 |
| EP | 2039302 A2 | 3/2009 |
| EP | 1719461 B1 | 6/2009 |
| EP | 1769754 B1 | 6/2010 |
| EP | 1627605 B1 | 12/2010 |
| EP | 2517638 A1 | 10/2012 |
| FR | 459743 A | 11/1913 |
| FR | 999646 A | 2/1952 |
| FR | 1112936 A | 3/1956 |
| FR | 2598905 A1 | 11/1987 |
| FR | 2765794 A1 | 1/1999 |
| FR | 2815842 A1 | 5/2002 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2336214 A | 10/1999 |
| GR | 930100110 A | 11/1993 |
| JP | S5033988 U | 4/1975 |
| JP | H0584252 A | 4/1993 |
| JP | H05-130998 A | 5/1993 |
| JP | H05-200038 A | 8/1993 |
| JP | H0630945 A | 2/1994 |
| JP | H06237937 A | 8/1994 |
| JP | H07124166 A | 5/1995 |
| JP | H07255735 A | 10/1995 |
| JP | H07285089 A | 10/1995 |
| JP | H0833642 A | 2/1996 |
| JP | H08164141 A | 6/1996 |
| JP | H08182684 A | 7/1996 |
| JP | H08507708 A | 8/1996 |
| JP | H08229050 A | 9/1996 |
| JP | H10118090 A | 5/1998 |
| JP | 2000014632 A | 1/2000 |
| JP | 2000033071 A | 2/2000 |
| JP | 2000112002 A | 4/2000 |
| JP | 2000166932 A | 6/2000 |
| JP | 2000171730 A | 6/2000 |
| JP | 2000287987 A | 10/2000 |
| JP | 2000325303 A | 11/2000 |
| JP | 2001087272 A | 4/2001 |
| JP | 2001514541 A | 9/2001 |
| JP | 2002051974 A | 2/2002 |
| JP | 2002143078 A | 5/2002 |
| JP | 2002528161 A | 9/2002 |
| JP | 2003135473 A | 5/2003 |
| JP | 2003521301 A | 7/2003 |
| JP | 2004147702 A | 5/2004 |
| JP | 2004162035 A | 6/2004 |
| JP | 2004229976 A | 8/2004 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005137423 A | 6/2005 |
| JP | 2005328882 A | 12/2005 |
| JP | 2005335432 A | 12/2005 |
| JP | 2005342267 A | 12/2005 |
| JP | 2006187649 A | 7/2006 |
| JP | 2006281405 A | 10/2006 |
| JP | 2006346445 A | 12/2006 |
| JP | 2009189838 A | 8/2009 |
| JP | 2009539420 A | 11/2009 |
| JP | 2010098844 A | 4/2010 |
| RU | 1814161 C | 5/1993 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2161450 C1 | 1/2001 |
| RU | 2181566 C2 | 4/2002 |
| RU | 2187249 C2 | 8/2002 |
| RU | 32984 U1 | 10/2003 |
| RU | 2225170 C2 | 3/2004 |
| RU | 42750 U1 | 12/2004 |
| RU | 61114 U1 | 2/2007 |
| RU | 61122 U1 | 2/2007 |
| SU | 189517 A | 1/1967 |
| SU | 328636 A | 9/1972 |
| SU | 674747 A1 | 7/1979 |
| SU | 1009439 A | 4/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO-9315648 A1 | 8/1993 |
| WO | WO-9420030 A1 | 9/1994 |
| WO | WO-9517855 A1 | 7/1995 |
| WO | WO-9520360 A1 | 8/1995 |
| WO | WO-9623448 A1 | 8/1996 |
| WO | WO-9635464 A1 | 11/1996 |
| WO | WO-9639086 A1 | 12/1996 |
| WO | WO-9639088 A1 | 12/1996 |
| WO | WO-9724073 A1 | 7/1997 |
| WO | WO-9734533 A1 | 9/1997 |
| WO | WO-9903407 A1 | 1/1999 |
| WO | WO-9903409 A1 | 1/1999 |
| WO | WO-9948430 A1 | 9/1999 |
| WO | WO-0024322 A1 | 5/2000 |
| WO | WO-0024330 A1 | 5/2000 |
| WO | WO-0053112 A2 | 9/2000 |
| WO | WO-0057796 A1 | 10/2000 |
| WO | WO-0105702 A1 | 1/2001 |
| WO | WO-0154594 A1 | 8/2001 |
| WO | WO-0158371 A1 | 8/2001 |
| WO | WO-0162164 A2 | 8/2001 |
| WO | WO-0162169 A2 | 8/2001 |
| WO | WO-0191646 A1 | 12/2001 |
| WO | WO-0219932 A1 | 3/2002 |
| WO | WO-0226143 A1 | 4/2002 |
| WO | WO-0236028 A1 | 5/2002 |
| WO | WO-03055402 A1 | 7/2003 |
| WO | WO-03094747 A1 | 11/2003 |
| WO | WO-03079909 A3 | 3/2004 |
| WO | WO-2004019803 A1 | 3/2004 |
| WO | WO-2004032783 A1 | 4/2004 |
| WO | WO-2004047626 A1 | 6/2004 |
| WO | WO-2004047653 A2 | 6/2004 |

(56) References Cited

FOREIGN PATENT DOCUMENTS

| WO | WO-2004056277 A1 | 7/2004 |
| WO | WO-2004078050 A2 | 9/2004 |
| WO | WO-2004078051 A2 | 9/2004 |
| WO | WO-2004096015 A2 | 11/2004 |
| WO | WO-2006044581 A2 | 4/2006 |
| WO | WO-2006051252 A1 | 5/2006 |
| WO | WO-2006059067 A1 | 6/2006 |
| WO | WO-2007137304 A2 | 11/2007 |
| WO | WO-2007142625 A2 | 12/2007 |
| WO | WO-2008021969 A2 | 2/2008 |
| WO | WO-2008089404 A2 | 7/2008 |
| WO | WO-2009067649 A2 | 5/2009 |
| WO | WO-2009091497 A2 | 7/2009 |
| WO | WO-2011008672 A2 | 1/2011 |
| WO | WO-2011044343 A2 | 4/2011 |
| WO | WO-2012044606 A2 | 4/2012 |
| WO | WO 2013/148253 A2 | 10/2013 |

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20., pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

Biomedical Coatings, Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld et al., "A New, Easily Miniaturized Sterrable Endoscope," IEEE Engineering in Medicine and Biology Magazine (Nov./Dec. 2005).

D. Tuite, Ed., "Get The Lowdown On Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

ASTM procedure D2240-00, "Standard Test Method for Rubber Property-Durometer Hardness," (Published Aug. 2000).

ASTM procedure D2240-05, "Standard Test Method for Rubber Property-Durometer Hardness," (Published Apr. 2010).

Covidien Brochure, "Endo GIA™ Reloads with Tri-Staple™ Technology," (2010), 1 page.

Covidien Brochure, "Endo GIA™ Reloads with Tri-Staple™ Technology and Endo GIA™ Ultra Universal Staplers," (2010), 2 pages.

Covidien Brochure, "Endo GIA™ Black Reload with Tri-Staple™ Technology," (2012), 2 pages.

Covidien Brochure, "Endo GIA™ Curved Tip Reload with Tri-Staple™ Technology," (2012), 2 pages.

Covidien Brochure, "Endo GIA™ Reloads with Tri-Staple™ Technology," (2010), 2 pages.

Covidien Brochure, "Endo GIA™ Ultra Universal Stapler," (2010), 2 pages.

Miyata et al., "Biomolecule-Sensitive Hydrogels," Advanced Drug Delivery Reviews, 54 (2002) pp. 79-98.

Jeong et al., "Thermosensitive Sol-Gel Reversible Hydrogels," Advanced Drug Delivery Reviews, 54 (2002) pp. 37-51.

Byrne et al., "Molecular Imprinting Within Hydrogels," Advanced Drug Delivery Reviews, 54 (2002) pp. 149-161.

Qiu et al., "Environment-Sensitive Hydrogels for Drug Delivery," Advanced Drug Delivery Reviews, 53 (2001) pp. 321-339.

Hoffman, "Hydrogels for Biomedical Applications," Advanced Drug Delivery Reviews, 43 (2002) pp. 3-12.

Hoffman, "Hydrogels for Biomedical Applications," Advanced Drug Delivery Reviews, 54 (2002) pp. 3-12.

Peppas, "Physiologically Responsive Hydrogels," Journal of Bioactive and Compatible Polymers, vol. 6 (Jul. 1991) pp. 241-246.

Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.

Peppas, Editor "Hydrogels in Medicine and Pharmacy," vol. I, Fundamentals, CRC Press, 1986.

Matsuda, "Thermodynamics of Formation of Porous Polymeric Membrane from Solutions," Polymer Journal, vol. 23, No. 5, pp. 435-444 (1991).

Young, "Microcellular foams via phase separation," Journal of Vacuum Science & Technology A 4(3), (May/Jun. 1986).

Chen et al., "Elastomeric Biomaterials for Tissue Engineering," Progress in Polymer Science 38 (2013), pp. 584-671.

Pitt et al., "Attachment of Hyaluronan to Metallic Surfaces," J. Biomed. Mater. Res. 68A: pp. 95-106, 2004.

Schellhammer et al., "Poly-Lactic-Acid for Coating of Endovascular Stents: Preliminary Results in Canine Experimental Av-Fistulae," Mat.-wiss. u. Werkstofftech., 32, pp. 193-199 (2001).

Solorio et al., "Gelatin Microspheres Crosslinked with Genipin for Local Delivery of Growth Factors," J. Tissue Eng. Regen. Med. (2010), 4(7): pp. 514-523.

The Sodem Aseptic Battery Transfer Kit, Sodem Systems, 2000, 3 pages.

Extended European Search Report dated Mar. 23, 2020, for Application No. 19219422.3, 8 pages.

Extended European Search Report dated Jul. 23, 2021, for Application No. 21171550.3, 12 pages.

Indian Office Action dated Jun. 16, 2020, for Application No. 7608/DELNP/2014, 5 pages.

International Search Report and Written Opinion dated Jan. 17, 2014, for International Application No. PCT/US2013/031423, 14 pages.

Japanese Notification of Reasons for Refusal dated Mar. 31, 2017, for Application No. 2015- 503303, 4 pages.

Russian Office Action dated Mar. 14, 2017, for Application No. 2014143016, 6 pages.

* cited by examiner

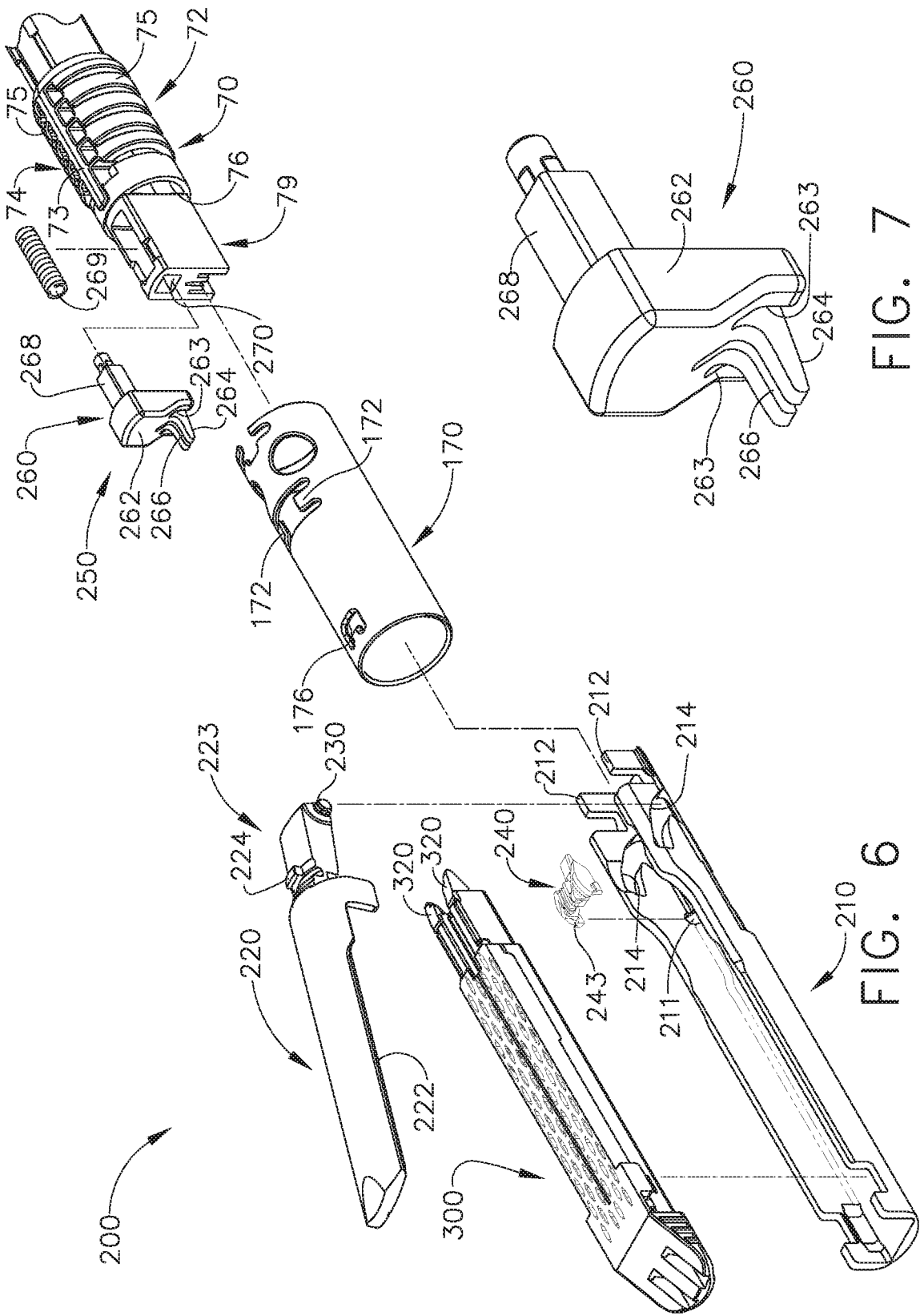

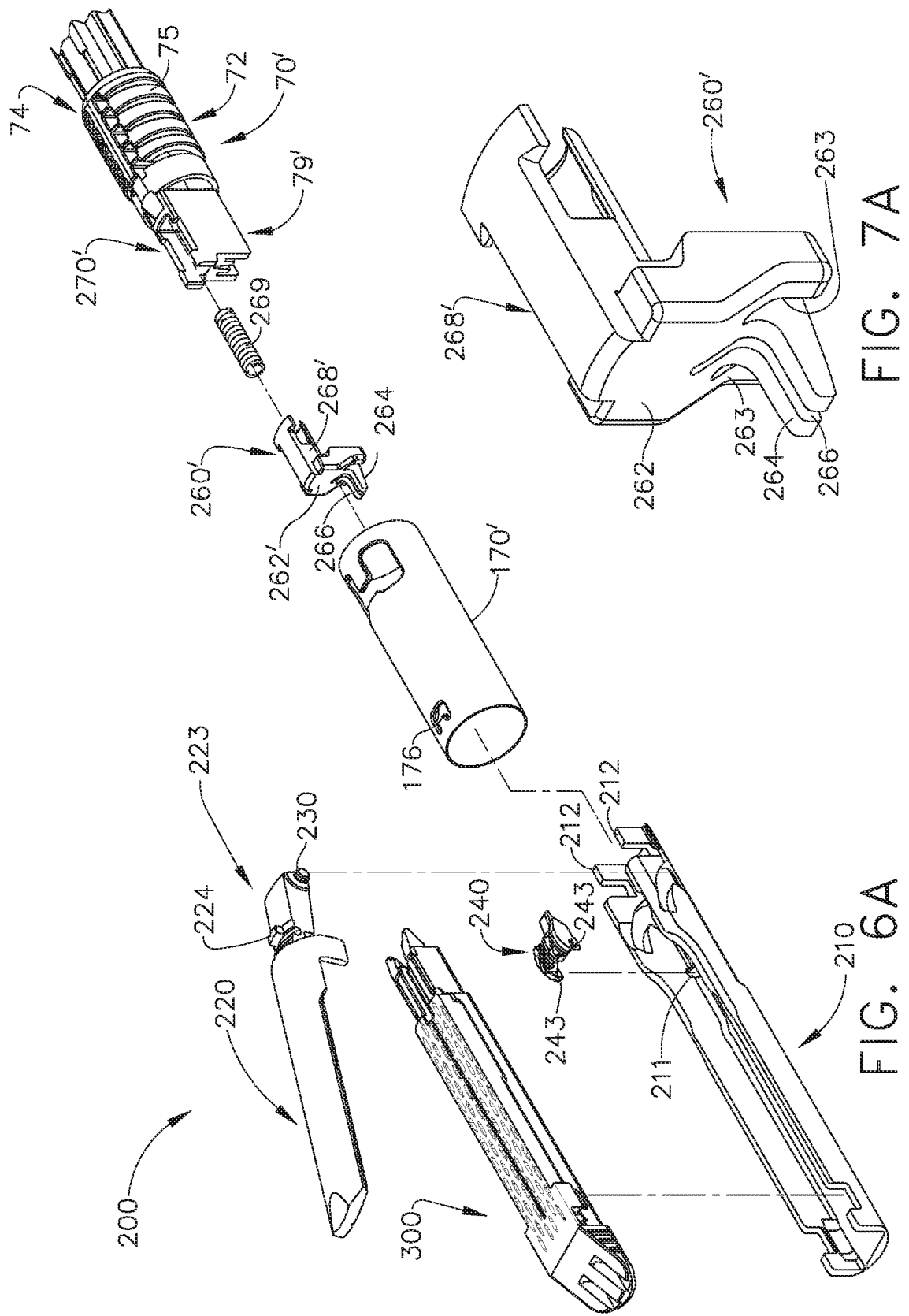

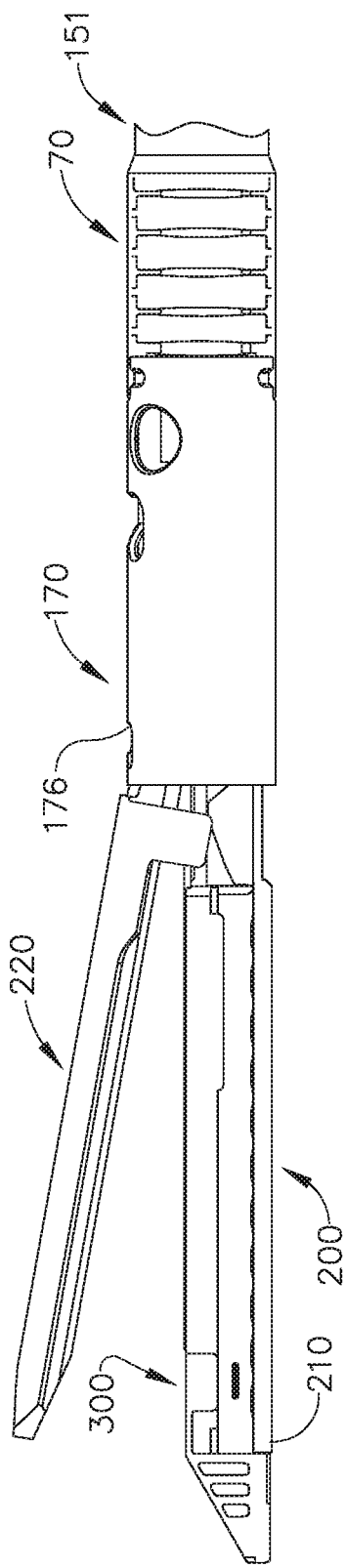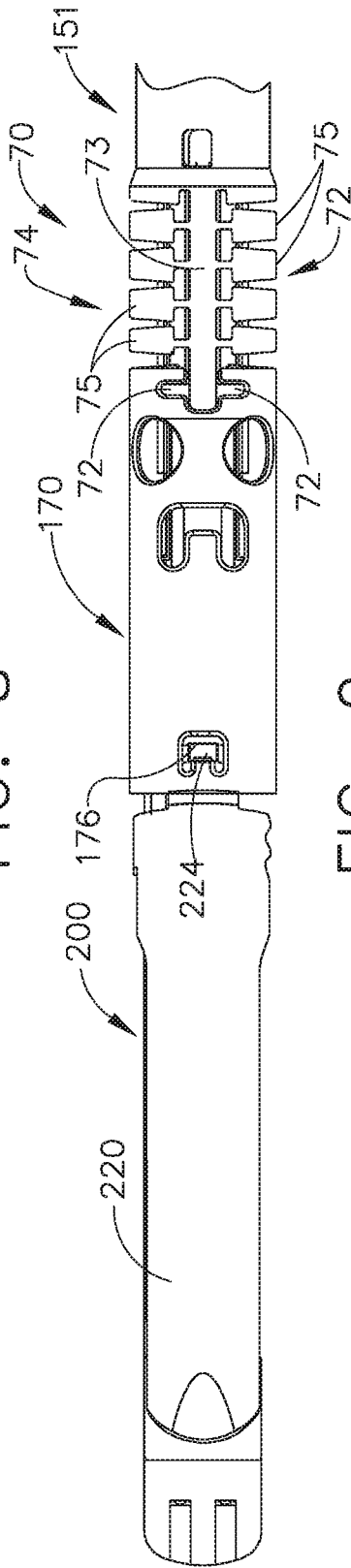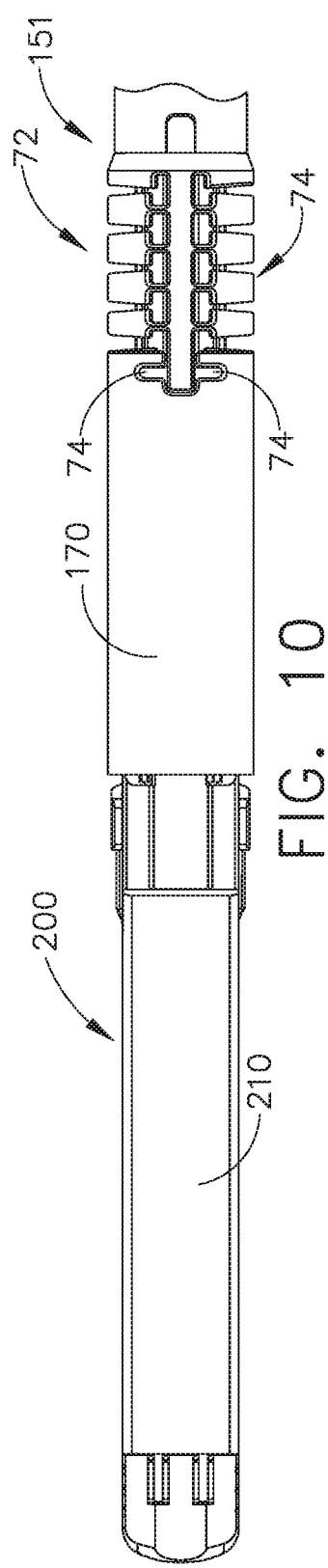

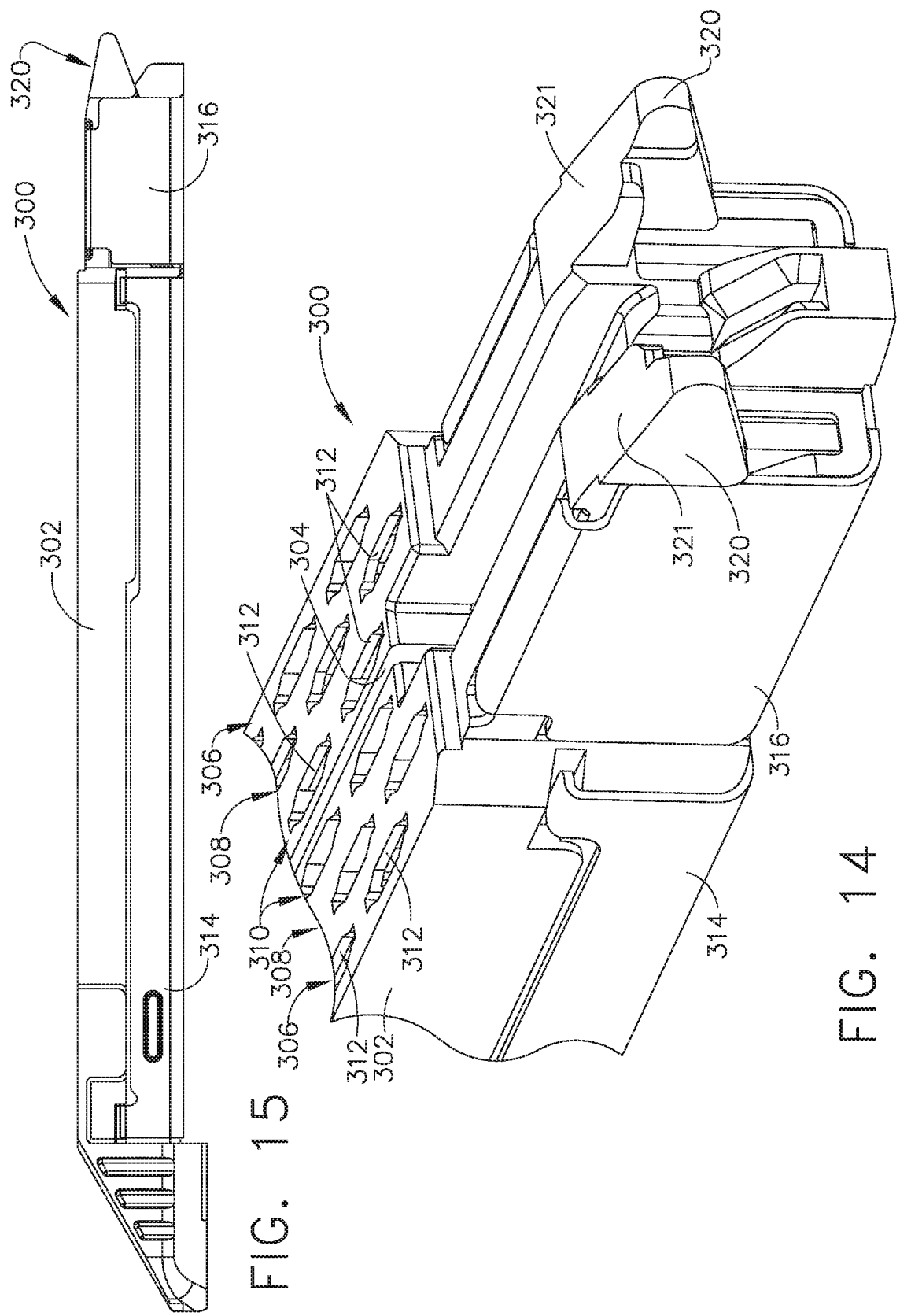

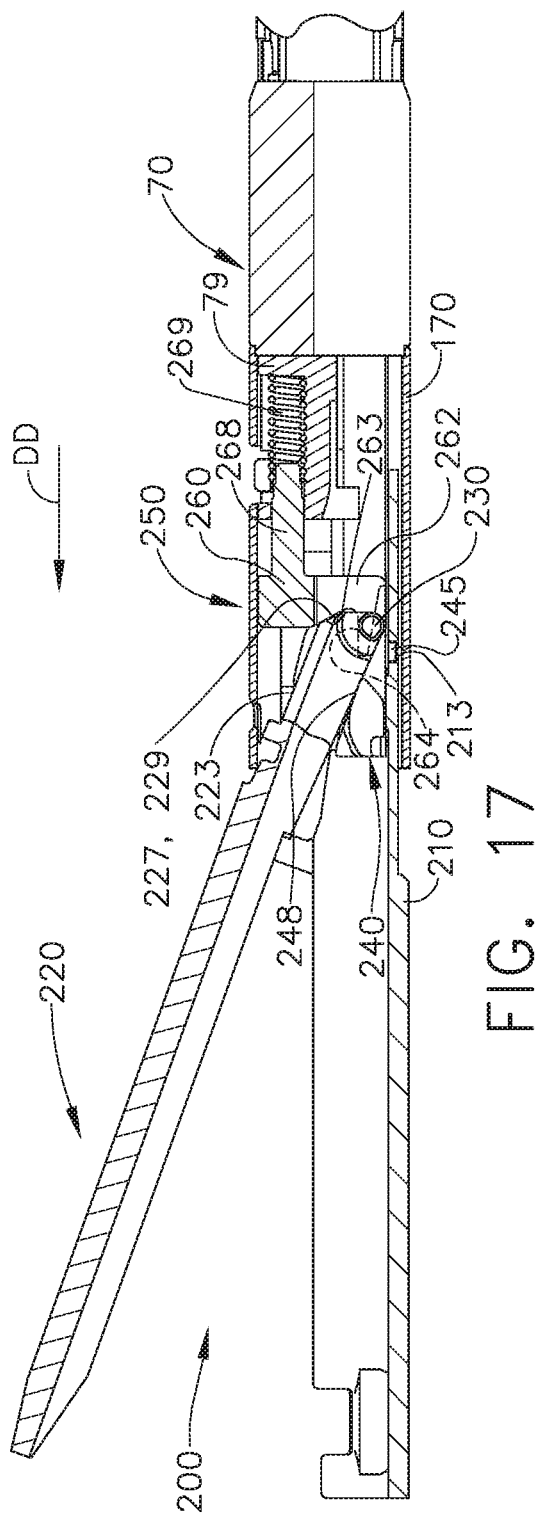
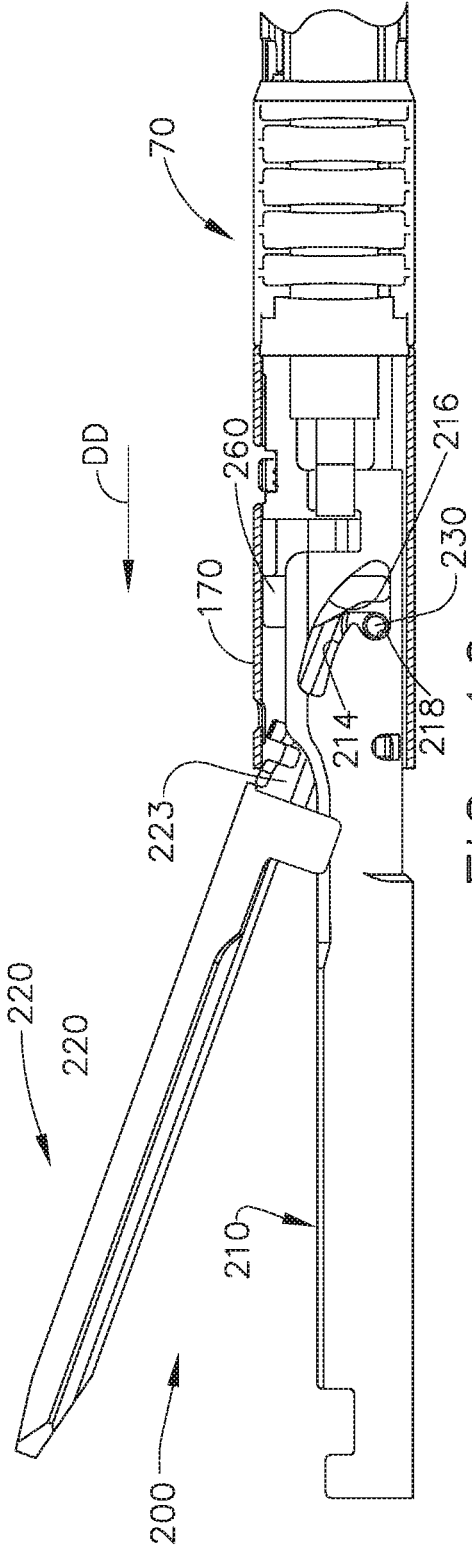

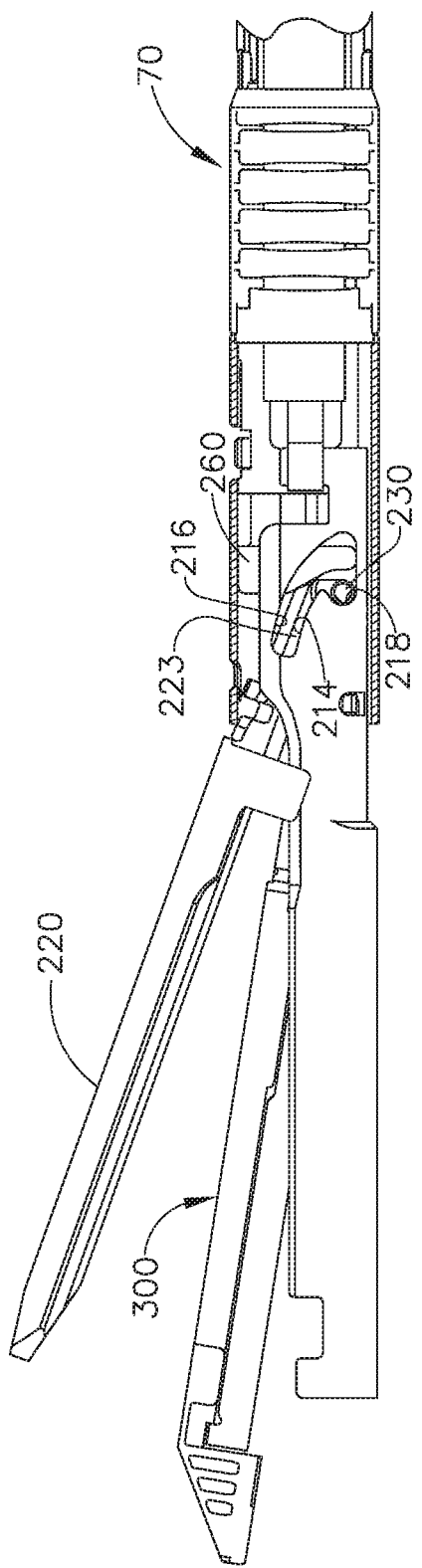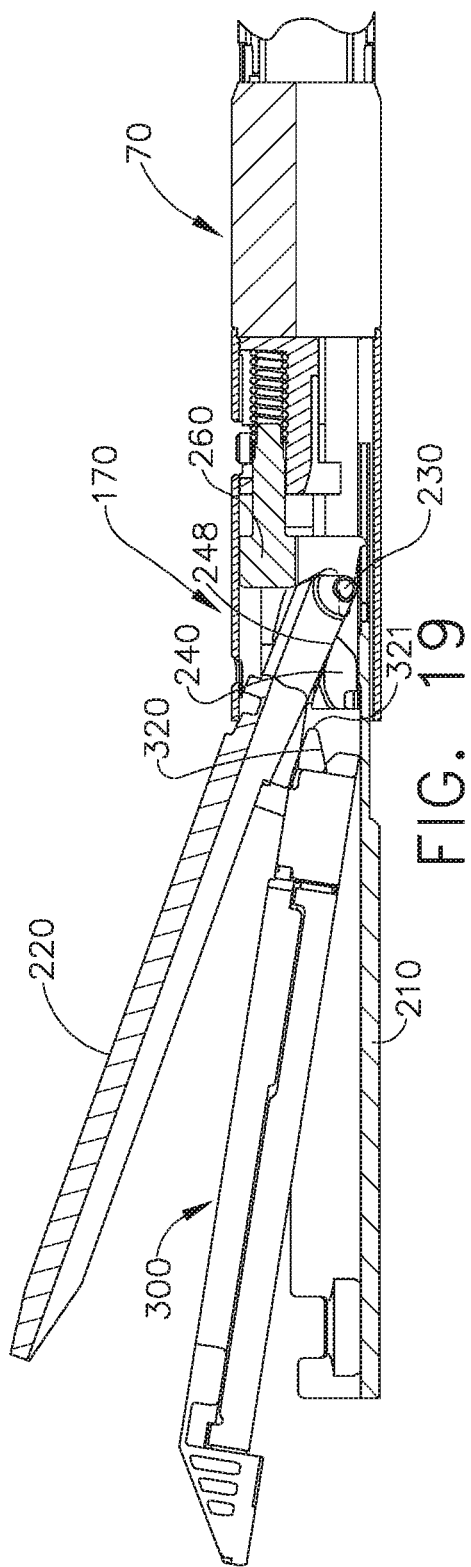

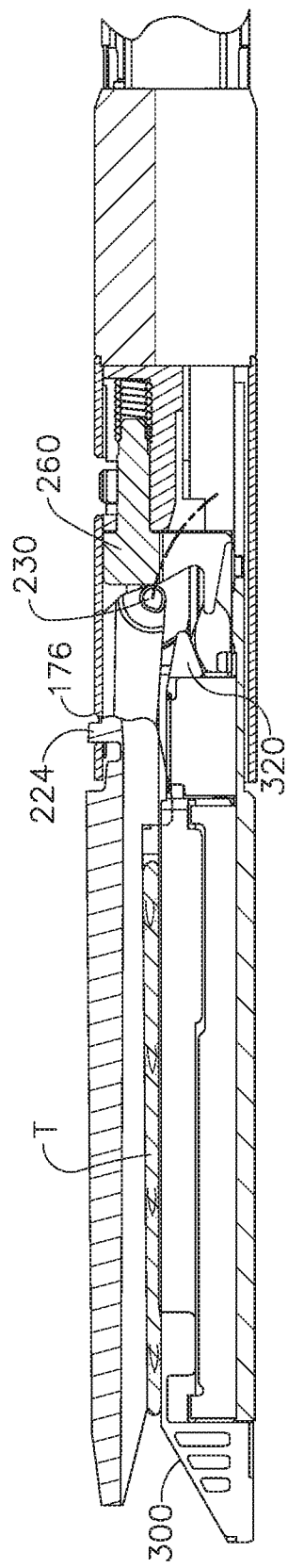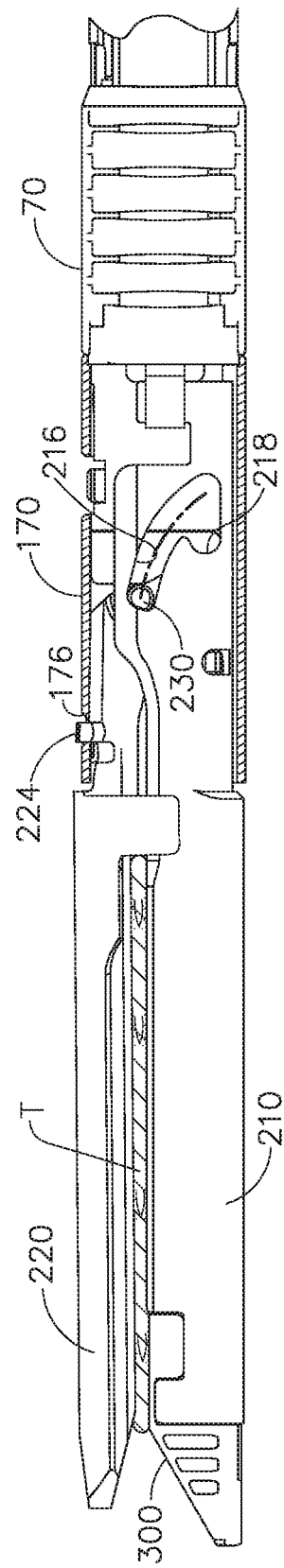

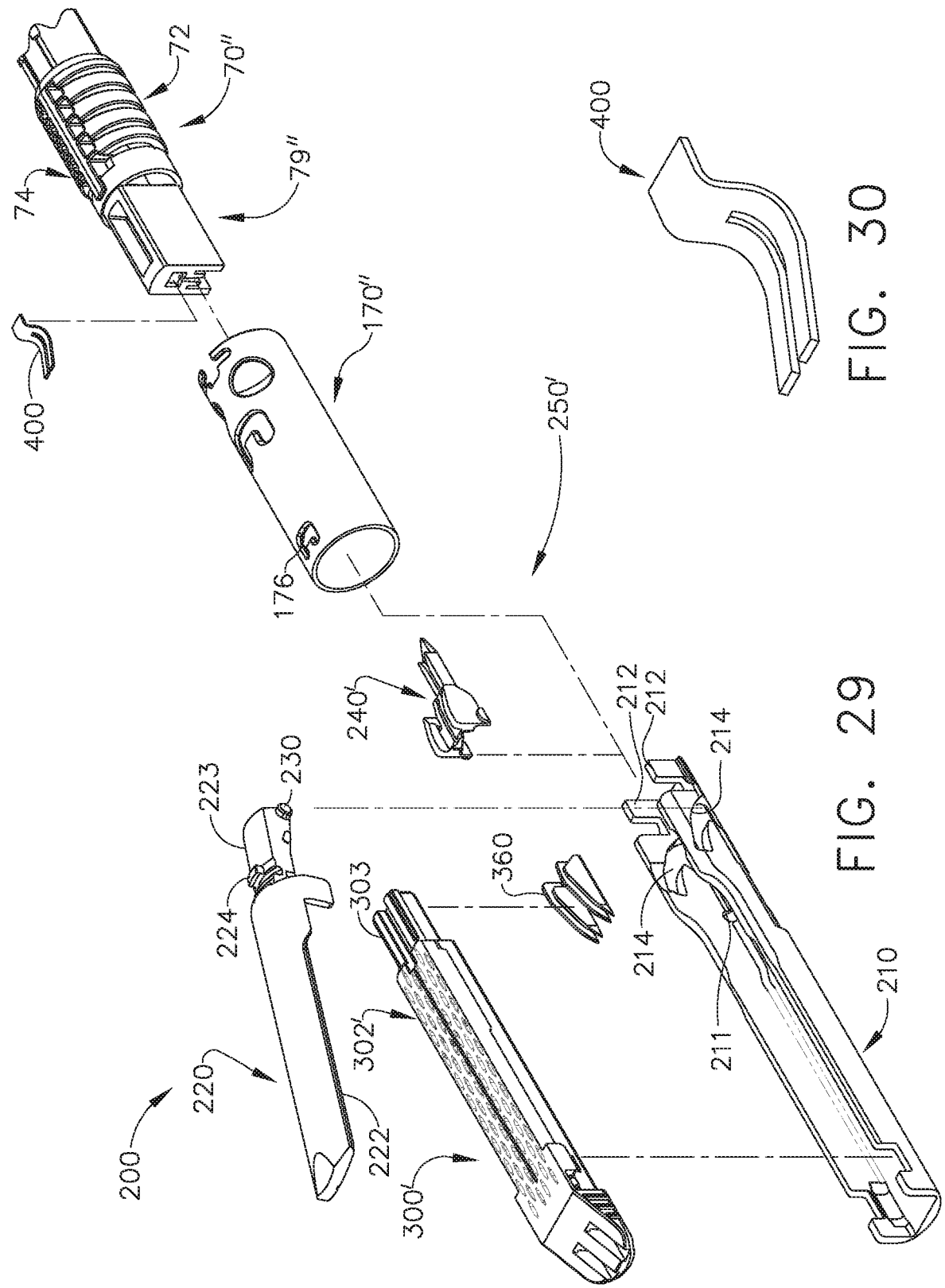

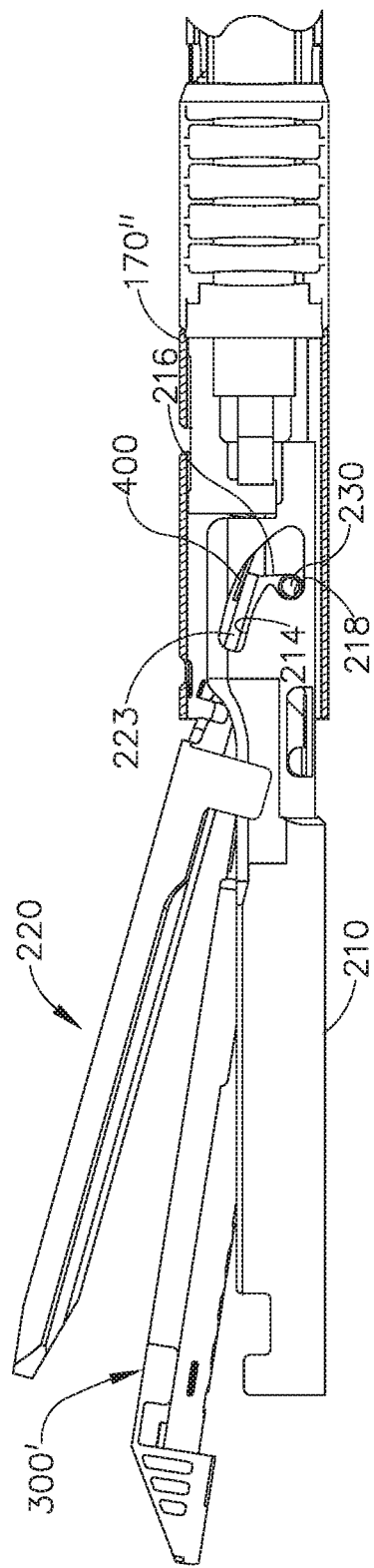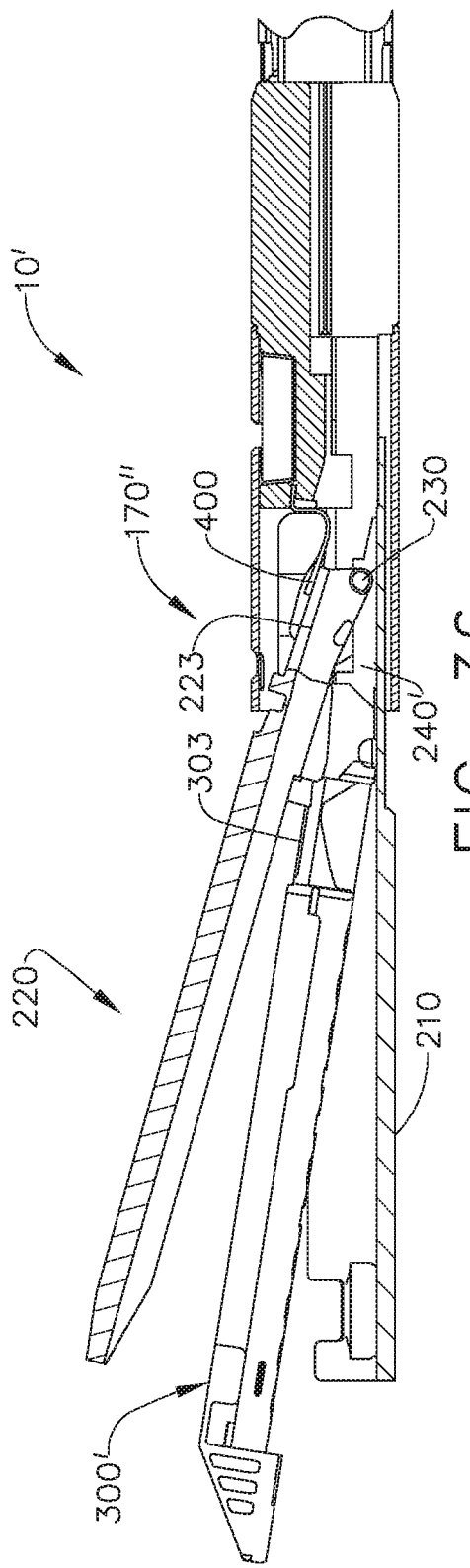

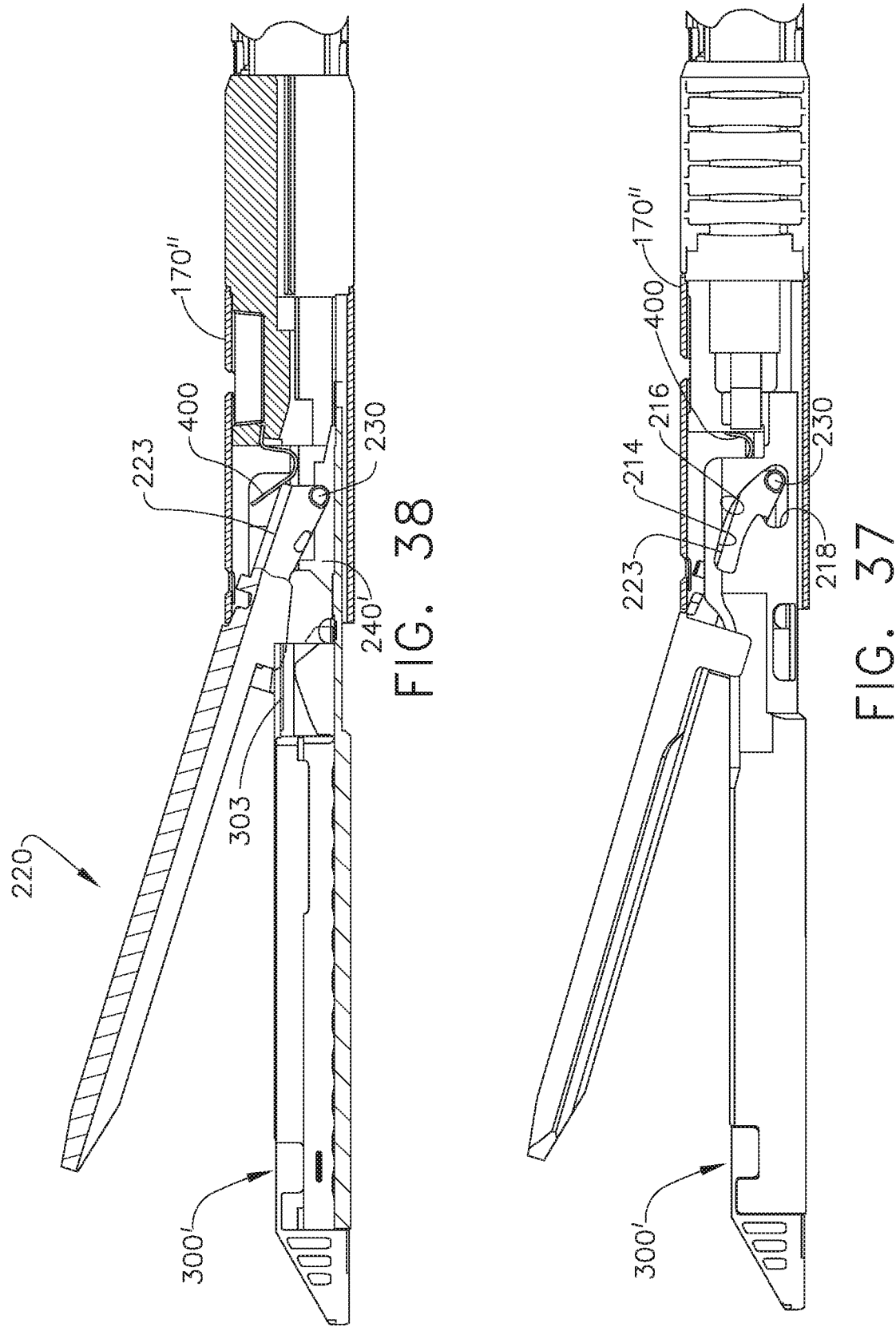

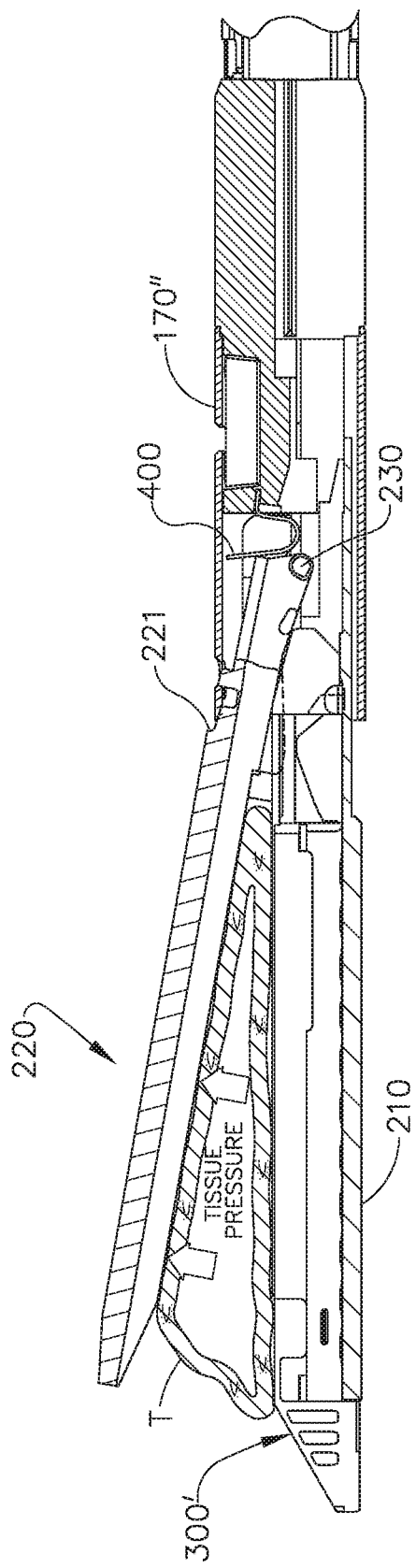
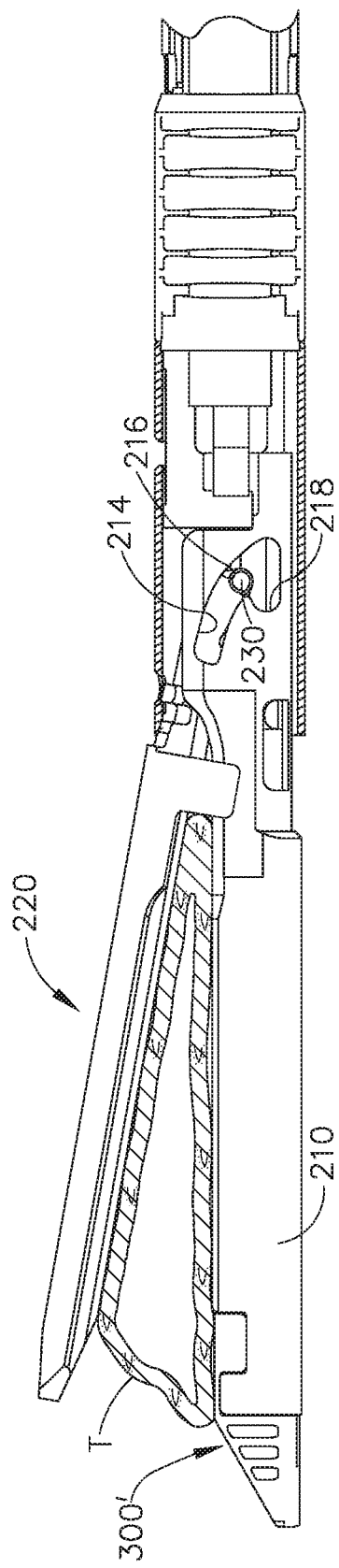

SURGICAL STAPLING DEVICE WITH LOCKOUT SYSTEM FOR PREVENTING ACTUATION IN THE ABSENCE OF AN INSTALLED STAPLE CARTRIDGE

CROSS REFERENCE TO RELATED APPLICATIONS

This application is a continuation application claiming priority under 35 U.S.C. § 120 to U.S. patent application Ser. No. 14/746,305, entitled SURGICAL STAPLING DEVICE WITH LOCKOUT SYSTEM FOR PREVENTING ACTUATION IN THE ABSENCE OF AN INSTALLED STAPLE CARTRIDGE, filed Jun. 22, 2015, which issued on Jan. 1, 2019 as U.S. Pat. No. 10,166,025, which is a continuation application claiming priority under 35 U.S.C. § 120 to U.S. patent application Ser. No. 13/429,647, entitled SURGICAL STAPLING DEVICE WITH LOCKOUT SYSTEM FOR PREVENTING ACTUATION IN THE ABSENCE OF AN INSTALLED STAPLE CARTRIDGE, filed Mar. 26, 2012, which issued on Jul. 14, 2015 as U.S. Pat. No. 9,078,653, the entire disclosures of which are hereby incorporated by reference herein.

BACKGROUND

The present invention relates to surgical instruments and, in various embodiments, to surgical cutting and stapling instruments and staple cartridges therefor that are designed to cut and staple tissue.

SUMMARY

In accordance with at least one general form, there is provided a surgical stapling instrument that includes an end effector that has an elongate channel that is configured to operably support a surgical staple cartridge therein. An anvil is movably supported on the elongate channel between an open position and closed positions in response to an application of opening and closing motions applied thereto. An anvil lock member cooperates with the anvil to retain the anvil in an open position when a staple cartridge has not been installed in the elongate channel and prevents the anvil from moving to a closed position until the staple cartridge has been seated within the elongate channel.

In accordance with at least one other general form, there is provided a surgical stapling instrument that includes a handle and an elongate shaft assembly that is operably coupled to the handle. A closure system is operably supported by the handle for generating closing and opening motions in response to actuation of a closure trigger operably supported by the handle. The instrument further includes an elongate channel that is coupled to the elongate shaft assembly. The instrument also includes an anvil that has an anvil mounting portion that is movably supported on the elongate channel between an open position and closed positions in response to applications of opening and closing motions transmitted thereto through the elongate shaft assembly. An anvil lock member is operably supported by the elongate shaft assembly for movable engagement with the anvil mounting portion. A surgical staple cartridge is configured to be seated within the elongate channel and cooperates with the anvil mounting portion such that when the surgical staple cartridge has not been seated within the elongate channel, the anvil lock member cooperates with the anvil mounting portion to retain the anvil in the open position. In addition, when the surgical staple cartridge is seated within the elongate channel, the staple cartridge moves the anvil mounting portion to a position wherein the anvil may be closed upon application of the closure motions thereto.

In accordance with still another general form, there is provided a surgical staple cartridge for use with a surgical stapling instrument including an end effector with an anvil that is supported in an open position until moved to an actuatable position wherein the anvil is movable to closed positions in response to a closing motion applied thereto by a closure system. In at least one form, the surgical staple cartridge comprises a cartridge body that is sized to be removably seated within a portion of the end effector such that a portion of the cartridge body contacts the anvil to move the anvil from the open position to the actuatable position when seated within the end effector.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIG. 6 is a partial exploded perspective view of an end effector and anvil lock embodiment;

FIG. 6A is a partial exploded perspective view of another end effector and anvil lock member embodiment;

FIG. 7 is a perspective view of an anvil lock member embodiment;

FIG. 7A is a perspective view of an anvil lock member embodiment of FIG. 6A;

FIG. 8 is a side elevational view of an end effector embodiment in an open position;

FIG. 9 is a top view of the end effector of FIG. 8;

FIG. 10 is a bottom view of the end effector depicted in FIGS. 8 and 9;

FIG. 14 is a perspective view of a proximal end portion of a surgical staple cartridge embodiment;

FIG. 15 is a side elevational view of the surgical staple cartridge embodiment depicted in FIG. 14;

FIG. 16 is a side view of an end effector embodiment prior to seating a staple cartridge in the elongate channel;

FIG. 17 is a cross-sectional view of the end effector depicted in FIG. 16;

FIG. 18 is a side view of an end effector embodiment of FIGS. 16 and 17 with the anvil in the open position and wherein a surgical staple cartridge is being inserted into the elongate channel;

FIG. 19 is a cross-sectional view of the end effector of FIG. 18;

FIG. 24 is a side elevational view of the end effector of FIGS. 16-23 in a fully clamped position ready to fire;

FIG. 25 is a cross-sectional view of the end effector of FIG. 24;

FIG. 29 is a partial exploded perspective view of an end effector and another anvil lock member embodiment;

FIG. 30 is a perspective view of another anvil lock member embodiment;

FIG. 35 is a side view of an end effector embodiment of FIGS. 33 and 34 with the anvil in the open position and wherein a surgical staple cartridge is being inserted into the elongate channel;

FIG. 36 is a cross-sectional view of the end effector of FIG. 35;

FIG. 37 is a side view of the end effector of FIGS. 33-36 with the staple cartridge embodiment seated within the elongate channel;

FIG. 38 is a cross-sectional view of the end effector of FIG. 37;

FIG. 39 is a side elevational view of the end effector of FIGS. 33-38 clamping tissue;

FIG. 40 is a cross-sectional view of the end effector of FIG. 39;

DETAILED DESCRIPTION

Figure 1:
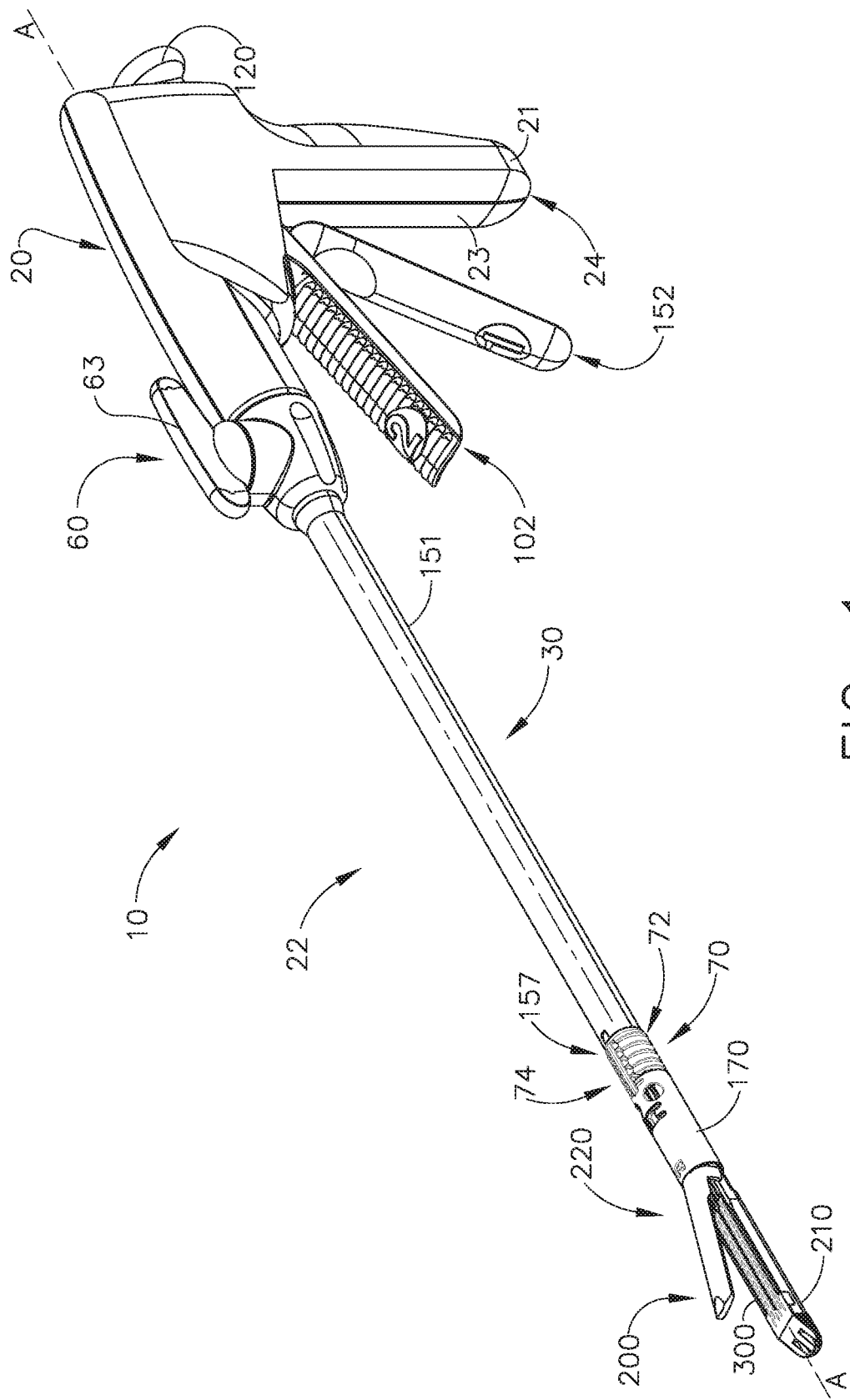
FIG. 1 is a perspective view of a surgical stapling instrument embodiment.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

Figure 2:
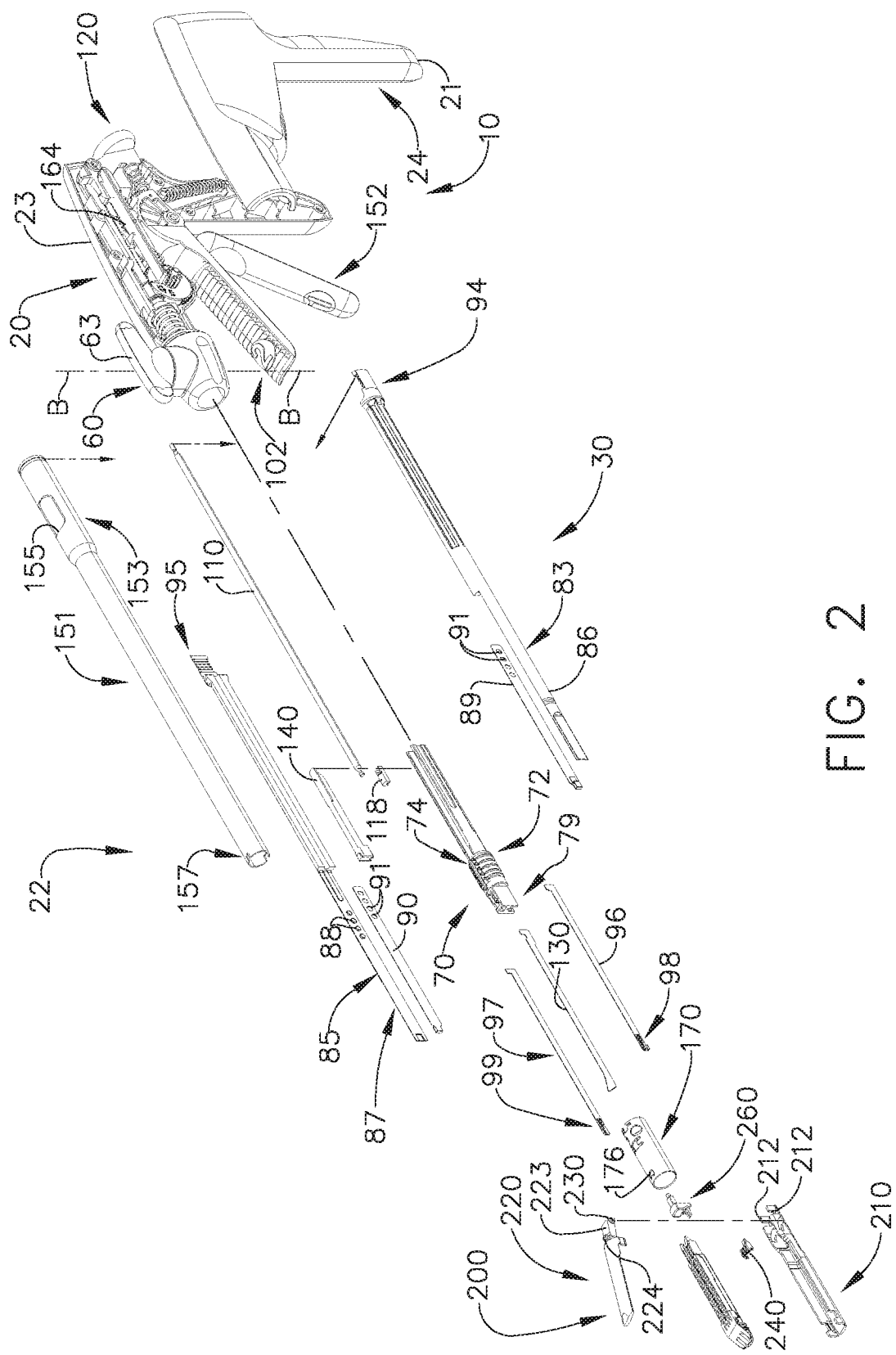
FIG. 2 is an exploded assembly view of the surgical stapling instrument of FIG. 1.

Turning to the Drawings wherein like numerals denote like components throughout the several views, FIGS. 1 and 2 depict a surgical stapling device 10 that is capable of practicing the unique benefits of various embodiments disclosed herein. An exemplary surgical device that has features with which embodiments of the present invention may be effectively employed is disclosed in U.S. Pat. No. 5,704,534, entitled ARTICULATION ASSEMBLY FOR SURGICAL INSTRUMENTS, issued Jun. 6, 1998, the entire disclosure of which is herein incorporated by reference. Various other exemplary surgical stapling device embodiments are described in greater detail in the following U.S. Patents which are each herein incorporated by reference in their respective entireties: U.S. Pat. No. 6,964,363, entitled SURGICAL STAPLING INSTRUMENT HAVING ARTICULATION JOINT SUPPORT PLATES FOR SUPPORTING A FIRING BAR, issued Nov. 15, 2005; U.S. Pat. No. 7,000,818, entitled SURGICAL STAPLING INSTRU- MENT HAVING SEPARATE DISTINCT CLOSING AND FIRING MOTIONS, issued Feb. 21, 2006; U.S. Pat. No. 7,044,352, entitled SURGICAL STAPLING INSTRUMENT HAVING A SINGLE LOCKOUT MECHANISM FOR PREVENTION OF FIRING, issued May 16, 2006; U.S. Pat. No. 7,111,769, entitled SURGICAL INSTRUMENT INCORPORATING AN ARTICULATION MECHANISM HAVING ROTATION ABOUT THE LONGITUDINAL AXIS, issued Sep. 26, 2006; and U.S. Pat. No. 7,143,923, entitled SURGICAL STAPLING INSTRUMENT HAVING A FIRING LOCKOUT FOR AN UNCLOSED ANVIL, issued Dec. 5, 2006.

Referring again to FIGS. 1 and 2, the depicted surgical stapling device 10 includes a handle 20 that is operably connected to an implement portion 22, the latter further comprising an elongate shaft assembly 30 that is operably coupled to an end effector 200. The handle 20 includes a pistol grip 24 toward which a closure trigger 152 is pivotally drawn by the clinician to cause clamping, or closing of an anvil 220 toward an elongate channel 210 of the end effector 200. A firing trigger 102 is farther outboard of the closure trigger 152 and is pivotally drawn by the clinician to cause the stapling and severing of clamped tissue in the end effector 200.

For example, closure trigger 152 is actuated first. Once the clinician is satisfied with the positioning of the end effector 200, the clinician may draw back the closure trigger 152 to its fully closed, locked position proximate to the pistol grip 24. Then, the firing trigger 102 is actuated. The firing trigger 102 springedly returns when the clinician removes pressure. A release button 120 when depressed on the proximal end of the handle 20 releases the locked closure trigger 152.

Articulation System

The depicted embodiment include an articulation assembly 62 that is configured to facilitate articulation of the end effector 200 about the elongate axis A-A of the device 10. Various embodiments, however, may also be effectively employed in connection with non-articulatable surgical stapling devices. As can be seen in FIG. 2, for example, the elongate shaft assembly 30 includes a proximal closure tube segment 151 that is operably supported by a nozzle 60 that is supported on the handle 20. The handle 20 may be formed from two handle cases 21, 23 that operably contain firing and closure systems 100, 150. A proximal end portion 153 of the proximal closure tube segment 151 is rotatably supported by the handle 20 to facilitate its selective rotation about the elongate axis A-A. See FIG. 1. As can also be seen in FIGS. 1 and 2, in at least one embodiment, a distal end portion 157 of the proximal closure tube segment 151 is coupled to a flexible neck assembly 70. The flexible neck assembly 70 has first and second flexible neck portions, 72 and 74, which receive first and second elongate flexible transmission band assemblies 83, 85. The first and second transmission band assemblies 83, 85 have exterior reinforcement band portions 86, 87, respectively, extending distally from the structural portions of the bands. Each exterior reinforcement band portion 86, 87 has a plurality of attachment lugs 88 for securing first and second interior articulation bands 89, 90. See FIG. 2. The transmission band assemblies 83, 85 may be, for example, composed of a plastic, especially a glass fiber-reinforced amorphous polyamide, sold commercially under the trade name Grivory GV-6H by EMS-American Grilon. In contrast, it may be desired that the interior articulation bands 89, 90 of the transmission band assemblies 83, 85 be composed of a metal, advantageously full hard 301 stainless steel or its equivalent. The attachment lugs 88 on the exterior reinforcement band portions 86, 87 of the transmission bands 83, 85 are received into and secured within a plurality of lug holes 91 on the corresponding interior articulation band 89, 90. At the distal end of the first and second interior articulation band assemblies 89, 90 there are first and second connectors 92, 93. The articulation assembly further comprises distal articulation bands 96 and 97 that are configured to hookingly engage the first and second connectors 92, 93, respectively. The articulation bands 96 and 97 have receptacles 98, 99 to couple the bands 96, 97 to the end effector 200 as will be discussed in further detail below.

Figure 3:
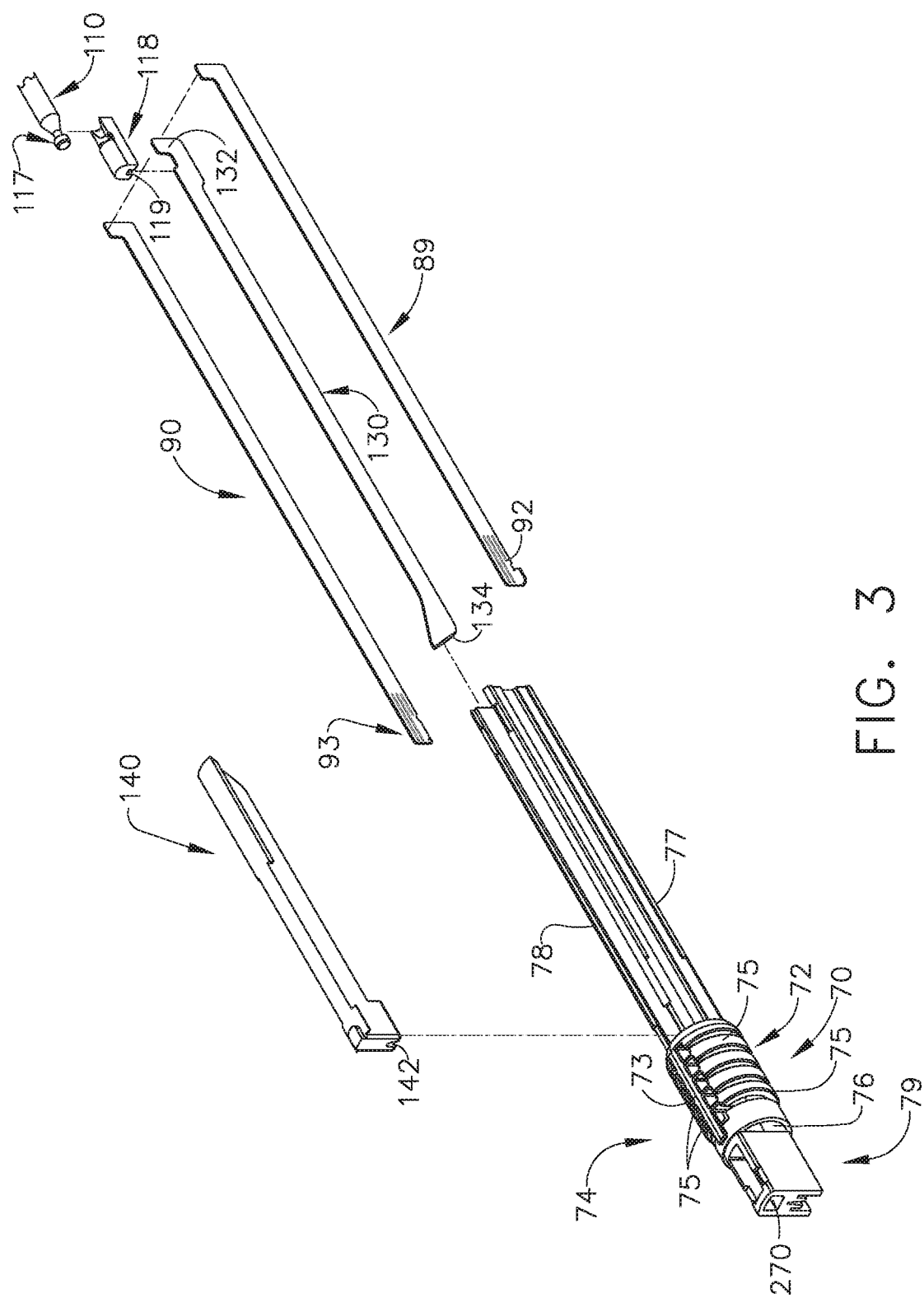
FIG. 3 is an exploded assembly view of a portion of an articulation assembly embodiment.

In at least one form, the flexible neck assembly 70 is preferably composed of a rigid thermoplastic polyurethane sold commercially as ISOPLAST grade 2510 by the Dow Chemical Company. As can be seen in FIG. 3, the flexible neck assembly 70 has first and second flexible neck portions 72, 74. These neck portions 72, 74 are separated by a central longitudinal rib 73. See FIG. 6. The neck portions 72, 74 each have a plurality of neck ribs 75 configured essentially as semi-circular disks. The flexible neck portions 72, 74 together generally form a cylindrical configuration. A side slot 76 extends through each of the neck ribs 75 to provide a passage through the first and second flexible neck portions 72, 74 for receiving the interior articulation bands 89, 90 and exterior reinforcement band portions 86, 87 of the flexible band assemblies 83, 85. In a similar fashion, the central longitudinal rib 73 separating the first and second flexible neck portions 72, 74 has a central longitudinal slot for providing a passage to receive the stapler actuating members. Extending proximally from the first and second flexible neck portions 72, 74 are first and second support guide surfaces 77, 78 for supporting the reciprocating movement of the interior articulation bands 89, 90 and the exterior reinforcement portions 86, 87 of the flexible transmission band assemblies 83, 85. Extending from the distal end of the flexible neck portions 72, 74 is a channel guide 79 for guiding the movement of the stapler actuating members into a staple cartridge 300 of the end effector 200 as will be further discussed below.

In at least one form, when the first and second transmission band assemblies 83, 85 are brought into contact with each other during assembly of the instrument 10, they form an elongate cylinder which has a longitudinal cavity through it that is concentrically positioned between the band assemblies 83, 85 for the passage of a firing rod 110. The proximal ends of the first and second bands have first and second gear racks 94, 95 which, as will be discussed below, meshingly engage an articulation assembly 62.

Figure 4:
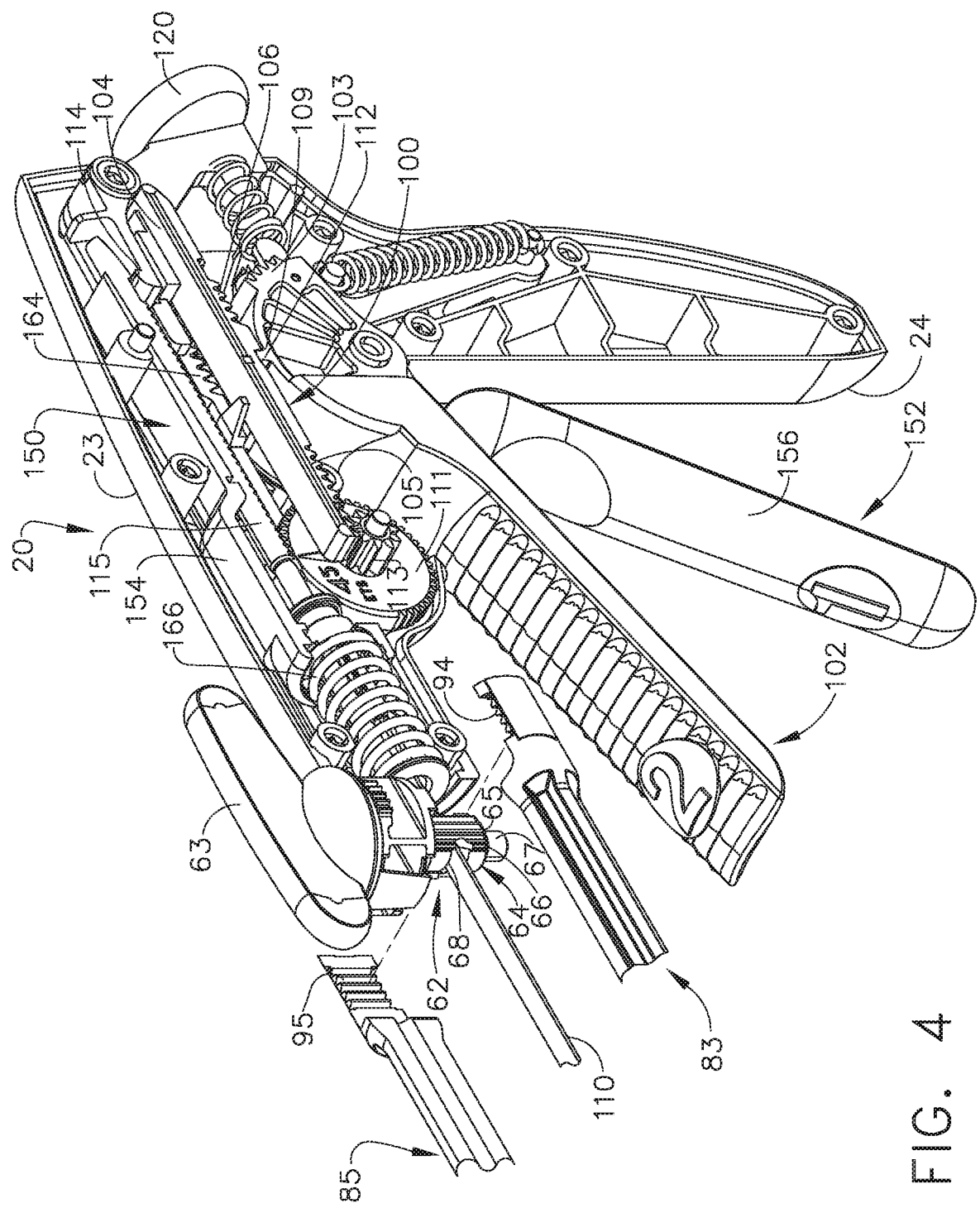
FIG. 4 is a partial exploded perspective view of a portion of the handle.
Figure 5:
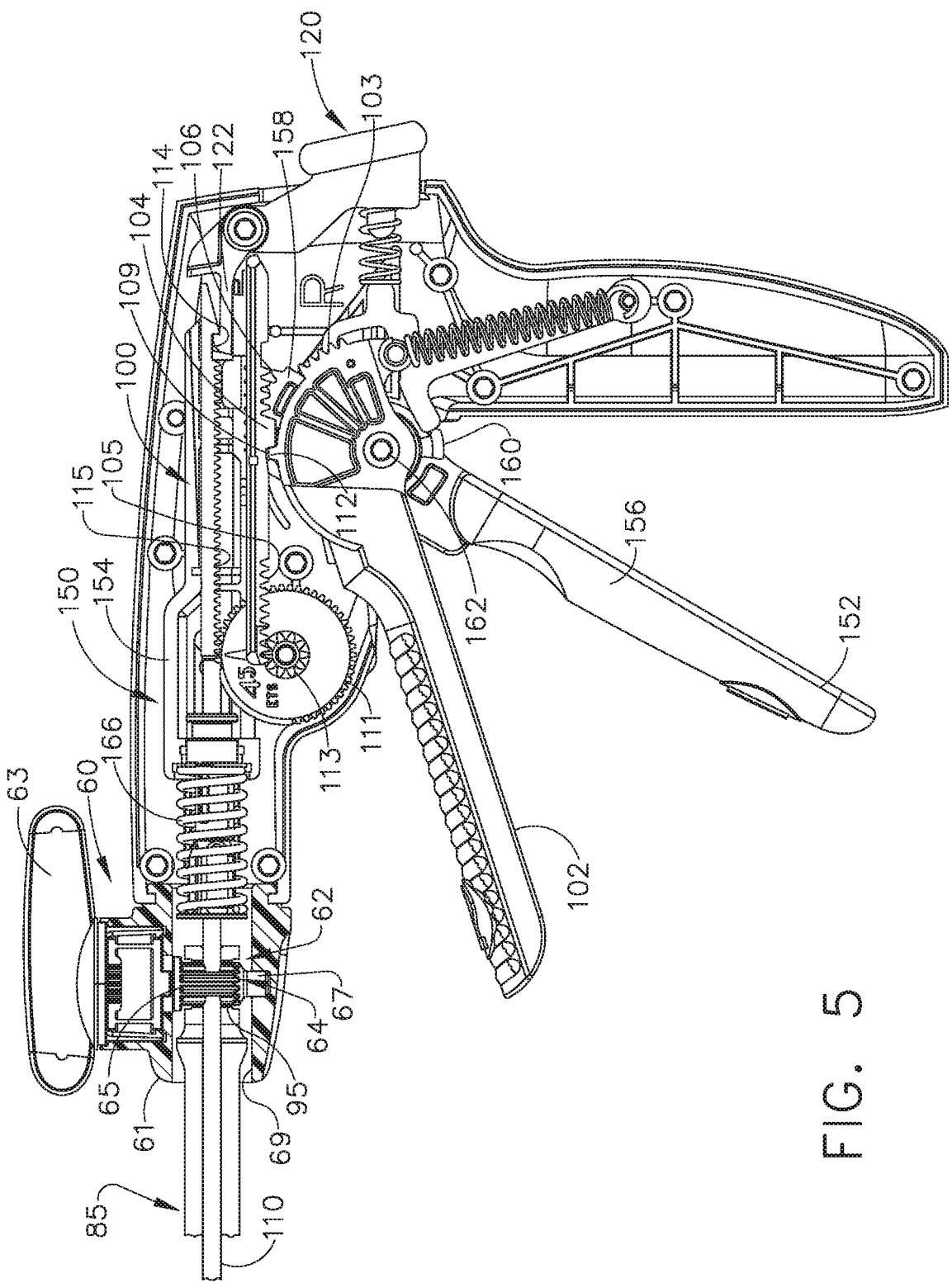
FIG. 5 is a side view of the handle with a handle case removed.

Upon rotation of the articulation assembly 62, one of the first and second flexible transmission band assemblies is moved forwardly and the other band assembly is moved rearwardly. In response to the reciprocating movement of the band assemblies 83, 85 within the first and second flexible neck portions 72, 74 of the flexible neck assembly 70, the flexible neck assembly 70 bends to provide articulation. As can be seen in FIG. 5, an articulation assembly 62 includes an actuator 63, an articulation body 64 and the nozzle 60. Rotational movement of the actuator 63 causes corresponding rotation of the articulation body 64 within the nozzle 60. The first and second elongate transmission band assemblies 83, 85, consequently reciprocate axially in opposite directions parallel to the longitudinal axis A-A of the endoscopic shaft 30 of the stapling device 10 to cause the remote articulation of the end effector 200 through the flexible neck assembly 70. The articulation body 64 further includes a drive gear 65 thereon. As can be seen in FIG. 4, the drive gear 65 has a flared opening 66 through it, and a lower pivot 67. Within the flared opening 66 of the drive gear 65, there is a firing rod orifice 68 for receiving the firing rod 110 enabling the firing of staples into the clamped tissue in response to pivotal rotation of the firing trigger 102. The drive gear 65 is supported for meshing engagement with the first and second drive racks 94, 95 on the flexible elongate transmission band assemblies 83, 85 to effect the desired reciprocating movement of the band assemblies 83, 85.

As can be seen in FIG. 5, the nozzle 60 of the articulation assembly 62 has a nozzle body 61. The nozzle body 61 has an axial bore 69 extending through it for receiving the drive gear 65 of the articulation body 64. The bore 69 provides a continuous opening axially from the frame into the elongate endoscopic shaft 30 and therefore the firing rod 110 and other operative components of the stapling device 10 can communicate with the end effector 200. Further details relating to the articulation assembly 62 may be found in U.S. Pat. No. 5,704,534, which has been previously herein incorporated by reference.

Closure System

As will be discussed in further detail below, the end effector 200 comprises an elongate channel 210 that is configured to operably receive a surgical staple cartridge 300. An anvil 220 is movably supported relative to the elongate channel 210 and is moved from an open position (FIGS. 16 and 17) to closed positions wherein tissue may be cut and stapled (FIGS. 24 and 25). The movement of the anvil 220 between open and closed positions is at least partially controlled by a closure system, generally designated as 150, which, as indicated above, is controlled by the closure trigger 152. The closure system 150 includes the proximal closure tube segment 151 that operably houses the articulation band assemblies 83, 85 in the manner discussed above and which is non-movably coupled to the flexible neck assembly 70.

In various forms, the proximal closure tube segment 151 includes a proximal end portion 153 that axially extends through the bore 69 in the nozzle 60. The proximal closure tube segment 151 has elongate axial slots 155 therethrough to permit the articulation body 64 to extend therethrough. See FIG. 2. The slots 155 enable the articulation body 64 to rotate about articulation axis B-B relative to the proximal closure tube segment 151 while facilitating the axial movement of the proximal closure tube segment 151 along axis A-A relative to articulation body 64. The transmission bands 83, 85 function as a frame upon which the proximal closure tube segment 151 can axially move. The proximal end 153 of the proximal closure tube segment 151 is rotatably coupled to a closure yoke 154 that is supported within the handle 20 for reciprocating motion therein. See FIGS. 4 and 5.

The closure trigger 152 has a handle section 156, a gear segment section 158 and an intermediate section 160. See FIG. 5. A bore extends through the intermediate section 160. A cylindrical support member 162 extending from the second handle housing 23 passes through the bore for pivotably mounting the closure trigger 152 on the handle portion 20. A proximal end 98 of the closure yoke 154 has a gear rack 164 that is engaged by the gear segment section 158 of the closure trigger 152. When the closure trigger 152 is moved toward the pistol grip 24 of the handle portion 20, the closure yoke 154 and, hence, the proximal closure tube segment 151 move distally, compressing a spring 166 that biases the closure yoke 152 proximally.

In at least one form, the closure system 150 further includes a distal closure tube segment 170 that is non-movably coupled to the channel guide portion 79 of the flex neck assembly 70 by attachment tabs 72, 74. See FIGS. 9 and 10. The distal closure tube segment 170 has an opening 176 therein that is adapted to interface with an upstanding tab 224 formed on the anvil 220 as will be discussed in further detail below. Thus, axial movement of the proximal closure tube segment 151 results in axial movement of the flex neck assembly 70, as well as the distal closure tube segment 170. For example, distal movement of the proximal closure tube segment 151 effects pivotal translation movement of the anvil 220 distally and toward the elongate channel 210 of the end effector 200 and proximal movement effects opening of the anvil 220 as will be discussed in further detail below.

Firing System

In at least one form, the surgical instrument 10 further includes a firing system, generally designated as 100, for applying firing motions to the firing rod 110 in response to actuation of the firing trigger 102. In at least one form, the firing system 100 further includes a drive member 104 that has first and second gear racks 105, 106 thereon. A first notch 109 is provided on the drive member 105 intermediate the first and second gear racks 105, 106. During return movement of the firing trigger 102, a tooth 112 on the firing trigger 102 engages with the first notch 109 for returning the drive member 104 to its initial position after staple firing. A second notch 114 is located at a proximal end of the firing rod 110 for locking the firing rod 110 to an upper latch arm 122 of the release button 120 in its unfired position. The firing system 150 further includes first and second integral pinion gears 111, 113. The first integral pinion gear 111 is engaged with a drive rack 115 provided on the firing rod 110. The second integral pinion gear 113 is engaged with the first gear rack 105 on the drive member 104. The first integral pinion gear 111 has a first diameter and the second integral pinion gear 113 has a second diameter which is smaller than the first diameter.

In various embodiments, the firing trigger 102 is provided with a gear segment section 103. The gear segment section 103 engages the second gear rack 106 on the drive member 104 such that motion of the firing trigger 102 causes the drive member 104 to move back and forth between first and second drive positions. In order to prevent staple firing before tissue clamping has occurred, the upper latch arm 122 on the release button 120 is engaged with the second notch 114 on the drive rack 115 such that the firing rod 110 is locked in its proximal-most position. When the upper latch arm 122 falls into a recess in the closure yoke, the upper latch arm 122 disengages with the second notch 114 to permit distal movement of the firing rod 110. Because the first gear rack 105 on the drive member 104 and the drive rack 115 on the firing rod 110 are engaged, movement of the firing trigger 102 causes the firing rod 110 to reciprocate between a first reciprocating position and a second reciprocating position. Further details concerning various aspects of the firing system 150 may be gleaned from reference to U.S. Pat. No. 7,000,818 which has been herein incorporated by reference in its entirety.

As can be seen in FIG. 3, various embodiments, the distal end 117 of the firing rod 110 is rotatably received within a firing bar mounting yoke 118. The firing bar mounting yoke 118 has a slot 119 for hookingly receiving a hook 132 formed on a proximal end of a knife bar 130. In addition, as shown in FIG. 3, a support bar 140 is supported for axial movement between the first and second support guide surfaces 77, 78 of the flex neck assembly 70. The support bar 140 has a slot 142 that is configured to permit the knife bar 130 to slidably pass therethrough. The metal knife bar 130 has a tissue cutting edge 134 formed on its distal end and is configured to operably interface with a wedge sled operably supported within a surgical staple cartridge 300.

End Effector

Figure 11:
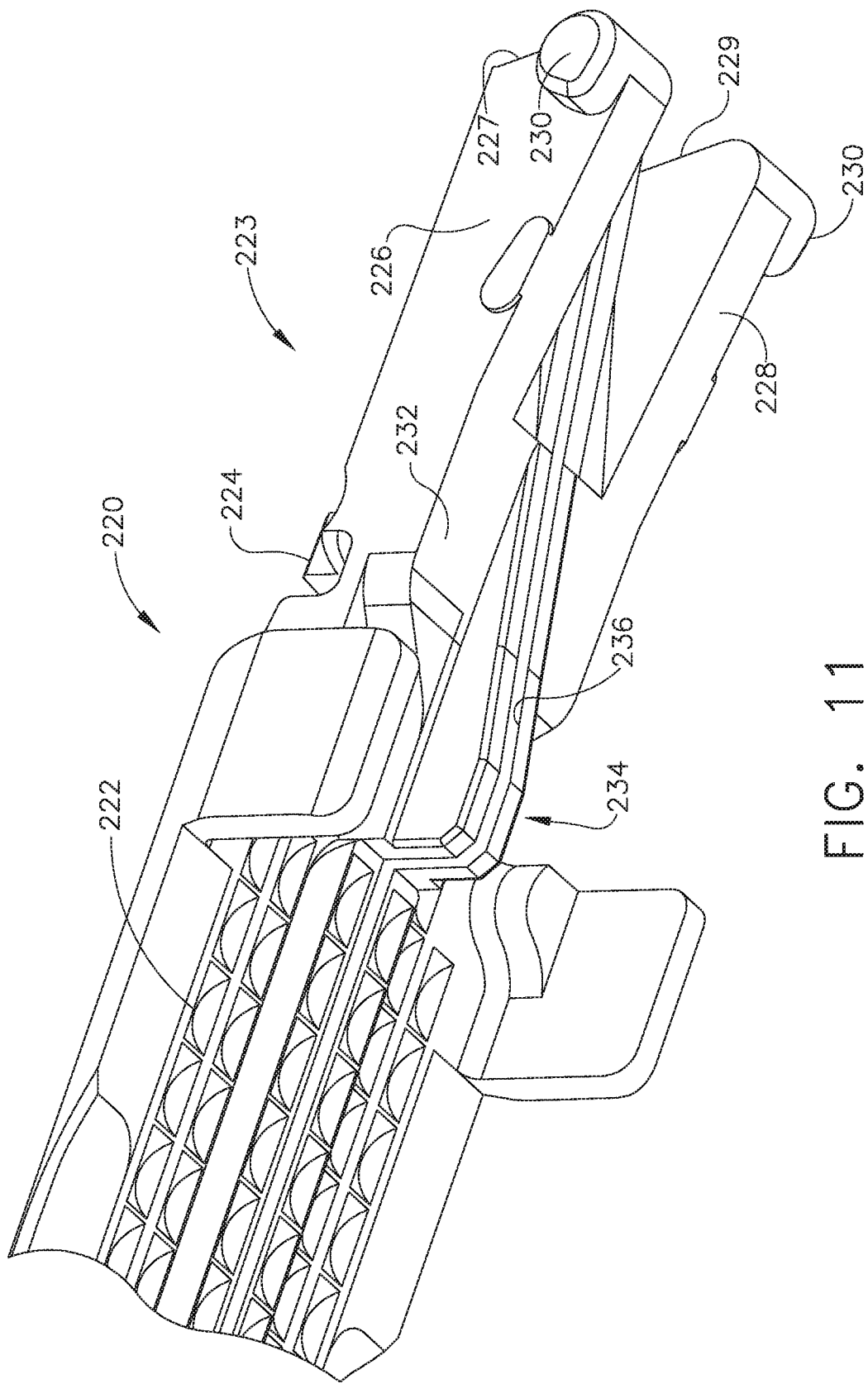
FIG. 11 is a partial bottom perspective view of an anvil embodiment.

As discussed above, in at least one form, an end effector 200 includes an elongate channel 210 that is configured to operably support a surgical staple cartridge 300 therein. As shown in FIGS. 2 and 6, the elongate channel 210 has a proximal end portion that includes two spaced mounting tabs 212 that are configured to be engaged by the hooks 998, 99 on the distal ends of the articulation bands 96, 97. Thus, the reciprocating motions of the articulation bands 96, 97 cause the elongate channel 210 to articulate relative to the flex neck assembly 70. As further indicated above, the end effector 200 also includes an anvil 220. In at least one form, the anvil 220 is fabricated from, for example, 416 Stainless Steel Hardened and Tempered RC35 Min (or similar material) and has a staple-forming undersurface 222 thereon that is configured for confronting engagement with the staple cartridge 300 when mounted in the elongate channel 210. The anvil 220 is formed with a proximally extending mounting portion 223 that includes two trunnion walls 226, 228 that each has a trunnion 30 protruding therefrom. See FIG. 11. In addition, formed on the underside 232 of the mounting portion 223 is a downwardly protruding pivot tab 234 that has a slot 236 extending therethrough that is configured to receive and support the knife bar 130 as it is axially advanced through the end effector 200 during cutting and stapling. In addition, the anvil opening tab 224 is formed on the mounting portion 223 such that it can operably interface with the opening 176 in the distal closure tube segment 170 as will be further discussed below. As can be seen in FIGS. 16-25, the anvil trunnions 230 are configured to be movably received in corresponding trunnion slots 214 formed in the proximal end of the elongate channel 210. Each trunnion slot 214 has an arcuate segment 216 that communicates with a locking notch 218.

Figures 12, 13:
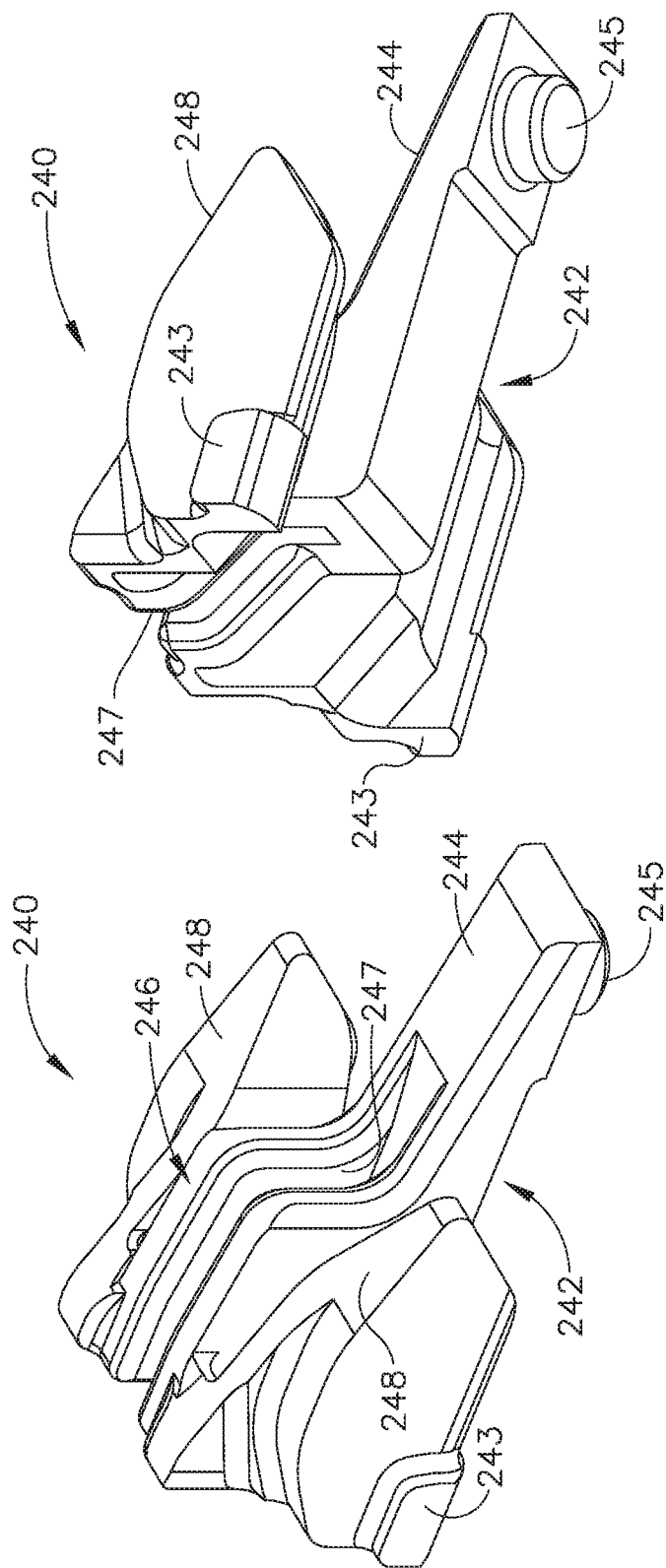
FIG. 12 is a perspective view of a pivot mount embodiment.
FIG. 13 is a bottom perspective view of the pivot mount embodiment of FIG. 12.

To facilitate pivotal travel of the anvil mounting portion 223 relative to the elongate channel 210, various embodiments include a pivot mount 240. As can be in FIGS. 12 and 13, one form of a pivot mount 240 has a body portion 242 that is configured to be attached to the elongate channel 210. For example, the body portion 242 may be formed with two opposed attachment tabs 243 that are configured to retainingly engage tab openings 211 (FIG. 6) formed in the elongate channel 210. In addition, the pivot mount 240 has a proximally extending foot portion 244 that has a retainer lug 245 protruding therefrom that is configured to be received in a corresponding opening 211 in the elongate channel 210. See FIG. 17. The pivot mount 240 may be fabricated from, for example, Vectra A435 Liquid Crystal Polymer—natural or similar materials. As can be further seen in FIGS. 12 and 13, the body portion 242 has an upstanding central portion 246 that has a slot 247 extending therethrough for axially receiving the knife bar 130. The central portion 246 provides lateral support to the knife bar 130 as it is driven through tissue clamped within the end effector 200. Various embodiments of the pivot mount 240 further include rocker surfaces 248 formed on each side of the central portion 246 for pivotally receiving the trunnion walls 226, 228 of the anvil 220 thereon.

Anvil Lockout System

Various embodiments include a unique and novel anvil lockout system 250 that prevents closure of the anvil 220 when a staple cartridge 300 has not been properly installed in the elongate channel 210. Referring to FIGS. 6 and 7, for example, an embodiment of an anvil lockout system 250 includes a movable anvil lock member 260 that is movable in response to contact by a portion or portions of a staple cartridge 300 as will be discussed in further detail below. In at least one form, the anvil lock member 260 comprises a body portion 262 that has a distally protruding central support tab 264 formed thereon. A slot 266 extends through body portion 262 and the central support tab 264 to enable the knife bar 130 to pass therethrough. The body portion 262 further includes proximally extending mounting bar 268 that is configured to be slidably received within a corresponding mounting opening 270 in the channel guide 79 of the flex neck assembly 70. In addition, a biasing member in the form of, for example, a coil spring 269 is supported within the opening 270 to bias the anvil lock member 260 in the distal direction "DD". See FIG. 16. When the anvil 220 is mounted to the elongate channel 210, the trunnions 230 are received within their corresponding trunnion slots 214 in the elongate channel 210, the central support tab 264 of the anvil lock member 260 is received between the trunnion walls 226, 228 to further provide support to the anvil 220. The body portion 262 of the anvil lock member 260 is further formed with two cam surfaces 263 configured to engage the proximal end surfaces 227, 229 of the trunnion walls 226, 228. See FIGS. 6 and 7. Various embodiments of the anvil lock member may be fabricated from, for example, Vectra A435 Liquid Crystal Polymer—natural or similar materials.

FIGS. 6A and 7A illustrate an alternative anvil lock member 260' that is movable in response to contact by a portion or portions of a staple cartridge 300. In at least one form, the anvil lock member 260' comprises a body portion 262 that has a distally protruding central support tab 264 formed thereon. A slot 266 extends through body portion 262 and the central support tab 264 to enable the knife bar 130 to pass therethrough. The body portion 262 further includes proximally extending mounting bar 268' that is configured to be slidably and retainably received within a corresponding mounting opening 270' in the channel guide 79' of the flex neck assembly 70'. In addition, a biasing member in the form of, for example, a coil spring 269 is supported within the opening 270' to bias the anvil lock member 260' in the distal direction "DD". The anvil lock member 260' otherwise operates in the same manner as anvil lock member 260. When the anvil 220 is mounted to the elongate channel 210, the trunnions 230 are received within their corresponding trunnion slots 214 in the elongate channel 210, the central support tab 264 of the anvil lock member 260' is received between the trunnion walls 226, 228 to further provide support to the anvil 220. The body portion 262 of the anvil lock member 260 is further formed with two cam surfaces 263 configured to engage the proximal end surfaces 227, 229 of the trunnion walls 226, 228. The distal closure tube segment 170' operates in the same manner as the distal closure tube segment 170 described above.

Surgical Staple Cartridge

Various embodiments include a unique and novel surgical staple cartridge 300 that is configured to interact with the anvil lockout system 250 when installed in the elongate channel 210. As can be seen in FIGS. 14 and 15, in at least one form, the surgical staple cartridge 300 includes a cartridge body 302 that may be fabricated from, for example, Vectra A435, 20% PTFE/15% GF—natural. The cartridge body 302 is sized and shaped to be received within the elongate channel 210. In at least one form, the cartridge body 302 is configured to be seated in the elongate channel 210 such that is removably retained therein. The cartridge body 302 may be formed with a centrally disposed slot 304 therein for receiving the knife bar 130. On each side of the slot 304, there is provided rows 306, 308, 310 of staple openings 312 that are configured to support a surgical staple therein. In the depicted embodiment, three rows 306, 308, 310 are provided on each side of the slot 304. The surgical staples may be supported on staple drivers that are movably supported within the staple openings 312. Also supported within the staple cartridge body 302 is a wedge sled that is configured for axial movement through the cartridge body 302 when contacted by the cutting bar. The wedge sled is configured with wedge-shaped driving members that contact the staple drivers and drive the drivers and their corresponding staples toward the closed anvil as the wedge sled is driven distally through the cartridge body 302. Examples of staple driver arrangements and wedge sled arrangements that may be employed are described in further detail in U.S. Pat. No. 7,669,746, the entire disclosure which is herein incorporated by reference. In various embodiments, to facilitate installation of the wedge sled and drivers in the cartridge body 302, metal cartridge pans 314, 316 may be attached to the cartridge body 302 as shown in FIGS. 14 and 15. The cartridge pans 314 and 316 serve to retain the wedge sled and drivers within the cartridge body 302.

In various embodiments, the cartridge body 302 additionally has at least one release member formed thereon that protrudes in the proximal direction. In the embodiment depicted in FIG. 14, two release members 320 are formed on the proximal end 319 of the cartridge 300. The release members 320 each have a wedge shape that defines a sloped pivot surface 321 that are configured to pivotally support a portion of the anvil mounting portion 223 thereon.

Installation of a Staple Cartridge

An understanding of the operation of a anvil lockout system may be gleaned from reference to FIGS. 16-25. FIGS. 16 and 17 illustrate the position of the anvil 220 relative to the elongate channel 210 prior to installing a staple cartridge 300. When in that "unloaded" and open position, the anvil lock member 260 is biased in the distal direction by spring 269 such that the cam surfaces 263 on the anvil lock member 260 are in contact with the end surfaces 227, 229 of the trunnion walls 226, 228. The anvil lock member 260 pushes the anvil mounting portion 223 in the distal direction "DD" such that the trunnions 230 are seated in their respective locking notch 218. The cam surfaces 263 on the anvil lock member 260, in cooperation with the end wall surfaces 227, 229, also serve to pivot and retain the anvil in the open position as shown in FIGS. 16 and 17. As can be seen in FIG. 16, when in that position, the trunnion walls 226, 228 are supported on the rocker surfaces 248 on the pivot mount 240. When in that position, the surgeon cannot close the anvil 220 by actuating the closure trigger 152 to advance the distal closure tube 170. Because the closure tube segments cannot be advanced distally to close the anvil 220, the closure trigger 152 cannot be actuated to its fully closed position whereby the firing trigger 102 may be actuated. Thus, when no cartridge 300 is present, the end effector 200 may not be actuated.

Figure 21:
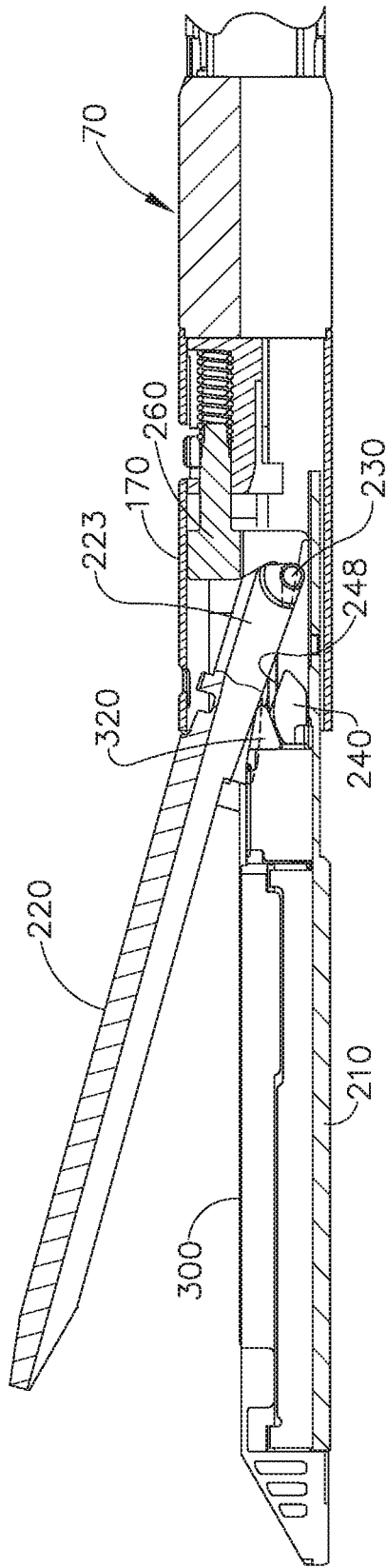
FIG. 21 is a cross-sectional view of the end effector of FIG. 20.
Figure 20:
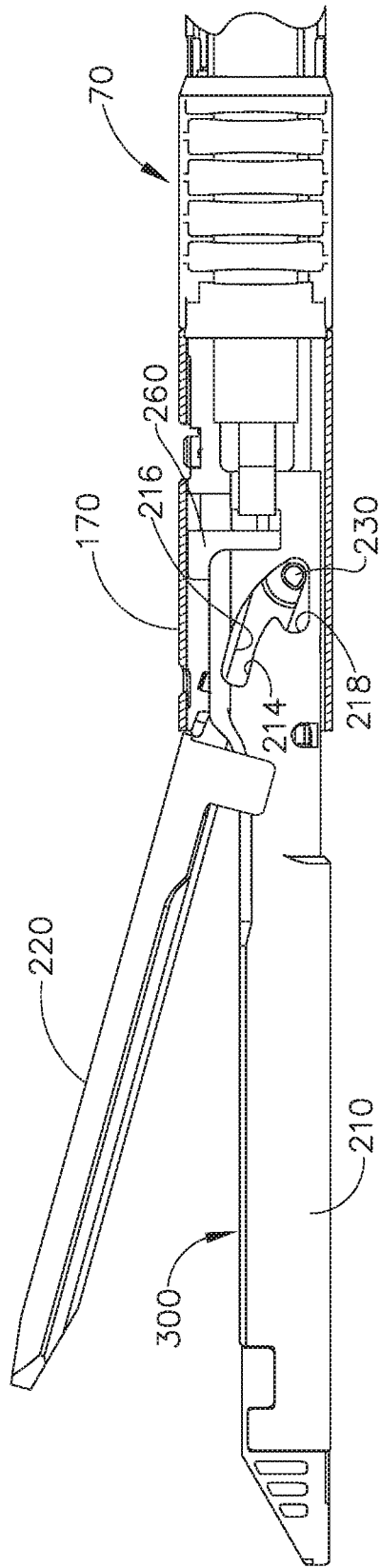
FIG. 20 is a side view of the end effector of FIGS. 16-19 with the staple cartridge embodiment seated within the elongate channel.

FIGS. 18 and 19 illustrate the initial insertion of the staple cartridge 300 into the elongate channel 210. FIGS. 20 and 21 illustrate the end effector 200 after the staple cartridge 300 has been fully seated in the elongate channel 210. As can be seen in FIG. 20 for example, when the cartridge 300 has been fully seated, the release members 320 on the cartridge 300 engage the trunnion walls 226, 228 and serve to move the anvil mounting portion 223 in a proximal direction "PD" such that the trunnion walls 226, 228 now pivotally rest on the release members 320. As can be seen in FIG. 21, when in that position, the anvil mounting portion 223 has moved proximally such that the trunnions 230 are moved out of their respective locking notches 218 and into the bottom of the arcuate slot segment 216 into an "actuatable" position whereby the anvil 220 may be pivoted closed by actuating the closure trigger 152.

Figure 22:
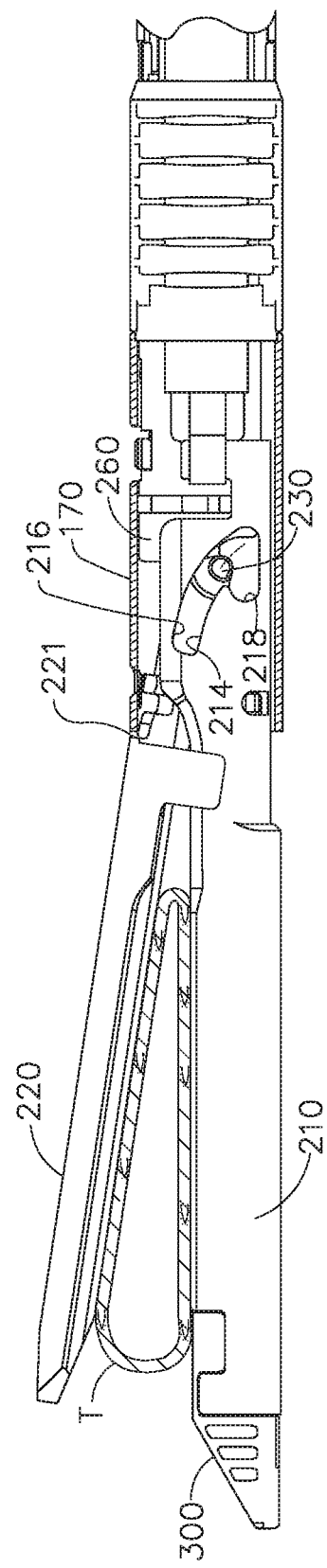
FIG. 22 is a side elevational view of the end effector of FIGS. 16-22 clamping tissue.
Figure 23:
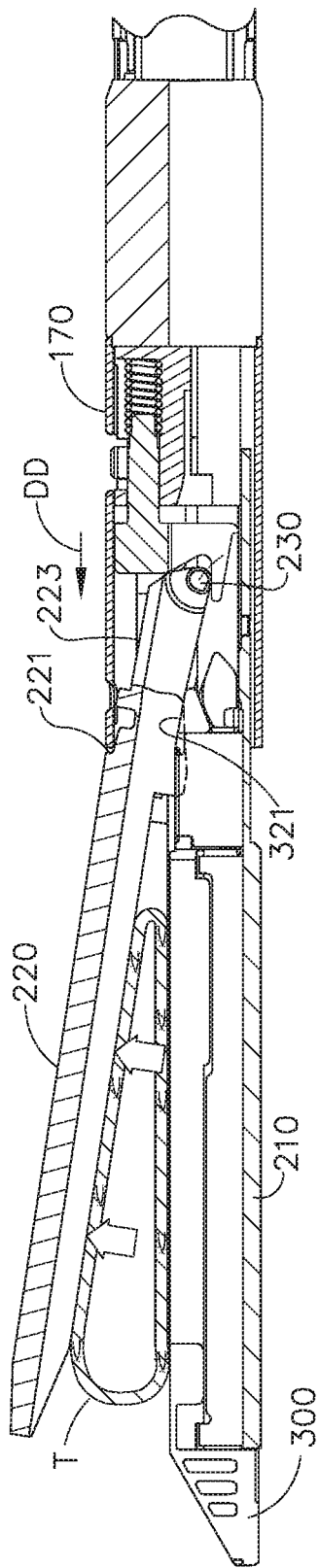
FIG. 23 is a cross-sectional view of the end effector of FIG. 22.

When the device 10 is in the starting position and the staple cartridge 300 has been loaded into the elongate channel as described above, both of the triggers 152, 102 are forward and the anvil 220 has been moved to the actuatable position, such as would be typical after inserting the loaded end effector 200 through a trocar or other opening into a body cavity. The instrument 10 is then manipulated by the clinician such that tissue "T" to be stapled and severed is positioned between the staple cartridge 300 and the anvil 200, as depicted in FIGS. 22 and 23. As discussed above, movement of the closure trigger 152 toward the pistol grip 24 causes the proximal closure tube segment 151, the flex neck assembly 70 and the distal closure tube segment 170 to move distally. As the distal closure tube segment 170 moves distally, it contacts a closure ledge 221 on the anvil 220. Pressure from the tissue captured between the anvil 220 and the staple cartridge 300 serves to move the anvil 220 such that the trunnions 230 are positioned to move within the arcuate trunnion slot segments 216. The surgeon may pivot the anvil 220 relative to the staple cartridge 300 to manipulate and capture the desired tissue "T" in the end effector 200. As the distal closure tube segment 170 contacts the closure ledge 221, the anvil 220 is pivoted towards a clamped position. The retracted knife bar 130 does not impede the selective opening and closing of the anvil 220.

Once the desired tissue "T" has been positioned between the anvil 220 and the cartridge 300, the clinician moves the closure trigger 152 proximally until positioned directly adjacent to the pistol grip 24, locking the handle 20 into the closed and clamped position. As can be seen in FIG. 25, when in the fully clamped position, the anvil trunnions 230 are located in the upper end of the arcuate slot portion 216 and the anvil tab 224 is received within the opening 176 in the distal closure tube segment 170. After tissue clamping has occurred, the clinician moves the firing trigger 102 proximally causing the knife bar 130 to move distally into the end effector 200. In particular, the knife bar 130 moves through the slot 236 in the pivot tab portion 234 of the anvil 220 and into the slot 304 in the cartridge body 302 to contact the wedge sled operably positioned within the staple cartridge 300. As the knife bar 130 is driven distally, it cuts the tissue T and drives the wedge sled distally which causes the staples to be sequentially fired into forming contact with the staple-forming undersurface 222 of the anvil 220. The clinician continues moving the firing trigger 102 until brought proximal to the closure trigger 152 and pistol grip 24. Thereby, all of the ends of the staples are bent over as a result of their engagement with the anvil 220. The cutting edge 132 has traversed completely through the tissue T. The process is complete by releasing the firing trigger 102 and by then depressing the release button 120 while simultaneously squeezing the closure trigger 152. Such action results in the movement of the distal closure tube segment 170 in the proximal direction "D". As the anvil tab 224 is engaged by the opening 176 in the distal closure tube segment 170 it causes the anvil to pivot open. The end surfaces 227, 229 again contact the pusher surfaces 263 on the anvil lock member 260 to pivot the anvil to the open position shown in FIGS. 20 and 21 to enable the spent cartridge 300 to be removed from the elongate channel 210.

Figure 26:
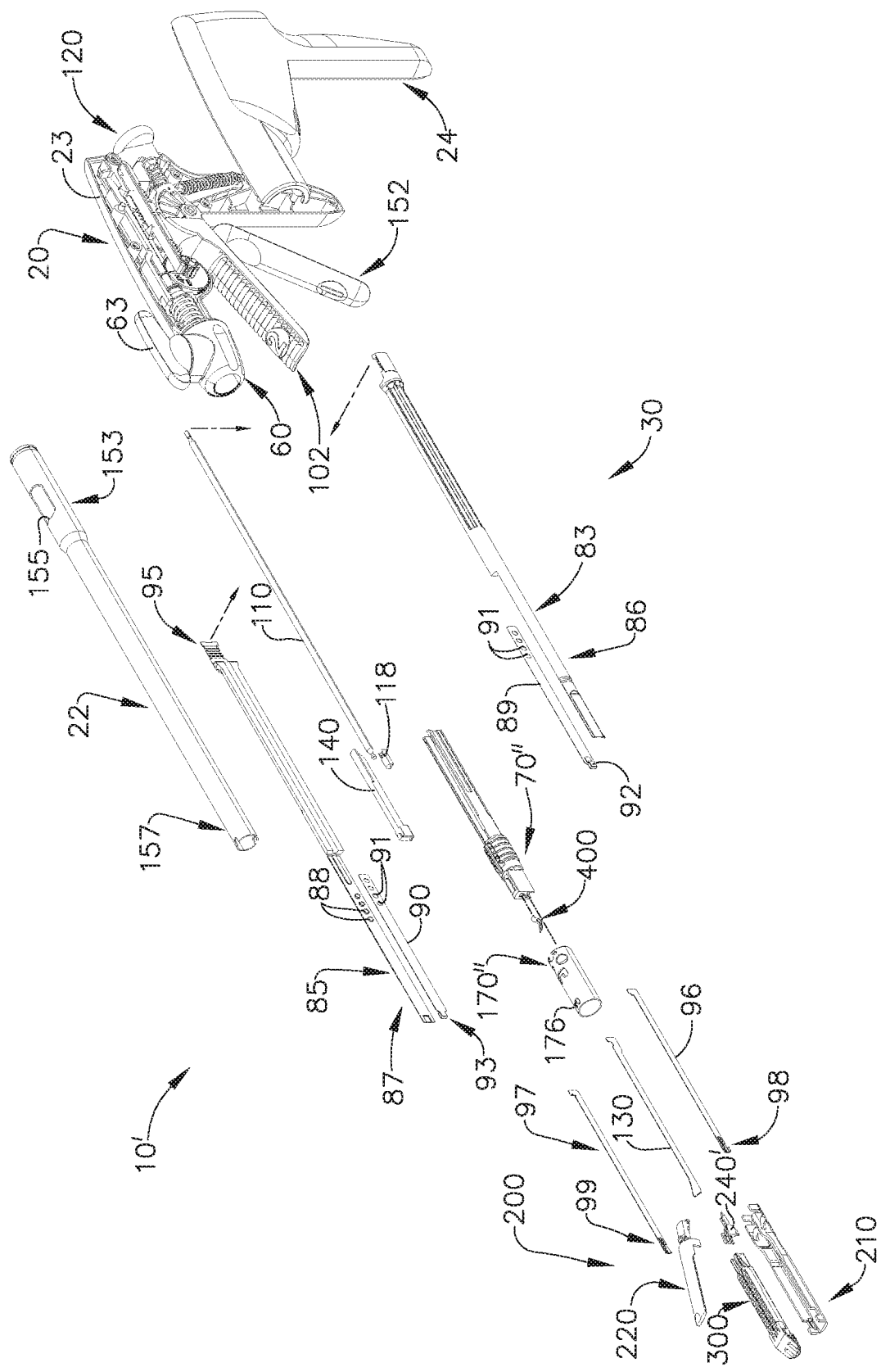
FIG. 26 is an exploded assembly view of another surgical stapling instrument embodiment.
Figure 28:
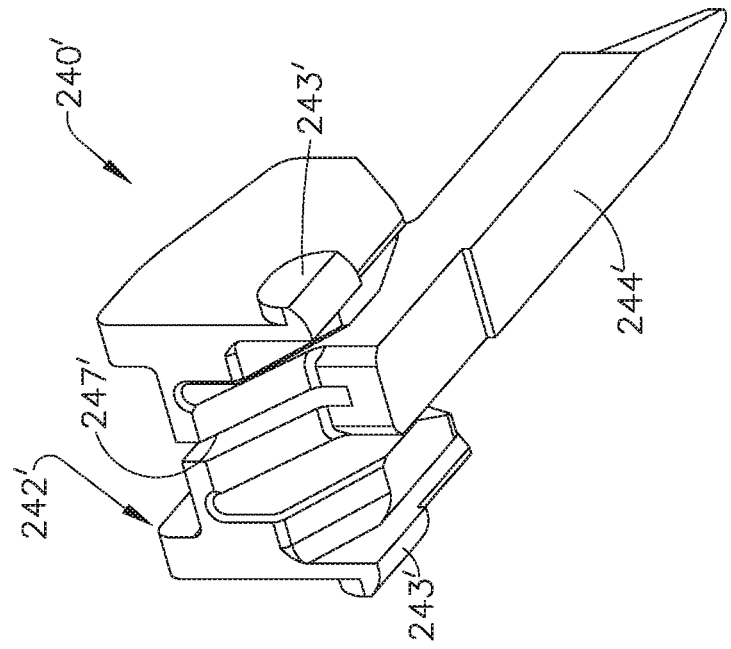
FIG. 28 is a bottom perspective view of the pivot mount embodiment of FIG. 27.
Figure 27:
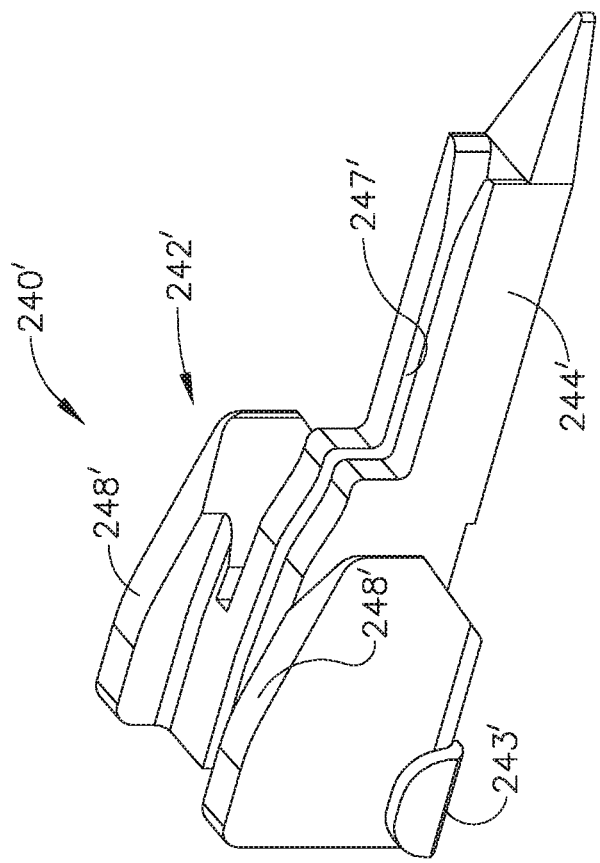
FIG. 27 is a perspective view of another pivot mount embodiment.

FIGS. 26-42 illustrate an alternative surgical stapling instrument 10' that is similar in construction and operation to surgical stapling instrument 10 except for the differences discussed below. This embodiment, for example, employs the pivot mount 240' illustrated in FIGS. 29 and 30. As can be seen in FIGS. 27 and 28 one form of a pivot mount 240' has a body portion 242' that is configured to be attached to the elongate channel 210. For example, the body portion 242' may be formed with two opposed attachment tabs 243' that are configured to retainingly engage tab openings 211 (FIG. 26) formed in the elongate channel 210. In addition, the pivot mount 240' has a proximally extending foot portion 244' that has a slot 247' extending therethrough for axially receiving the knife bar 130. Various embodiments of the pivot mount 240' further include rocker surfaces 248' formed on the body portion 242' for pivotally receiving the trunnion walls 226, 228 of the anvil 220 thereon.

This embodiment also includes an anvil lockout system 250' that prevents closure of the anvil 220 when a staple cartridge 300' has not been properly installed in the elongate channel 210. Referring to FIGS. 29 and 30, for example, an embodiment of an anvil lockout system 250' includes an anvil lock member 400 that is configured to contact the anvil mounting portion 223 as will be discussed in further detail below. In at least one form, the anvil lock member 400 comprises a leaf spring 402 that has a slot 404 therein for accommodating the knife bar 130. The leaf spring 402 is configured for attachment to the channel guide 79" of the flex neck assembly 70".

Figure 31:
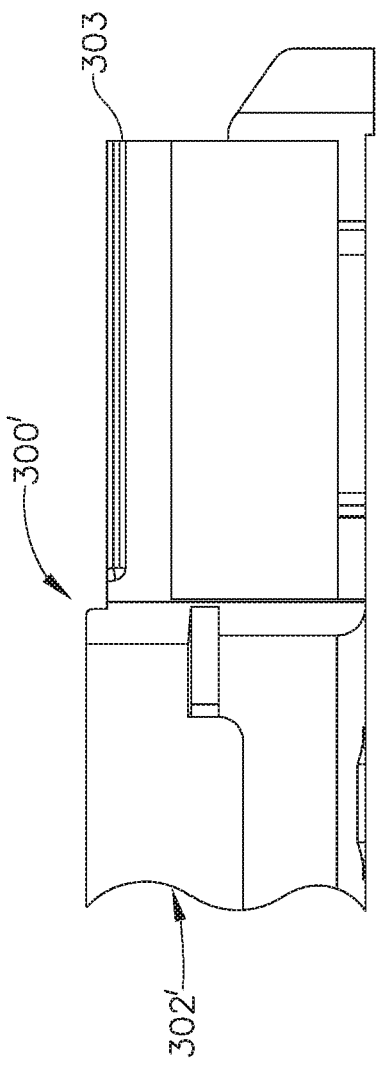
FIG. 31 is a partial side elevational view of a proximal end portion of another surgical staple cartridge embodiment.
Figure 32:
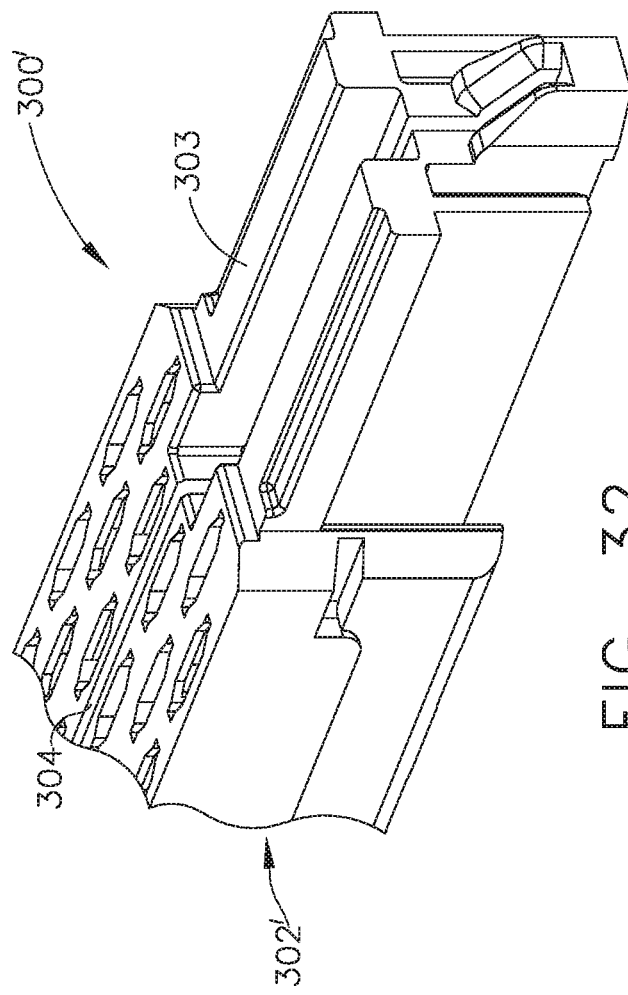
FIG. 32 is a perspective view of a proximal end portion of the surgical staple cartridge embodiment of FIG. 31.

As can be seen in FIGS. 31 and 32, in at least one form, the surgical staple cartridge 300' includes a cartridge body 302' that is similar to the surgical staple cartridge 300 described above, except for the differences discussed below. FIG. 29 depicts a wedge sled 360 that is supported within the cartridge body 302' in the manner described above. In this embodiment, the proximal end portion 303 of the cartridge body 302' is configured to contact a portion of the anvil mounting portion 223 and urge the anvil 220 proximally when the cartridge body 302' is seated within the elongate channel 210.

Figure 33:
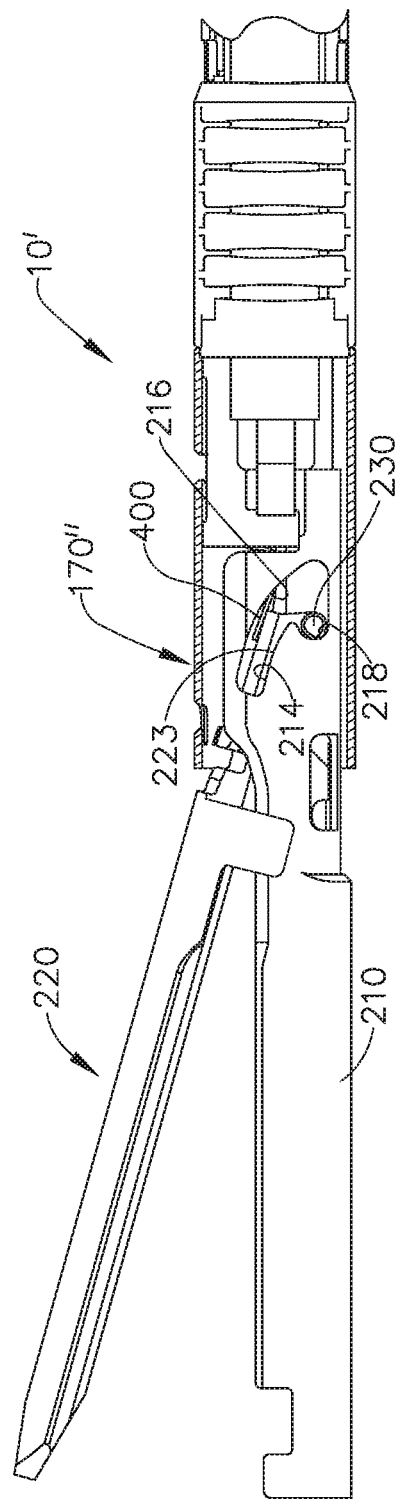
FIG. 33 is a side view of another end effector embodiment prior to seating a staple cartridge in the elongate channel.
Figure 34:
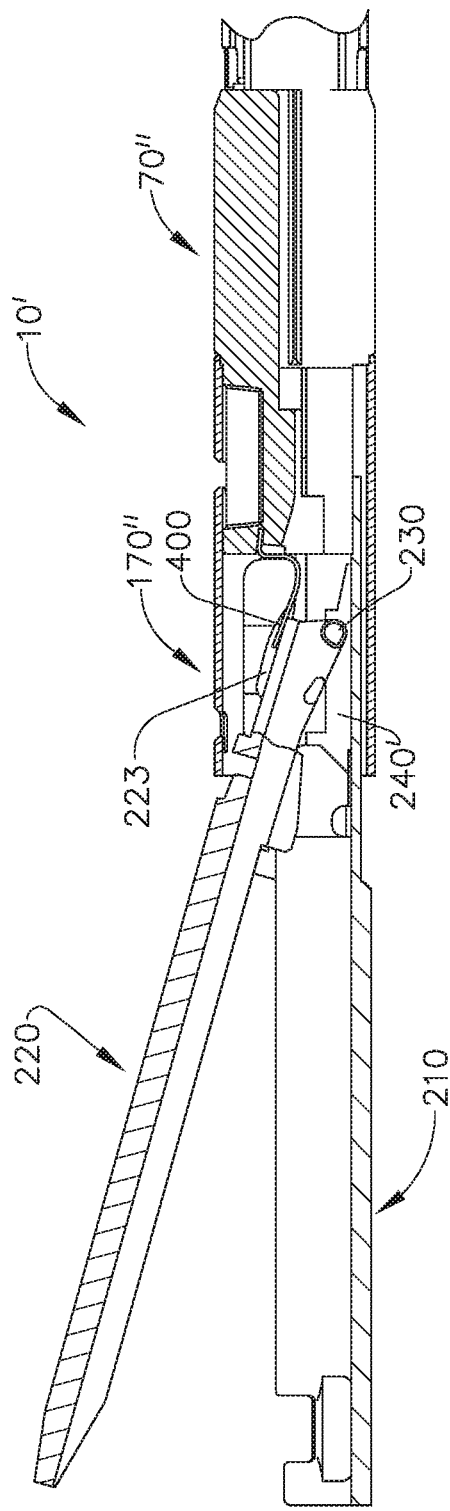
FIG. 34 is a cross-sectional view of the end effector depicted in FIG. 33.

An understanding of the operation of a anvil lockout system 250' may be gleaned from reference to FIGS. 33-43. FIGS. 33 and 34 illustrate the position of the anvil 220 relative to the elongate channel 210 prior to installing a staple cartridge 300'. When in that "unloaded" position, the anvil lock member 400 has engaged the upper surface of the anvil support portion 223 such that the anvil 220 is pivoted to the open position on the rocker surfaces 248' on the pivot mount 140'. When in that position, the trunnions 230 are seated in their respective locking notch 218. When in that position, the surgeon cannot close the anvil 220 by actuating the closure trigger 152 to advance the distal closure tube 170'. Because the closure tube segments cannot be advanced distally to close the anvil 220, the closure trigger 152 cannot be actuated to its fully closed position whereby the firing trigger 102 may be actuated. Thus, when no cartridge 300' is present, the end effector 200 may not be actuated.

FIGS. 35 and 36 illustrate the initial insertion of the staple cartridge 300' into the elongate channel 210. FIGS. 37 and 38 illustrate the end effector 200 after the staple cartridge 300' has been fully seated in the elongate channel 210. As can be seen in FIG. 37 for example, when the cartridge 300' has been fully seated, the proximal end portion 303 on the cartridge 300' engages the trunnion walls 226, 228 and serves to move the anvil mounting portion 223 in a proximal direction "PD" such that the trunnions are moved out of their respective locking notch 218 and into an actuatable position the bottom of the arcuate slot segment 216. The anvil 220 is now in position to be pivoted closed by actuating the closure trigger 152.

When the device 10' is in the starting position and the staple cartridge 300' has been loaded into the elongate channel 210 as described above, both of the triggers 152, 102 are forward and the anvil 220 is open and in the actuatable position, such as would be typical after inserting the loaded end effector 200 through a trocar or other opening into a body cavity. The instrument 10' is then manipulated by the clinician such that tissue "T" to be stapled and severed is positioned between the staple cartridge 300' and the anvil 220, as depicted in FIGS. 39 and 40. As discussed above, movement of the closure trigger 152 toward the pistol grip 24 causes the proximal closure tube segment 151, the flex neck assembly 70" and the distal closure tube segment 170" to move distally. As the distal closure tube segment 170' moves distally, it contacts a closure ledge 221 on the anvil 220. Pressure from the tissue captured between the anvil 220 and the staple cartridge 300' serves to move the anvil 220 such that the trunnions 230 are positioned to move within the arcuate trunnion slot segments 216. The surgeon may pivot the anvil 220 relative to the staple cartridge to manipulate and capture the desired tissue "T" in the end effector 200. As the distal closure tube segment 170" contacts the closure ledge 221, the anvil 220 is pivoted towards a clamped position. The retracted knife bar 130 does not impede the selective opening and closing of the anvil 220.

Figure 42:
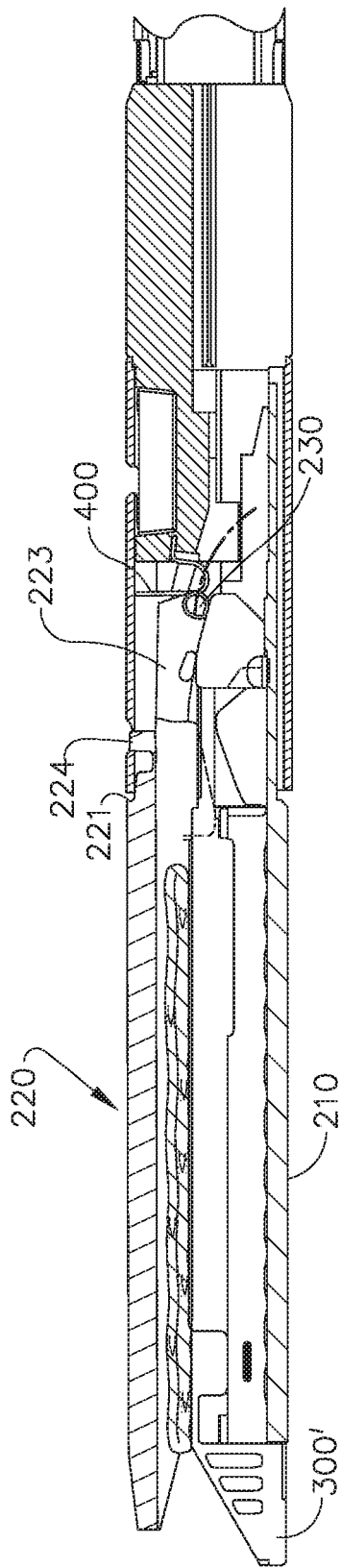
FIG. 42 is a cross-sectional view of the end effector of FIG. 41.
Figure 41:
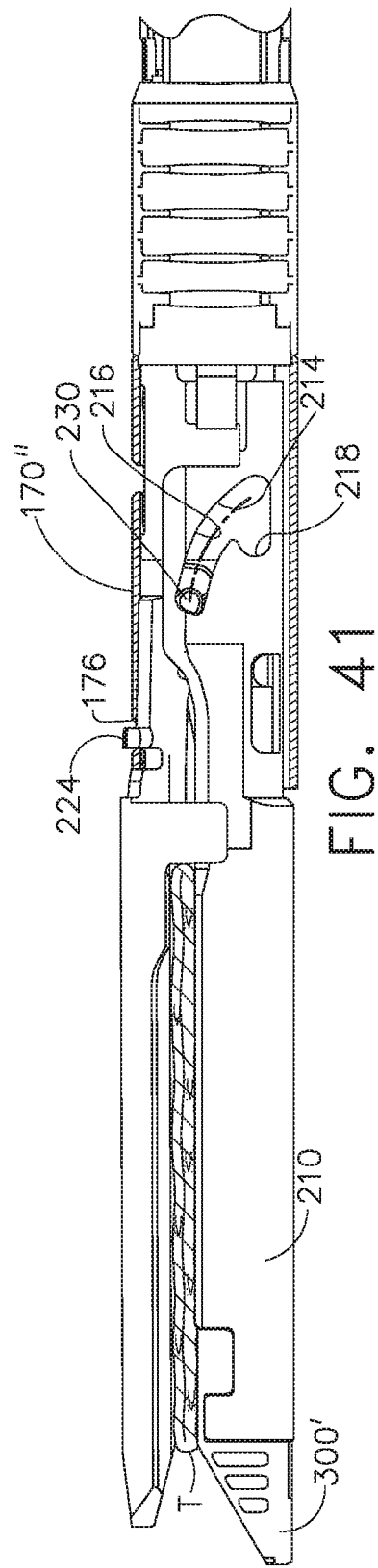
FIG. 41 is a side elevational view of the end effector of FIGS. 33-40 in a fully clamped position ready to fire.

Once the desired tissue "T" has been positioned between the anvil 220 and the cartridge 300', the clinician moves the closure trigger 152 proximally until positioned directly adjacent to the pistol grip 24, locking the handle 20 into the closed and clamped position. As can be seen in FIG. 42, when in the fully clamped position, the anvil trunnions 230 are located in the upper end of the arcuate slot portion 216 and the anvil tab 224 is received within the opening 176 in the distal closure tube segment 170". After tissue clamping has occurred, the clinician moves the firing trigger 102 proximally causing the knife bar 130 to move distally into the end effector 200. In particular, the knife bar 130 moves through the slot 236 in the pivot tab portion 234 of the anvil 220 and into the slot 304 in the cartridge body 302' to contact the wedge sled 360 operably positioned in therein. As the knife bar 130 is driven distally, it cuts the tissue T and drives the wedge sled 360 distally which causes the staples to be sequentially fired into forming contact with the staple-forming undersurface 222 of the anvil 220. The clinician continues moving the firing trigger 102 until brought proximal to the closure trigger 152 and pistol grip 24. Thereby, all of the ends of the staples are bent over as a result of their engagement with the anvil 220. The cutting edge 132 has traversed completely through the tissue T. The process is complete by releasing the firing trigger 102 and by then depressing the release button 120 while simultaneously squeezing the closure trigger 152. Such action results in the movement of the distal closure tube segment 170" in the proximal direction "D". As the anvil tab 224 is engaged by the opening 176 in the distal closure tube segment 170", it causes the anvil 220 to pivot open. The anvil lock member 400 applies a biasing force to the upper surface of the trunnion walls of the anvil mounting portion 223 and serves to pivot the anvil to the open position shown in FIGS. 33 and 34 to enable the spent cartridge 300' to be removed from the elongate channel 210.

The various unique and novel features of the above-described embodiments serve to prevent the end effector from being closed when a surgical staple cartridge is not present or has not been properly seated within the elongate channel. When the anvil is in the locked position wherein the anvil trunnions are retained in their respective locking notches, the anvil is retained in the open position. When in the open position, the end effector cannot be inadvertently inserted through a trocar. Because a full closure stroke is prevented, the firing system cannot be actuated. Thus, even if the clinician attempts to actuate the firing trigger, the device will not fire. Various embodiments also provide the clinician with feedback indicating that a cartridge is either not present or has not been properly installed in the elongate channel.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A surgical stapling instrument system, comprising:
   (a) a stapling instrument;
   (b) a staple cartridge configured to be attached to the stapling instrument;
   (c) staples removably stored within the staple cartridge;
   (d) a first jaw;
   (e) a second jaw moveable relative to the first jaw, wherein the second jaw is moveable relative to the first jaw between a locked position, an unlocked unclamped position, and a clamped position; and
   (f) a lock system configured to permit the second jaw to move to the clamped position when the staple cartridge is attached to the stapling instrument, and wherein the lock system is further configured to lock the second jaw in the locked position as a result of the staple cartridge not being attached to the stapling instrument,
   wherein the second jaw comprises a mounting portion pivotally supported on the first jaw, wherein the lock system comprises a lock member that is biased against the mounting portion, wherein the second jaw comprises a pair of trunnions, wherein the first jaw comprises a pair of trunnion slots configured to receive the pair of trunnions.

2. The surgical stapling instrument system of claim 1, wherein the lock system prevents the second jaw from moving toward the clamped position as a result of the staple cartridge not being attached to the stapling instrument.

3. The surgical stapling instrument system of claim 1, wherein the second jaw is configured to move from the locked position to the unlocked unclamped position upon an attachment of the staple cartridge to the stapling instrument.

4. The surgical stapling instrument system of claim 1, wherein the trunnion slots each comprise:
   (i) a locking notch for receiving the corresponding trunnion when the staple cartridge is not attached to the surgical stapling instrument, and
   (ii) an arcuate slot segment for receiving the corresponding trunnion when the staple cartridge is attached to the surgical stapling instrument, such that the corresponding trunnion may movably traverse within the respective arcuate slot segment upon application of a closing motion to the second jaw.

5. The surgical stapling instrument system of claim 4, wherein the lock member biases the mounting portion to seat and retain the pair of trunnions in the corresponding locking notches when the staple cartridge is not attached to the surgical stapling instrument.

6. The surgical stapling instrument system of claim 5, wherein the mounting portion is configured to pivot upon a portion of the first jaw.

7. The surgical stapling instrument system of claim 6, wherein the mounting portion comprises a pivot tab configured to pivot upon a pivot mount supported within the first jaw.

8. The surgical stapling instrument system of claim 1, wherein the lock member comprises a leaf spring configured for biasing contact with the mounting portion.

9. The surgical stapling instrument system of claim 1, wherein the lock system is proximal of the staple cartridge.

10. The surgical stapling instrument system of claim 1, wherein the second jaw is oriented at a first oblique angle relative to the first jaw when in the locked position.

11. The surgical stapling instrument system of claim 10, wherein the second jaw is oriented at a second oblique angle relative to the first jaw when in the unlocked unclamped position, wherein the second oblique angle is less than the first oblique angle.

12. A surgical stapling instrument system, comprising:
   (a) a stapling instrument;

(b) a staple cartridge configured to be attached to the stapling instrument;
(c) staples removably stored within the staple cartridge;
(d) a first jaw;
(e) a second jaw moveable relative to the first jaw, wherein the second jaw is moveable relative to the first jaw between a locked position, an unlocked unclamped position, and a clamped position; and
(f) a lock system configured to permit the second jaw to move to the clamped position when the staple cartridge is attached to the stapling instrument, and wherein the lock system is further configured to lock the second jaw in the locked position as a result of the staple cartridge not being attached to the stapling instrument,
wherein the second jaw comprises a mounting portion pivotally supported on the first jaw, wherein the lock system comprises a lock member that is biased against the mounting portion,
wherein the lock member comprises:
  (i) a body portion configured for contact with the mounting portion, and
  (ii) a biasing member cooperating with the body portion to bias the body portion into contact with the mounting portion.

13. The surgical stapling instrument system of claim 12, wherein the body portion includes at least one cam surface for contact with the mounting portion to cam the second jaw into the unlocked unclamped position when the staple cartridge is not attached to the surgical stapling instrument.

14. The surgical stapling instrument system of claim 12, wherein the biasing member includes a coil spring.

15. A surgical stapling instrument system, comprising:
(a) a stapling instrument;
(b) a staple cartridge configured to be attached to the stapling instrument;
(c) staples removably stored within the staple cartridge;
(d) a first jaw;
(e) a second jaw moveable relative to the first jaw, wherein the second jaw is moveable relative to the first jaw between a locked position, an unlocked unclamped position, and a clamped position; and
(f) a lock system configured to permit the second jaw to move to the clamped position when the staple cartridge is attached to the stapling instrument, and wherein the lock system is further configured to lock the second jaw in the locked position as a result of the staple cartridge not being attached to the stapling instrument,
wherein the second jaw comprises a mounting portion pivotally supported on the first jaw, wherein the lock system comprises a lock member that is biased against the mounting portion, wherein the lock member is biased in a distal direction.

16. A surgical stapling instrument system, comprising:
(a) a stapling instrument;
(b) a staple cartridge configured to be attached to the stapling instrument;
(c) staples removably stored within the staple cartridge;
(d) a first jaw;
(e) a second jaw moveable relative to the first jaw, wherein the second jaw is moveable relative to the first jaw between a locked position, an unlocked unclamped position, and a clamped position; and
(f) a lock system configured to permit the second jaw to move to the clamped position when the staple cartridge is attached to the stapling instrument, and wherein the lock system is further configured to lock the second jaw in the locked position as a result of the staple cartridge not being attached to the stapling instrument,
wherein the second jaw comprises a mounting portion pivotally supported on the first jaw, wherein the lock system comprises a lock member that is biased against the mounting portion, wherein the stapling instrument includes a knife bar, wherein the lock member includes a slot for allowing the knife bar to pass therethrough.

* * * * *